(12) United States Patent
Rothberg et al.

(10) Patent No.: US 12,312,377 B2
(45) Date of Patent: May 27, 2025

(54) BICONJUGATABLE LABELS AND METHODS OF USE

(71) Applicant: Quantum-Si Incorporated, Guilford, CT (US)

(72) Inventors: Jonathan M. Rothberg, Guilford, CT (US); Jeremy Lackey, Guilford, CT (US); Roger Nani, Madison, CT (US); David Dodd, Guilford, CT (US)

(73) Assignee: Quantum-Si Incorporated, Branford, CT (US)

( * ) Notice: Subject to any disclaimer, the term of this patent is extended or adjusted under 35 U.S.C. 154(b) by 856 days.

(21) Appl. No.: 16/510,794

(22) Filed: Jul. 12, 2019

(65) Prior Publication Data
US 2020/0031861 A1    Jan. 30, 2020

Related U.S. Application Data

(60) Provisional application No. 62/698,006, filed on Jul. 13, 2018.

(51) Int. Cl.
| | | |
|---|---|---|
| *C07H 21/00* | (2006.01) | |
| *A61K 49/00* | (2006.01) | |
| *C07F 5/02* | (2006.01) | |
| *C07H 21/04* | (2006.01) | |
| *C09B 11/24* | (2006.01) | |
| *C09B 23/01* | (2006.01) | |
| *C09B 57/00* | (2006.01) | |

(52) U.S. Cl.
CPC ......... *C07H 21/04* (2013.01); *A61K 49/0032* (2013.01); *C07F 5/022* (2013.01); *C09B 11/24* (2013.01); *C09B 23/0075* (2013.01); *C09B 57/00* (2013.01)

(58) Field of Classification Search
CPC .......... C07H 21/04; C07H 21/00; C07H 1/00; A61K 49/0032; C07F 5/022; C09B 11/24; C09B 23/0075; C09B 57/00; C07D 405/14; C07D 491/22; C07D 493/10; G01N 33/532; G01N 33/533; C12Q 1/6869; C12Q 2563/103
See application file for complete search history.

(56) References Cited

U.S. PATENT DOCUMENTS

| | | |
|---|---|---|
| 5,210,015 A | 5/1993 | Gelfand et al. |
| 5,487,972 A | 1/1996 | Gelfand et al. |
| 5,594,117 A | 1/1997 | Urdea et al. |
| 5,707,804 A | 1/1998 | Mathies et al. |
| 5,851,840 A | 12/1998 | Sluka et al. |
| 6,133,445 A | 10/2000 | Waggoner et al. |
| 6,153,442 A | 11/2000 | Pirio et al. |
| 6,248,518 B1 | 6/2001 | Parkhurst et al. |
| 6,255,083 B1 | 7/2001 | Williams |
| 6,399,335 B1 | 6/2002 | Kao et al. |
| 6,444,682 B1 | 9/2002 | Simmonds et al. |
| 6,762,048 B2 | 7/2004 | Williams |
| 6,787,308 B2 | 9/2004 | Balasubramanian et al. |
| 6,846,638 B2 | 1/2005 | Shipwash |
| 6,869,764 B2 | 3/2005 | Williams et al. |
| 6,936,702 B2 | 8/2005 | Williams et al. |
| 7,041,812 B2 | 5/2006 | Kumar et al. |
| 7,052,847 B2 | 5/2006 | Korlach et al. |
| 7,056,661 B2 | 6/2006 | Korlach et al. |
| 7,057,026 B2 | 6/2006 | Barnes et al. |
| 7,229,799 B2 | 6/2007 | Williams |
| 7,361,466 B2 | 4/2008 | Korlach et al. |
| 7,405,281 B2 | 7/2008 | Xu et al. |
| 7,625,701 B2 | 12/2009 | Williams et al. |
| 7,968,702 B2 | 6/2011 | Wegener et al. |
| 7,973,146 B2 | 7/2011 | Shen et al. |
| 8,034,623 B2 | 10/2011 | Oh et al. |
| 8,084,734 B2 | 12/2011 | Vertes et al. |
| 8,133,702 B2 | 3/2012 | Shen et al. |
| 8,148,516 B2 | 4/2012 | Williams et al. |
| 8,153,375 B2 | 4/2012 | Travers et al. |
| 8,192,961 B2 | 6/2012 | Williams |
| 8,252,910 B2 | 8/2012 | Korlach et al. |
| 8,257,954 B2 | 9/2012 | Clark et al. |
| 8,309,330 B2 | 11/2012 | Travers et al. |
| 8,354,252 B2 | 1/2013 | Wegener et al. |
| 8,383,791 B1 | 2/2013 | McDowell et al. |
| 8,420,366 B2 | 4/2013 | Clark et al. |
| 8,455,193 B2 | 6/2013 | Travers et al. |
| 8,530,154 B2 | 9/2013 | Williams |
| 8,581,179 B2 | 11/2013 | Franzen |
| 8,846,881 B2 | 9/2014 | Korlach et al. |
| 8,906,614 B2 | 12/2014 | Wegener et al. |
| 8,927,212 B2 | 1/2015 | Kong et al. |

(Continued)

FOREIGN PATENT DOCUMENTS

| | | |
|---|---|---|
| CA | 2373385 C | 11/2000 |
| CA | 2457513 A1 | 3/2003 |

(Continued)

OTHER PUBLICATIONS

Demeter et al. (Bioconj. Chem. 2017, 28, 1552-1559).*
Demeter et al. (Chem. Eur. J. 2016, 22, 6382-6388).*
Gutsche et al. (Chem. Eur. J. 2016, 22, 13953-19364).*
Linck et al. (Photochem. Photobiol. 2012, 88, 867-875).*
Lakshmi et al. (Reports Org. Chem. 2016, 6, 1-24 ).*
Kowada et al. (Chem. Soc. Rev. 2015, 44, 4953-4972).*
Gerowska, M. (2012). Synthesis and Properties of New Fluorescent Dyes and Dye-Labelled Oligonucleotides, Thesis for the degree of Doctor of Philosophy, University of Southampton).*
Ryabinin et al. (Russian J. Bioorg. Chem. 2016, 42, 111-114).*
Algar et al. (Analyt. Chim. Acta 2007, 581, 193-201).*

(Continued)

*Primary Examiner* — Michael G. Hartley
*Assistant Examiner* — Melissa J Perreira
(74) *Attorney, Agent, or Firm* — Wolf, Greenfield & Sacks, P.C.

(57) ABSTRACT

Aspects of the disclosure provide biconjugatable labels, labeled biomolecules, and methods of using and making the same.

15 Claims, 4 Drawing Sheets

(56) References Cited

U.S. PATENT DOCUMENTS

| | | |
|---|---|---|
| 8,980,584 B2 | 3/2015 | Williams |
| 9,062,091 B2 | 6/2015 | Bjornson et al. |
| 9,404,146 B2 | 8/2016 | Travers et al. |
| 9,435,810 B2 | 9/2016 | Havranek et al. |
| 9,464,107 B2 | 10/2016 | Wegener et al. |
| 9,542,527 B2 | 1/2017 | Travers et al. |
| 9,551,031 B2 | 1/2017 | Korlach et al. |
| 9,551,660 B2 | 1/2017 | Kong et al. |
| 9,566,335 B1 | 2/2017 | Emili et al. |
| 9,582,640 B2 | 2/2017 | Travers et al. |
| 9,600,626 B2 | 3/2017 | Travers et al. |
| 9,678,080 B2 | 6/2017 | Bjornson et al. |
| 9,719,073 B2 | 8/2017 | Emig et al. |
| 9,845,501 B2 | 12/2017 | Williams |
| 9,879,319 B2 | 1/2018 | Korlach et al. |
| 9,910,956 B2 | 3/2018 | Travers et al. |
| 9,957,291 B2 | 5/2018 | Sebo et al. |
| 10,023,605 B2 | 7/2018 | Bjornson et al. |
| 10,066,258 B2 | 9/2018 | Kong et al. |
| 10,150,872 B2 | 12/2018 | Zheng et al. |
| 10,161,002 B2 | 12/2018 | Korlach et al. |
| 10,174,363 B2 | 1/2019 | Rothberg et al. |
| 10,481,162 B2 | 11/2019 | Emili et al. |
| 10,544,449 B2 | 1/2020 | Shen et al. |
| 10,545,153 B2 | 1/2020 | Marcotte et al. |
| 10,570,445 B2 | 2/2020 | Kong et al. |
| 10,676,788 B2 | 6/2020 | Shen et al. |
| 10,745,750 B2 | 8/2020 | Korlach et al. |
| 10,787,573 B2 | 9/2020 | Zheng et al. |
| 11,001,875 B2 | 5/2021 | Rothberg et al. |
| 11,613,772 B2 | 3/2023 | Rothberg et al. |
| 11,655,504 B2 | 5/2023 | Rothberg et al. |
| 2002/0182625 A1 | 12/2002 | McGall |
| 2003/0124576 A1 | 7/2003 | Kumar et al. |
| 2003/0138809 A1 | 7/2003 | Williams et al. |
| 2003/0143591 A1 | 7/2003 | Davies et al. |
| 2005/0014154 A1 | 1/2005 | Weizenegger |
| 2005/0042633 A1 | 2/2005 | Williams |
| 2005/0266456 A1 | 12/2005 | Williams et al. |
| 2007/0072196 A1 | 3/2007 | Xu et al. |
| 2007/0219367 A1 | 9/2007 | Shchepinov et al. |
| 2009/0068645 A1 | 3/2009 | Sibson |
| 2009/0104614 A1 | 4/2009 | Tsourkas et al. |
| 2009/0117540 A1 | 5/2009 | Sorge |
| 2009/0214436 A1 | 8/2009 | Achilefu et al. |
| 2009/0233302 A1 | 9/2009 | Wegener et al. |
| 2009/0263327 A1* | 10/2009 | Achilefu ............... A61K 31/405 424/9.4 |
| 2009/0263802 A1 | 10/2009 | Drmanac |
| 2010/0009872 A1 | 1/2010 | Eid et al. |
| 2010/0029494 A1 | 2/2010 | Cherkasov et al. |
| 2010/0034750 A1 | 2/2010 | Perfect et al. |
| 2010/0035254 A1 | 2/2010 | Williams |
| 2010/0093553 A1 | 4/2010 | Park et al. |
| 2010/0129822 A1 | 5/2010 | Siva et al. |
| 2010/0152424 A1 | 6/2010 | Korlach et al. |
| 2010/0317005 A1 | 12/2010 | Hardin et al. |
| 2011/0003343 A1 | 1/2011 | Nikiforov et al. |
| 2011/0165652 A1 | 7/2011 | Hardin et al. |
| 2011/0212437 A1 | 9/2011 | Emig et al. |
| 2011/0256549 A1 | 10/2011 | Gaylord et al. |
| 2011/0281776 A1 | 11/2011 | Eshoo et al. |
| 2012/0016128 A1* | 1/2012 | Diwu ................. C07F 9/65517 546/14 |
| 2012/0322692 A1 | 12/2012 | Pham et al. |
| 2013/0240359 A1 | 9/2013 | Turner et al. |
| 2013/0316912 A1 | 11/2013 | Bjornson et al. |
| 2014/0094375 A1 | 4/2014 | Kamtekar et al. |
| 2015/0050659 A1 | 2/2015 | Sebo et al. |
| 2015/0293022 A1 | 10/2015 | Buckhout-White et al. |
| 2015/0330987 A1 | 11/2015 | Bjornson et al. |
| 2017/0136433 A1 | 5/2017 | Sun et al. |
| 2017/0362651 A1 | 12/2017 | Rothberg et al. |
| 2018/0002736 A1* | 1/2018 | O'Connell ............ C12Q 1/6818 |
| 2018/0211003 A1 | 7/2018 | Travers et al. |
| 2018/0299460 A1 | 10/2018 | Emili |
| 2018/0346507 A1 | 12/2018 | Sebo et al. |
| 2019/0010183 A1 | 1/2019 | Bjornson et al. |
| 2019/0024168 A1 | 1/2019 | Rothberg et al. |
| 2019/0249153 A1 | 8/2019 | Kamtekar et al. |
| 2019/0330688 A1 | 10/2019 | Rothberg et al. |
| 2020/0141944 A1 | 5/2020 | Emili et al. |
| 2020/0148727 A1 | 5/2020 | Tullman et al. |
| 2020/0232017 A1 | 7/2020 | Rothberg et al. |
| 2023/0221330 A1 | 7/2023 | Reed et al. |
| 2024/0035081 A1 | 2/2024 | Rothberg et al. |
| 2024/0068027 A1 | 2/2024 | Rothberg et al. |
| 2024/0124918 A1 | 4/2024 | Rothberg et al. |

FOREIGN PATENT DOCUMENTS

| | | |
|---|---|---|
| CN | 1373813 A | 10/2002 |
| CN | 1771336 A | 5/2006 |
| CN | 1938328 A | 3/2007 |
| CN | 101076537 A | 11/2007 |
| CN | 101268200 A | 9/2008 |
| CN | 101346472 A | 1/2009 |
| CN | 101434988 A | 5/2009 |
| CN | 101636406 A | 1/2010 |
| CN | 102124128 A | 7/2011 |
| CN | 102329884 A | 1/2012 |
| CN | 102782159 A | 11/2012 |
| CN | 103866010 A | 6/2014 |
| CN | 105001292 A | 10/2015 |
| EP | 1681356 A1 | 7/2006 |
| EP | 1421213 B1 | 2/2010 |
| EP | 1179085 B1 | 5/2010 |
| EP | 2226330 A1 | 9/2010 |
| EP | 2263087 A1 | 12/2010 |
| EP | 2814953 | 12/2014 |
| GB | 2398383 A | 8/2004 |
| JP | H07-502992 A | 3/1995 |
| JP | 2002-508428 | 3/2002 |
| JP | 2002-543847 | 12/2002 |
| JP | 2005-507674 A | 3/2005 |
| JP | 2009-518009 A | 5/2009 |
| JP | 2015-073523 A | 4/2015 |
| JP | 2016-011429 A | 1/2016 |
| WO | WO 1993/09128 A1 | 5/1993 |
| WO | WO 00/70073 A1 | 11/2000 |
| WO | WO 2001/09389 A2 | 2/2001 |
| WO | WO 03/089670 A2 | 10/2003 |
| WO | WO 2003/102239 A2 | 12/2003 |
| WO | WO 2004/096997 A2 | 11/2004 |
| WO | WO 2005/044836 A2 | 5/2005 |
| WO | WO 2007/015168 A2 | 2/2007 |
| WO | WO 2007/041342 A2 | 4/2007 |
| WO | WO 2007/064905 A2 | 6/2007 |
| WO | WO 2007/070572 A2 | 6/2007 |
| WO | WO 2009/114182 A1 | 9/2009 |
| WO | WO 2010/065322 A1 | 6/2010 |
| WO | WO 2010/115016 A2 | 10/2010 |
| WO | WO 2010/117420 A2 | 10/2010 |
| WO | WO 2011/150852 A1 | 12/2011 |
| WO | WO 2012/027625 A2 | 3/2012 |
| WO | WO 2016/187580 A1 | 11/2016 |
| WO | WO 2017/201514 A1 | 11/2017 |
| WO | WO 2019/023257 A1 | 1/2019 |
| WO | WO 2019/040825 A1 | 2/2019 |

OTHER PUBLICATIONS

Inoyama et al. (J. Biomol. Screen. 2012, 17, 435-447).*
Extended European Search Report mailed May 6, 2021 for Application No. EP 18837972.1.
International Preliminary Report on Patentability for Application No. PCT/US2018/043526 mailed Feb. 6, 2020.
International Search Report and Written Opinion for Application No. PCT/US2019/041717 mailed Nov. 13, 2019.
International Preliminary Report on Patentability for Application No. PCT/US2019/041717 mailed Jan. 28, 2021.
Invitation to Pay Additional Fees for International Application No. PCT/US2020/014856 mailed May 8, 2020.

(56) References Cited

OTHER PUBLICATIONS

International Search Report and Written Opinion for International Application No. PCT/US2020/014856 mailed Jun. 30, 2020.
International Preliminary Report on Patentability for International Application No. PCT/US2020/014856 mailed Aug. 5, 2021.
Bunt et al., FRET from single to multiplexed signaling events. Biophys Rev. 2017;9:119-29. Epub Mar. 23, 2017.
Koushik et al., Cerulean, Venus, and VenusY67C FRET reference standards. Biophys J. Dec. 15, 2006;91(12):L99-L101. doi: 10.1529/biophysj.106.096206. Epub Oct. 13, 2006. PMID: 17040988; PMCID: PMC1779932.
Saito et al., Dual-labeled oligonucleotide probe for sensing adenosine via FRET: a novel alternative to SNPs genotyping. Chem Commun (Camb). Jun. 7, 2007;(21):2133-5. doi: 10.1039/b618465k. Epub Feb. 28, 2007. PMID: 17520113.
Sato et al., Polyproline-rod approach to isolating protein targets of bioactive small molecules: isolation of a new target of indomethacin. J Am Chem Soc. Jan. 31, 2007;129(4):873-80. doi: 10.1021/ja0655643. PMID: 17243824.
Stryer et al., Energy transfer: a spectroscopic ruler. Proc Natl Acad Sci U S A. Aug. 1967;58(2):719-26. doi: 10.1073/pnas.58.2.719. PMID: 5233469; PMCID: PMC335693.
Williams et al., An artificial processivity clamp made with streptavidin facilitates oriented attachment of polymerase—DNA complexes to surfaces. Nucleic Acids Res. Oct. 2008;36(18):e121. doi: 10.1093/nar/gkn531. Epub Aug. 22, 2008.
U.S. Appl. No. 61/069,247, filed Mar. 13, 2008, Korlach et al.
U.S. Appl. No. 61/979,724, filed Apr. 14, 2014.
International Search Report and Written Opinion for International Application No. PCT/US2017/033706 dated Sep. 12, 2017.
International Preliminary Report on Patentability for International Application No. PCT/US2017/033706 dated Nov. 29, 2018.
International Search Report and Written Opinion for International Application No. PCT/US2018/043526 dated Oct. 3, 2018.
Invitation to Pay Additional Fees for Application No. PCT/US2019/041717 mailed Sep. 20, 2019.
Brown et al., Synthesis of a modified thymidine monomer for site-specific incorporation of reporter groups into oligonucleotides. Tetrahedron Letters. 2001;42:2587-2591.
Cheng-Yao, DNA polymerases drive DNA sequencing-by-synthesis technologies: both past and present. Frontiers in Microbiology. 2014. 10 pages.
Kretschy et al., Comparison of the sequence-dependent fluorescence of the cyanine dyes Cy3, Cy5, DyLight DY547 and DyLight DY647 on single-stranded DNA. PLoS One. Jan. 15, 2014;9(1):e85605. doi: 10.1371/journal.pone.0085605. eCollection 2014.
Kumar et al., Terminal phosphate labeled nucleotides: synthesis, applications, and linker effect on incorporation by DNA polymerases. Nucleosides Nucleotides Nucleic Acids. Nov. 2005; 24(5-7):401-8.
Takkellapati et al., Synthesis of aminomethyl- and bis-aminomethyl-fluorescein energy transfer terminators. Nucleosides Nucleotides Nucleic Acids. Dec. 2007; 26(10-12):1467-70.
U.S. Appl. No. 15/600,979, filed May 22, 2017, Rothberg et al.
U.S. Appl. No. 15/161,125, filed May 20, 2016, Rothberg et al.
U.S. Appl. No. 16/043,547, filed Jul. 24, 2018, Rothberg et al.
PCT/US2017/033706, Sep. 12, 2017, International Search Report and Written Opinion.
PCT/US2017/033706, Nov. 29, 2018, International Preliminary Report on Patentability.
PCT/US2018/043526, Oct. 3, 2018, International Search Report and Written Opinion.
PCT/US2019/041717, Sep. 20, 2019, Invitation to Pay Additional Fee.
Antonio et al., Boronic acids as building blocks for the construction of therapeutically useful bioconjugates. Chem Soc Rev. Jul. 1, 2019;48(13):3513-3536. doi: 10.1039/c9cs00184k.
Lee et al., Bodipy-diacrylate imaging probes for targeted proteins inside live cells. Chem Commun (Camb). Apr. 21, 2011;47(15):4508-10. doi: 10.1039/c1cc10362h. Epub Mar. 8, 2011.
Scheck et al., Surveying protein structure and function using bis-arsenical small molecules. Acc Chem Res. Sep. 20, 2011;44(9):654-65. doi: 10.1021/ar2001028. Epub Jul. 18, 2011.
Sun et al., Boronic acids for fluorescence imaging of carbohydrates. Chem Commun (Camb). Feb. 28, 2016;52(17):3456-69. doi: 10.1039/c5cc08633g. Epub Jan. 5, 2016.
Vives et al., Facile functionalization of a fully fluorescent perfluorophenyl BODIPY: photostable thiol and amine conjugates. Chem Commun (Camb). Oct. 7, 2011;47(37):10425-7. doi: 10.1039/c1cc13778f. Epub Aug. 19, 2011.
Li et al., A photocleavable fluorescent nucleotide for DNA sequencing and analysis. Proceedings of the National Academy of Sciences. Jan. 21, 2003;100(2):414-9.
Hall et al., A highly fluorescent DNA toolkit: synthesis and properties of oligonucleotides containing new Cy3, Cy5 and Cy3B monomers. Nucleic acids research. Aug. 1, 2012;40(14):e108-. 10 pages.
U.S. Appl. No. 18/153,093, filed Jan. 11, 2023, Reed et al.

* cited by examiner

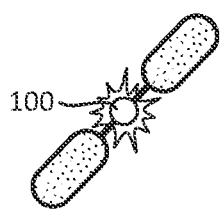
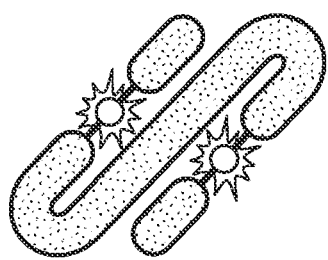
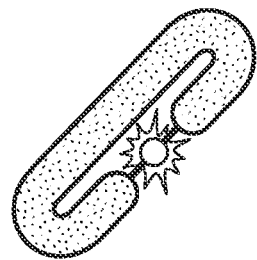
FIG. 1A        FIG. 1B        FIG. 1C
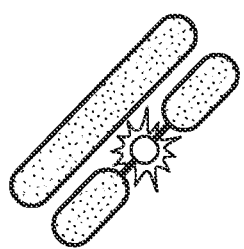
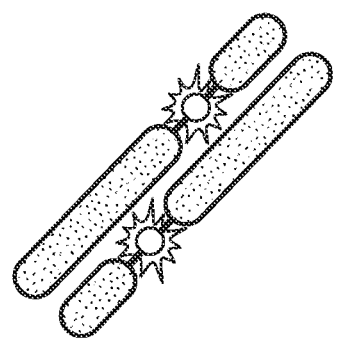
FIG. 1D        FIG. 1E
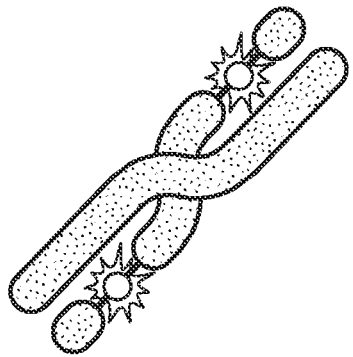
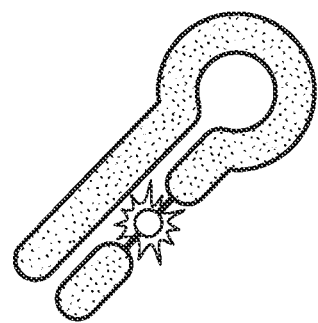
FIG. 1F        FIG. 1G

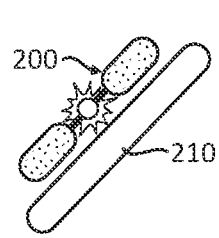
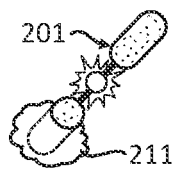
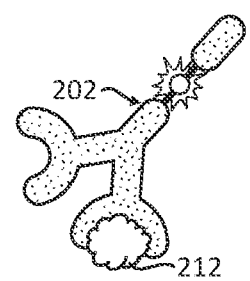
FIG. 2A          FIG. 2B          FIG. 2C
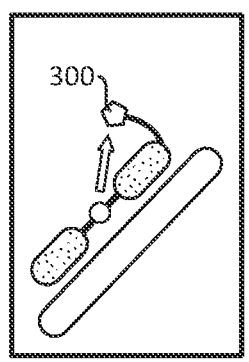
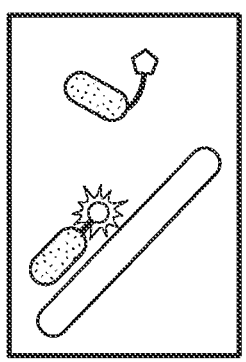
FIG. 3A          FIG. 3B
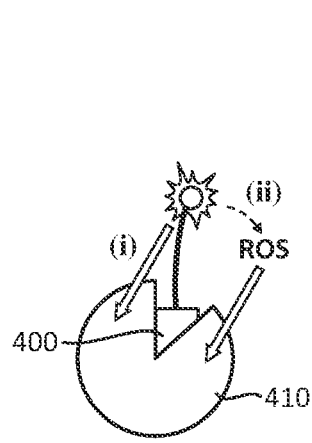
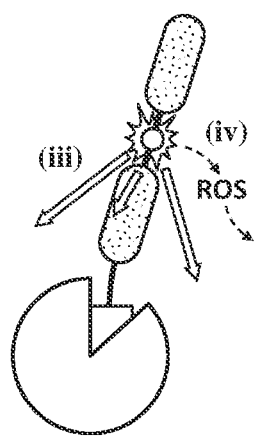
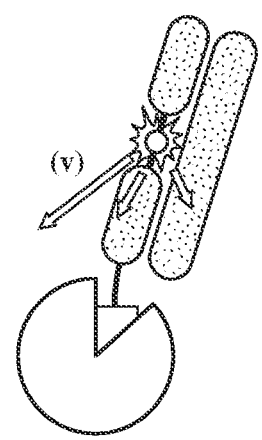
FIG. 4A          FIG. 4B          FIG. 4C

BICONJUGATABLE LABELS AND METHODS OF USE

CROSS-REFERENCE TO RELATED APPLICATIONS

This application claims priority under 35 U.S.C. § 119(e) to U.S. Provisional Patent Application No. 62/698,006, filed Jul. 13, 2018, which is hereby incorporated by reference in its entirety.

BACKGROUND

Labeled probes are widely used in methods for detecting biological analytes and analyzing biological processes. Some of these techniques involve monitoring a biological reaction in real-time using luminescently labeled reaction components. The labels are illuminated with a light source to cause luminescence, and the luminescent light is detected with a photodetector. These events can be recorded and analyzed to identify individual reaction components based on corresponding luminescent properties. In identifying a specific type of labeled molecule among a plurality of types, it is critical that each type exhibits unique and readily differentiable luminescent properties. However, the inherent sensitivity of complex biological processes requires careful consideration when designing labeled probes for use in these systems.

SUMMARY

Aspects of the disclosure relate to labeled biomolecules comprising internally-conjugated luminescent labels. In some aspects, the disclosure provides labeled biomolecules comprising a substrate configured for use in a reaction. In some aspects, the disclosure provides labeled biomolecules comprising a nucleotide configured for use in a polymerization reaction. In some aspects, the disclosure provides methods of sequencing using labeled nucleotides described herein. In some aspects, the disclosure provides biconjugatable luminescent labels and methods of making the same.

In some aspects, the application provides labeled biomolecules of Formula (I):

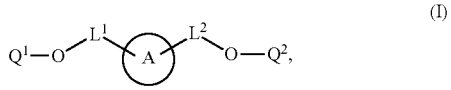

(I)

wherein: $Q^1$ and $Q^2$ are independently monomeric or oligomeric biomolecules: A is a polycyclic fluorophore; and $L^1$ and $L^2$ are independently linkers selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, optionally substituted heteroarylene, and combinations thereof.

In some aspects, provided herein is a labeled nucleotide comprising one or more nucleotides associated with a labeled biomolecule according to the present application. In some embodiments, the one or more nucleotides comprise one type of nucleotide selected from guanine, cytosine, adenine, and thymine or uracil. In some embodiments, the one or more nucleotides are cleaved from the labeled biomolecule by a polymerase when subjected to polymerization reaction conditions. In some embodiments, the one or more nucleotides comprise nucleoside polyphosphates. In some embodiments, the one or more nucleotides comprise nucleoside triphosphates. In some embodiments, the one or more nucleotides comprise nucleoside hexaphosphates. In some embodiments, the one or more nucleotides (e.g., nucleoside polyphosphates) are attached through a terminal phosphate to the labeled biomolecule. In some aspects, provided herein are compositions comprising a labeled nucleotide according to the present application.

In some aspects, provided herein is a nucleic acid sequencing reaction composition comprising two or more different types of labeled nucleotides in a reaction mixture. In some embodiments, at least one type of labeled nucleotide of the nucleic acid sequencing reaction composition is a labeled nucleotide according to the present application. In some embodiments, the nucleic acid sequencing reaction composition comprises four different types of labeled nucleotides. In some embodiments, the nucleic acid sequencing reaction composition comprises a first labeled nucleotide comprising guanine, a second labeled nucleotide comprising cytosine, a third labeled nucleotide comprising adenine, and a fourth labeled nucleotide comprising thymine or uracil.

In some aspects, provided herein are methods of determining a sequence of a template nucleic acid. In some embodiments, the methods comprise exposing a complex in a target volume, the complex comprising the template nucleic acid, a primer, and a polymerizing enzyme, to a nucleic acid sequencing reaction composition according to the present application. In some embodiments, the methods further comprise directing a series of pulses of one or more excitation energies towards a vicinity of the target volume. In some embodiments, the methods further comprise detecting a plurality of emitted photons from luminescently labeled nucleotides during sequential incorporation into a nucleic acid comprising the primer. In some embodiments, the methods further comprise identifying the sequence of incorporated nucleotides by determining timing and optionally luminescence intensity of the emitted photons.

In some aspects, provided herein is a kit for sequencing a template nucleic acid. In some embodiments, the kit comprises two or more different types of labeled nucleotides. In some embodiments, at least one of the two or more different types of labeled nucleotides comprises a labeled nucleotide according to the present application.

In some aspects, the application provides compounds Formula (II):

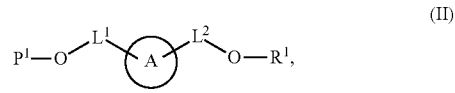

(II)

or a salt thereof, wherein: A is a polycyclic fluorophore; $L^1$ and $L^2$ are independently linkers selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, optionally substituted heteroarylene, and combinations thereof; $P^1$ is an oxygen protecting group; and $R^1$ is a reactive moiety. In some aspects, provided herein are compositions comprising a compound of Formula (II).

In some aspects, provided herein is a method for preparing a labeled biomolecule of the present application. In some embodiments, the method comprises (i) contacting a monomeric or oligomeric biomolecule of formula $Q^2$-OH, or a salt thereof, with a compound of Formula (II), or a salt thereof, under conditions sufficient to promote conjugation to yield a conjugate of the formula

In some embodiments, the method further comprises (ii) deprotecting the conjugate formed in step (i) under conditions sufficient to cleave the $P^1$ protecting group and yield a conjugate of the formula:

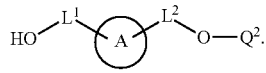

In some embodiments, the method further comprises (iii) contacting the conjugate formed in step (ii) with a monomeric or oligomeric biomolecule of formula $Q^1$-O—$R^1$, or a salt thereof, under conditions sufficient to promote conjugation to yield a labeled biomolecule of Formula (I).

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

The accompanying drawings, which constitute a part of this specification, illustrate several embodiments of the invention and together with the description, serve to explain the principles of the invention.

FIGS. 1A-1G show various examples of labeled biomolecules in accordance with the application. FIG. 1A shows a labeled biomolecule having one internal label. FIG. 1B shows a labeled biomolecule having two internal labels. FIG. 1C shows a circularized labeled biomolecule. FIG. 1D shows a labeled oligonucleotide that comprises an internally-labeled strand hybridized to an unlabeled strand. FIG. 1E shows a labeled oligonucleotide that comprises one internally-labeled strand hybridized to another internally-labeled strand. FIG. 1F shows a labeled oligonucleotide that comprises an unlabeled strand hybridized to a labeled strand having two internal labels. FIG. 1G shows a labeled oligonucleotide strand that is self-hybridized to form a stem-loop motif.

FIGS. 2A-2C depict examples of uses of labeled biomolecules in accordance with the application. FIG. 2A depicts an internally-labeled oligonucleotide hybridized to a target nucleic acid sequence. FIG. 2B depicts an internally-labeled biomolecule bound by a target protein. FIG. 2C depicts an internally-labeled antibody bound to a target protein.

FIGS. 3A-3B illustrate examples of labeled biomolecules modified with functional moieties in accordance with the application. FIG. 3A depicts an internally-labeled oligo-nucleotide modified with a quenching moiety that prevents detection of an internal label unless cleaved from the biomolecule. FIG. 3B depicts an internally-labeled biomolecule modified with a ligand that is bound by a target protein, where binding of the ligand to the target protein permits detection of an internal label.

FIGS. 4A-4C depict examples of labeled nucleotides bound by a polymerizing enzyme in accordance with the application. FIG. 4A depicts a polymerizing enzyme bound to a nucleotide that comprises an external label. FIG. 4B depicts a polymerizing enzyme bound to a nucleotide that comprises an internally-labeled biomolecule. FIG. 4C depicts a polymerizing enzyme bound to a nucleotide that comprises an internally-labeled oligonucleotide.

FIG. 5A generically depicts a set of externally-labeled and internally-labeled nucleotides that were prepared and subjected to further analysis. FIG. 5B shows the results of a single-molecule sequencing reaction that was performed using externally-labeled and internally-labeled nucleotides.

DETAILED DESCRIPTION OF CERTAIN EMBODIMENTS

Figure 5A:
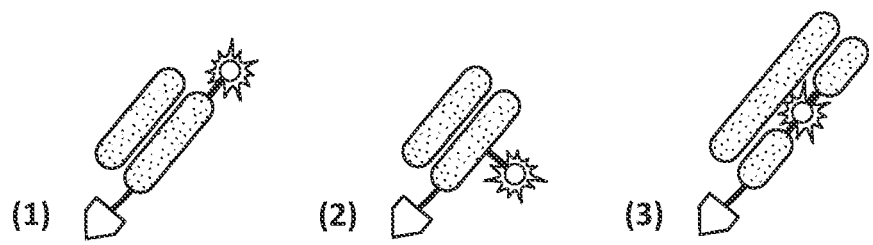
FIGS. 5A-5B show a comparative sequencing analysis of externally-labeled biomolecules and an internally-labeled biomolecule in accordance with the application.

Among other aspects, the disclosure provides labeled biomolecules comprising internally-conjugated luminescent labels (e.g., internal labels). In some embodiments, an internal label is configured with enhanced conformational restraint to restrict rotation and block deactivation pathways that shorten luminescence lifetime. In some embodiments, a labeled biomolecule is configured to provide a rigid molecular scaffold for the internal label that avoids label-label interactions and other quenching effects which could reduce luminescence intensity or other emission characteristics.

Without wishing to be bound by any particular theory, labeled biomolecules provided herein offer a number of distinct advantages, such as improved quantum yields and extended luminescence lifetimes, increased luminescence intensity and/or brightness, and decreased exposure to bulk solvent molecules to limit formation of reactive species. Accordingly, in some embodiments, provided herein are labeled biomolecules and methods of use. In some embodiments, the disclosure provides compositions and methods related to the preparation of labeled biomolecules. In some embodiments, the disclosure provides compositions and methods related to the preparation of biconjugatable labels.

Internally-Labeled Biomolecules

One aspect of the present invention relates to internally-labeled biomolecules ("labeled biomolecules"). As described herein, the labeled biomolecules (e.g., oligonucleotides, nucleic acids, polypeptides, proteins, polysaccharides) comprise internally-conjugated luminescent compounds ("luminescent labels" or "labels", e.g., polycyclic fluorophores). "Internally-labeled" or "internally-conjugated" are used interchangeably herein and refer to when one portion of the biomolecule is conjugated to a first site on the luminescent compound, and another portion of the biomolecule is conjugated to a second site on the luminescent compound. Internal conjugation of luminescent compounds can have several advantages. For example, internal conjugation of a label into a biomolecule can alter the lifetime and other photophysical properties of the label (e.g., via restricted rotation of the label). As another example, internal conjugation of a label can immobilize the label, separating it from other labels so as to mitigate self-quenching. Further, internal conjugation of a label can limit the label's access to bulk solvents in solution so as to mitigate radical formation which may be damaging to other components in the solution. Internal incorporation of labels have other advantages as described herein. A non-limiting set of examples of labeled biomolecules is shown in FIGS. 1A-1G.

FIGS. 1A-1G generically depict various configurations of labeled biomolecules in accordance with the present application. Each example is shown as having an internal label and a biomolecule (shown as stippled shapes). FIG. 1A is a labeled biomolecule comprising one internal label that conjugates one portion of a biomolecule to another portion of the biomolecule. In some embodiments, a labeled biomolecule comprises two or more internal labels.

FIG. 1B is a labeled biomolecule comprising two internal labels. As shown, one label conjugates a first portion of a biomolecule to a second portion of the biomolecule, and another label conjugates the second portion of the biomolecule to a third portion of the biomolecule. In some embodiments, labeled biomolecules having two or more copies of the same internal label exhibit increased luminescence intensity and/or brightness relative to a labeled biomolecule having one copy of the internal label. In some embodiments, labeled biomolecules having two or more different types of internal labels provide two or more unique detectable signals. Examples of various configurations and uses of multiply-labeled biomolecules are described elsewhere herein.

In accordance with the application, increased rigidity of internally-conjugated labels has been shown to enhance one or more luminescent properties of labeled biomolecules, e.g., via conformational restraint provided by a polycyclic fluorophore of the internal label. Advantageously, a biomolecular scaffold upon which an internal label is conjugated can be engineered to further promote rigidity and further enhance the one or more luminescent properties in these systems.

FIG. 1C is a labeled biomolecule comprising an internal label conjugated to a circularized biomolecule. As depicted by this example, in some embodiments, an internal label conjugates one end of a biomolecule to another end of the biomolecule such that the labeled biomolecule is circularized. Without wishing to be bound by any particular theory, it is thought that circularization promotes structural rigidity throughout the backbone of a biomolecule, which enhances the favorable luminescent properties of internal labels provided herein. Examples of circular biomolecules include, without limitation, cyclic peptides, cyclic proteins, and circular nucleic acids (e.g., circular RNA, DNA plasmids).

The inventors have further recognized and appreciated that oligonucleotides (e.g., polynucleotides, nucleic acids) provide rigid, highly tunable biomolecular scaffolds for internal labels of the application. Various examples of internally-labeled oligonucleotides are shown in FIGS. 1D-1G. These example constructs and additional embodiments related to internally-labeled oligonucleotides are described in detail elsewhere herein.

As generally illustrated in the example structures shown in FIGS. 1A-1G, in some embodiments, internal label 100 corresponds to A of Formula (I), as depicted herein. In some embodiments, a biomolecule (shown as stippled shapes) of the example structures corresponds to $Q^1$ and/or $Q^2$ of Formula (I), as depicted herein. In some embodiments, internal label 100 corresponds to A and a biomolecule (shown as stippled shapes) of the example structures corresponds to $Q^1$ and $Q^2$ of Formula (I), as depicted herein.

In one aspect, provided herein are labeled biomolecules of Formula (I):

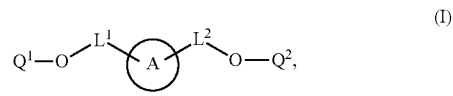

(I)

wherein:

$Q^1$ and $Q^2$ are independently monomeric or oligomeric biomolecules;

A is a polycyclic fluorophore; and $L^1$ and $L^2$ are independently linkers selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, optionally substituted heteroarylene, and combinations thereof.

As described herein,

(also depicted herein as "A") is a luminescent compound or dye. As represented by Formula (I), A is conjugated to one portion of a biomolecule (group $Q^1$) through a linker represented by $L^1$, and is conjugated to another portion of the biomolecule (group $Q^1$) through linker $L^1$. $Q^1$ and $Q^2$ together form a biomolecule, which is interrupted by a structure: —O-$L^1$-A-$L^2$-O—, and is thereby internally labeled.

In certain embodiments, A is a polycyclic fluorophore. In certain embodiments, incorporating a polycyclic fluorophore is advantageous insofar as the polycyclic structure can impart greater rigidity to the system as compared with linear or non-polycyclic fluorophores.

In certain embodiments, $L^1$ and $L^2$ are directly linked (e.g., through a covalent bonds) to one or more rings (e.g., benzenoid or heteroaromatic rings) of the polycyclic structure. This direct linkage can also impart greater rigidity to the system (e.g., via immobilization/restricted rotation of the label). In certain embodiments, $L^1$ and $L^2$ are directly linked to different rings on A, a design feature which can also impart greater rigidity to the system and/or help immobilize the dye.

In certain embodiments, A is a polycyclic cyanine, fluorone, acridine, phenoxazine, coumarin, or boron-dipyrromethene (BODIPY) fluorophore. In certain embodiments, A is a porphyrin, phthalocyanine, or naphthalimide. These are non-limiting examples. In certain embodiments, A is a polycyclic cyanine fluorophore. In certain embodiments, A is a polycyclic fluorone fluorophore. In certain embodiments, A is a polycyclic acridine fluorophore. In certain embodiments, A is a polycyclic phenoxazine fluorophore. In certain embodiments, A is a polycyclic coumarin fluorophore. In certain embodiments, A is a polycyclic BODIPY fluorophore. In certain embodiments, A is a porphyrin. In certain embodiments, A is a phthalocyanine. In certain embodiments, A is a naphthalimide. Other embodiments of Ring A are described below and herein.

In certain embodiments, A is a polycyclic cyanine fluorophore. In certain embodiments, A is an optionally substituted Cy3B dye. In certain embodiments, A is Cy3B. In certain embodiments, A is of the following formula:

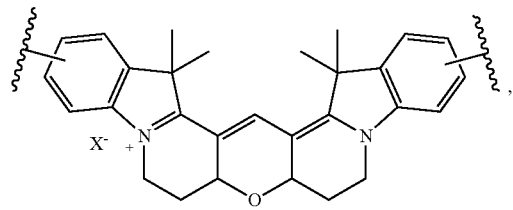

wherein $X^-$ is a counterion or is absent; and wherein the structure is optionally substituted at any position. In certain embodiments, the structure is unsubstituted.

In certain embodiments, A is of the following formula:

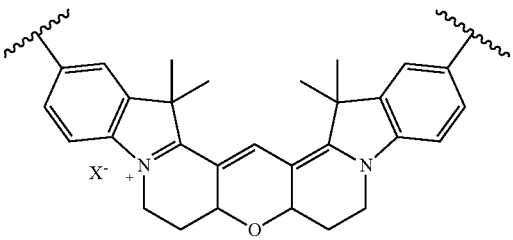

wherein $X^-$ is a counterion or is absent; and wherein the structure is optionally substituted at any position. In certain embodiments, the structure is unsubstituted.

Accordingly, in certain embodiments, the labeled biomolecule is of the formula

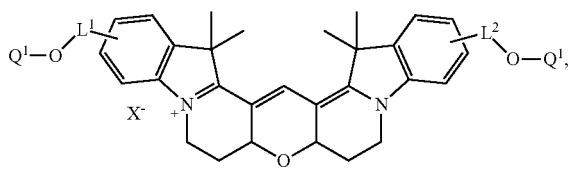

wherein $X^-$ is a counterion or is absent.

In certain embodiments, the labeled biomolecule is of the formula:

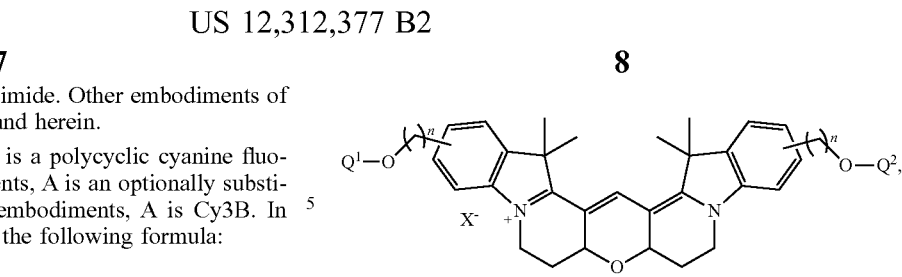

wherein n is independently an integer from 1-20, inclusive.

In certain embodiments, the labeled biomolecule is of the formula:

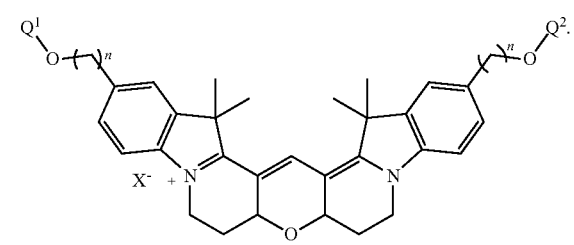

In certain embodiments, the labeled biomolecule is of the formula:

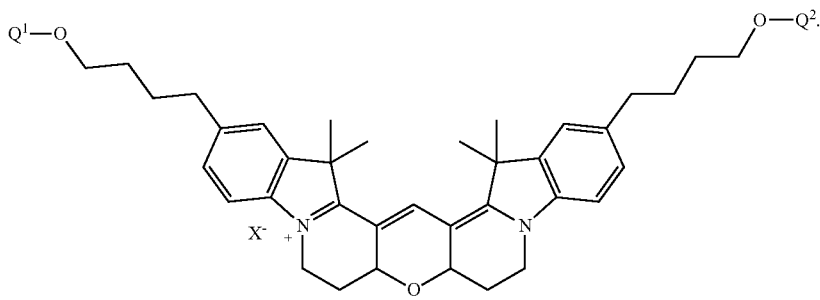

As described herein, in certain embodiments, Ring A is a polycyclic fluorone fluorophore (e.g., fluorescein or rhodamine). In certain embodiments, A is a fluorone dye. In certain embodiments, A is a rhodamine dye. In certain embodiments, A is of the following formula:

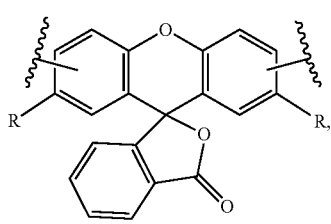

wherein each R is independently hydrogen, halogen, —N₃, —CN, —NO₂, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^O$, —SR$^S$, or —N(R$^N$)₂. In certain embodiments, the structure is optionally substituted at any position. In certain embodiments, the structure is unsubstituted.

As defined herein, each R is independently hydrogen, halogen, —N₃, —CN, —NO₂, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^O$, —SR$^S$, or —N(R$^N$)₂. In certain embodiments, R is hydrogen. In certain embodiments, R is halogen. In certain embodiments, R is —N₃. In certain embodiments, R is —CN. In certain embodiments, R is —NO₂. In certain embodiments. R is optionally substituted alkyl. In certain embodiments, R is optionally substituted alkenyl. In certain embodiments, R is optionally substituted alkynyl. In certain embodiments, R is optionally substituted carbocyclyl. In certain embodiments, R is optionally substituted aryl. In certain embodiments, R is optionally substituted heterocyclyl. In certain embodiments, R is optionally substituted heteroaryl. In certain embodiments, R is —OR$^O$. In certain embodiments, R is —SR$^S$. In certain embodiments, R is —N(R$^N$)₂. In certain embodiments, R is optionally substituted $C_{1-6}$ alkyl. In certain embodiments, R is unsubstituted $C_{1-6}$ alkyl. In certain embodiments, R is optionally substituted $C_{1-3}$ alkyl. In certain embodiments, R is unsubstituted $C_{1-3}$ alkyl. In certain embodiments, R is selected from the group consisting of methyl, ethyl, n-propyl, iso-propyl, n-butyl, iso-butyl, sec-butyl, and tert-butyl. In certain embodiments, R is methyl. In certain embodiments, each R is methyl.

In certain embodiments, A is of the formula:

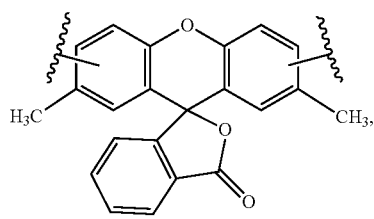

wherein the structure is optionally substituted at any position. In certain embodiments, the structure is unsubstituted.

In certain embodiments, A is of the formula:

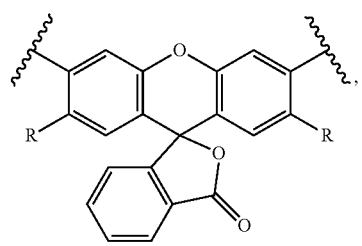

wherein the structure is optionally substituted at any position. In certain embodiments, the structure is unsubstituted.

In certain embodiments, A is of the formula:

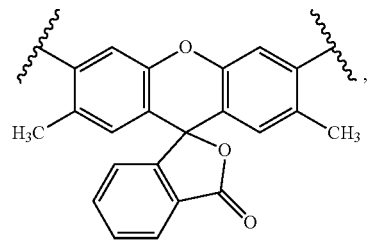 [SMILES: *c1cc2c(cc1C)C1(OC(=O)c3ccccc31)c1cc(C)c(*)cc1O2]

wherein the structure is optionally substituted at any position. In certain embodiments, the structure is unsubstituted.

Accordingly, in certain embodiments, the labeled biomolecule is of the formula:

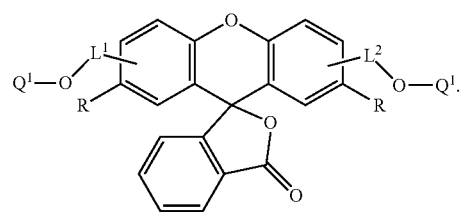

In certain embodiments, the labeled biomolecule is of the formula:

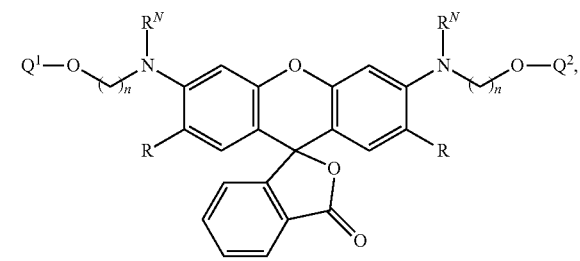

wherein:
n is independently an integer from 1-20, inclusive; and
each instance of R$^N$ is independently hydrogen, optionally substituted alkyl, optionally substituted alkenyl, optionally substituted alkynyl, optionally substituted carbocyclyl optionally substituted heterocyclyl, optionally substituted aryl, optionally substituted heteroaryl, optionally substituted acyl, or a nitrogen protecting group.

In certain embodiments, the labeled biomolecule is of the formula:

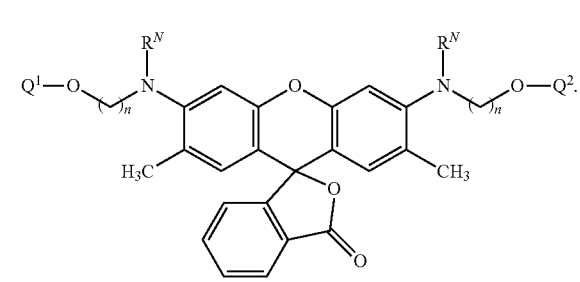

In certain embodiments, the labeled biomolecule is of the formula:

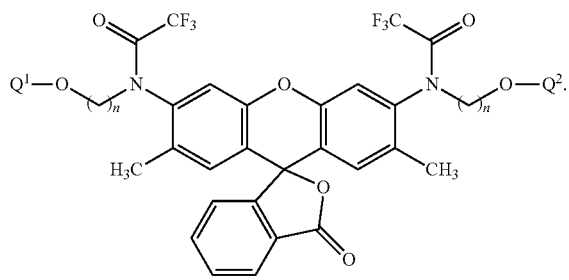

In certain embodiments, the labeled biomolecule is of the formula:

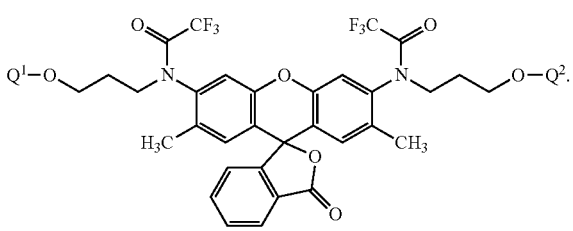

As described herein, in certain embodiments, A is a boron-dipyrromethene (BODIPY) fluorophore. In certain embodiments, A is of the following formula:

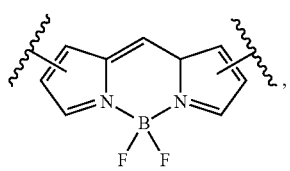

wherein the structure is optionally substituted at any position.

In certain embodiments, A is of the formula:

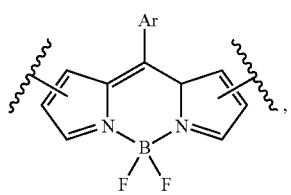

wherein Ar is optionally substituted aryl or optionally substituted heteroaryl; and wherein the structure is optionally substituted at any position.

As defined herein, Ar is optionally substituted aryl or optionally substituted heteroaryl. In certain embodiments, Ar is optionally substituted aryl. In certain embodiments, Ar is optionally substituted heteroaryl. In certain embodiments, Ar is optionally substituted phenyl. In certain embodiments, A is polyfluorophenyl. In certain embodiments, Ar is of the formula:

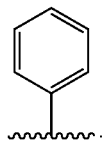

In certain embodiments, Ar is of the formula

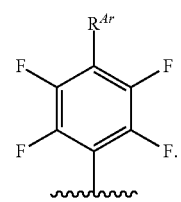

In certain embodiments, Ar is of the formula

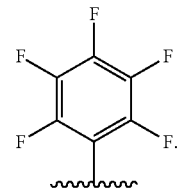

In certain embodiments, Ar is of the formula:

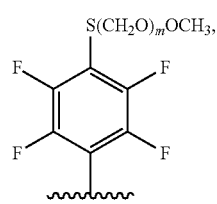

wherein m is as defined herein.

As defined herein, $R^{Ar}$ is hydrogen, halogen, —$N_3$, —CN, —$NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^O$, —$SR^S$, or —$N(R^N)_2$. In certain embodiments, $R^{Ar}$ is hydrogen. In certain embodiments, $R^{Ar}$ is halogen (—Cl, —I, —Br, —F). In certain embodiments, $R^{Ar}$ is —$N_3$. In certain embodiments, $R^{Ar}$ is —CN. In certain embodiments, $R^{Ar}$ is —$NO_2$. In certain embodiments. $R^{Ar}$ is optionally substituted alkyl. In certain embodiments, $R^{Ar}$ is optionally substituted alkenyl. In certain embodiments, $R^{Ar}$ is optionally substituted alkynyl. In certain embodiments, $R^{Ar}$ is optionally substituted carbocyclyl. In certain embodiments, $R^{Ar}$ is optionally substituted aryl. In certain embodiments, $R^{Ar}$ is optionally substituted heterocyclyl. In certain embodiments, $R^{Ar}$ is optionally substituted heteroaryl. In certain embodiments, $R^{Ar}$ is —$OR^O$. In certain embodiments, $R^{Ar}$ is —$SR^S$. In certain embodiments, $R^1$ is or —$N(R^N)_2$. In certain embodiments, $R^{Ar}$ is —F. In certain embodiments, $R^{Ar}$ is —$S(CH_2CH_2O)_mOCH_3$, wherein m is as defined herein.

As defined herein, m is an integer from 1-6, inclusive.

In certain embodiments, A is of the formula:

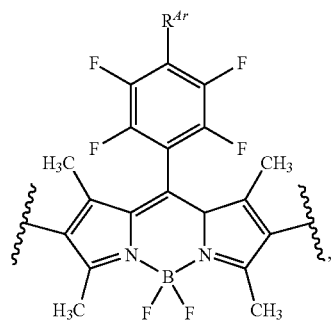

wherein $R^{Ar}$ is hydrogen, halogen, —$N_3$, —CN, —$NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^O$, —$SR^S$, or —$N(R^N)_2$. In certain embodiments, the structure is substituted at any position. In certain embodiments, the structure is unsubstituted.

Accordingly, in certain embodiments, the labeled biomolecule is of the formula:

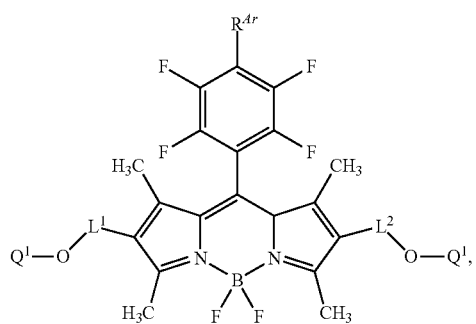

wherein $R^{Ar}$ is hydrogen, halogen, —$N_3$, —CN, —$NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^O$, —$SR^S$, or $N(R^N)_2$.

In certain embodiments, the labeled biomolecule is of the formula:

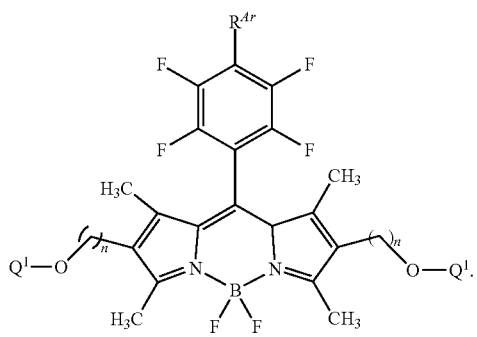

In certain embodiments, the labeled biomolecule is of one of the following formulae:

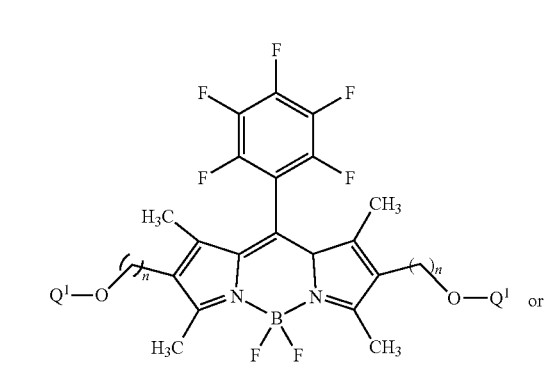

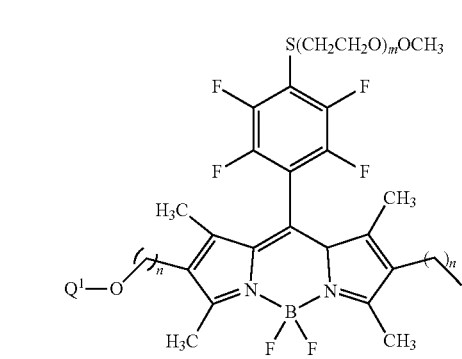

In certain embodiments, the labeled biomolecule is of the formula:

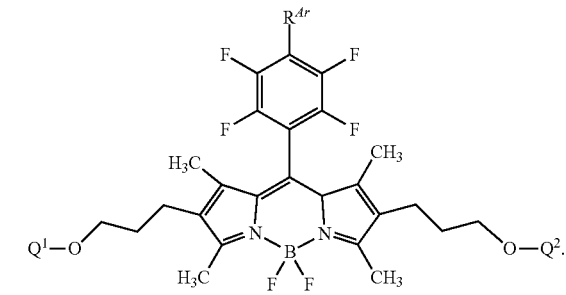

In certain embodiments, the labeled biomolecule is of one of the following formulae:

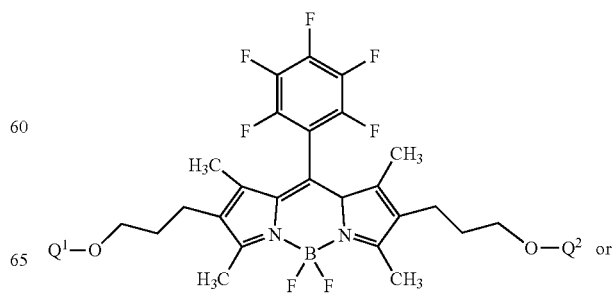

-continued

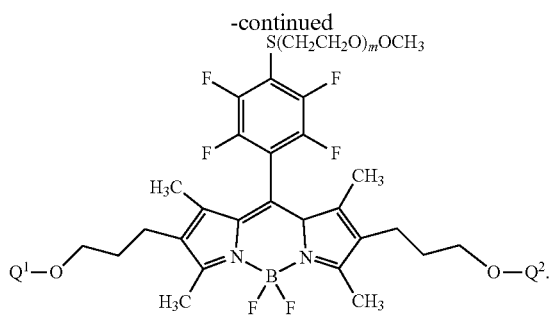

As described herein, in certain embodiments A is an acridine fluorophore. In certain embodiments, A is an acridine fluorophore of the following formula

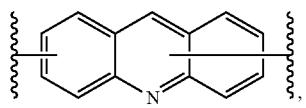

wherein the structure is optionally substituted.

As described herein, in certain embodiments A is a phenoxazine fluorophore. In certain embodiments, A is a phenoxazine fluorophore of the following formula:

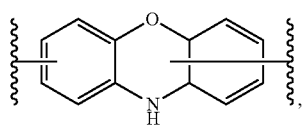

wherein the structure is optionally substituted.

As described herein, in certain embodiments A is a coumarin fluorophore. In certain embodiments, A is a coumarin fluorophore of the following formula:

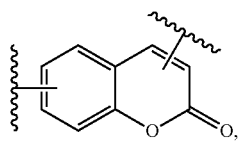

wherein the structure is optionally substituted. In certain embodiments, A is a coumarin fluorophore of the following formula

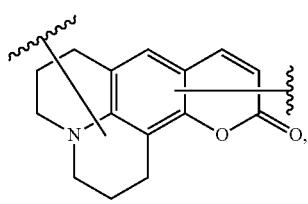

wherein the structure is optionally substituted.

As defined herein, $L^1$ and $L^2$ are independently linkers selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, optionally substituted heteroarylene, and combinations thereof. In certain embodiments, $L^1$ comprises optionally substituted alkylene. In certain embodiments, $L^1$ comprises optionally substituted alkenylene. In certain embodiments, $L^1$ comprises optionally substituted alkynylene. In certain embodiments, $L^1$ comprises optionally substituted heteroalkylene. In certain embodiments, $L^1$ comprises optionally substituted heteroalkenylene. In certain embodiments, $L^1$ comprises optionally substituted heteroalkynylene. In certain embodiments, $L^1$ comprises optionally substituted carbocyclylene. In certain embodiments, $L^1$ comprises optionally substituted heterocyclylene. In certain embodiments, $L^1$ comprises optionally substituted arylene. In certain embodiments. $L^1$ comprises optionally substituted heteroarylene. In certain embodiments, $L^1$ is optionally substituted $C_{1-20}$ alkylene. In certain embodiments, $L^1$ is optionally substituted $C_{1-10}$ alkylene. In certain embodiments, $L^1$ is optionally substituted $C_{1-6}$ alkylene. In certain embodiments, $L^1$ is of the formula:

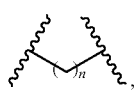

wherein n is as defined herein. In certain embodiments, $L^1$ is of the formula:

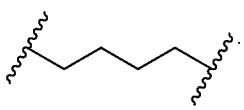 [SMILES: *CCCC*]

In certain embodiments, $L^1$ is of the formula:

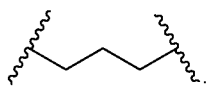 [SMILES: *CCC*]

In certain embodiments, $L^1$ is of the formula:

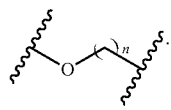

In certain embodiments, $L^1$ is of the formula:

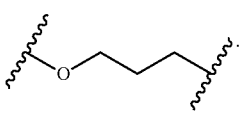

In certain embodiments, $L^1$ is of the formula:

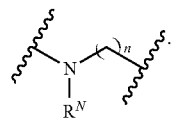

In certain embodiments, $L^1$ is of the formula:

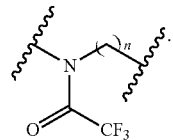

In certain embodiments, $L^1$ is of the formula:

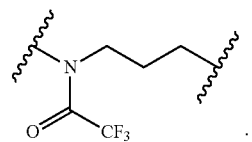

In certain embodiments, $L^1$ is of the formula:

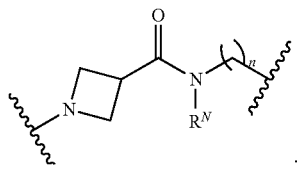

In certain embodiments. $L^1$ is of the formula:

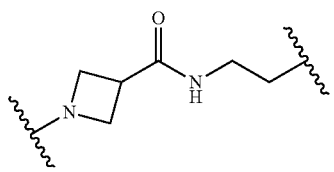

In certain embodiments, $L^1$ is of the formula:

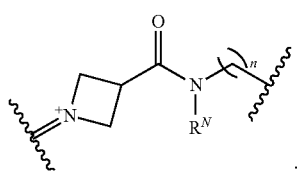

In certain embodiments, $L^1$ is of the formula:

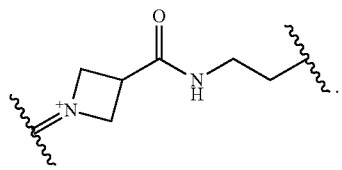 [SMILES: *CCNC(=O)C1C[N+](=*)C1]

In certain embodiments, $L^1$ is of the formula:

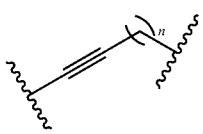

In certain embodiments, $L^2$ comprises optionally substituted alkylene. In certain embodiments, $L^2$ comprises optionally substituted alkenylene. In certain embodiments. $L^2$ comprises optionally substituted alkynylene. In certain embodiments, $L^2$ comprises optionally substituted heteroalkylene. In certain embodiments, $L^2$ comprises optionally substituted heteroalkenylene. In certain embodiments, $L^2$ comprises optionally substituted heteroalkynylene. In certain embodiments, $L^2$ comprises optionally substituted carbocyclylene. In certain embodiments, $L^2$ comprises optionally substituted heterocyclylene. In certain embodiments, $L^2$ comprises optionally substituted arylene. In certain embodiments, $L^2$ comprises optionally substituted heteroarylene. In certain embodiments, $L^2$ is optionally substituted $C_{1-20}$ alkylene. In certain embodiments, $L^2$ is optionally substituted $C_{1-10}$ alkylene. In certain embodiments $L^2$ is optionally substituted $C_{1-6}$ alkylene. In certain embodiments, $L^2$ is of the formula:

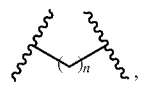

wherein n is as defined herein. In certain embodiments, $L^2$ is of the formula:

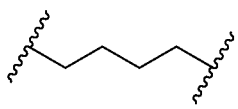

In certain embodiments, $L^2$ is of the formula:

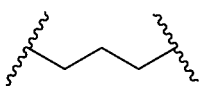

In certain embodiments, $L^2$ is of the formula:

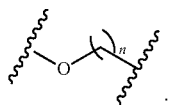

In certain embodiments, $L^2$ is of the formula:

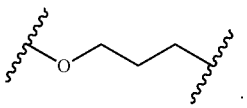

In certain embodiments, $L^2$ is of the formula:

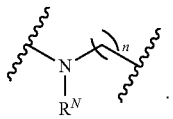

In certain embodiments. $L^2$ is of the formula:

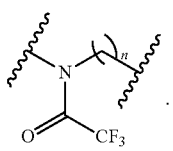

In certain embodiments. $L^2$ is of the formula:

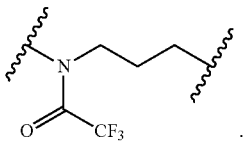

In certain embodiments, $L^2$ is of the formula:

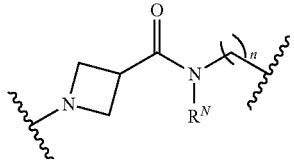

In certain embodiments, $L^2$ is of the formula:

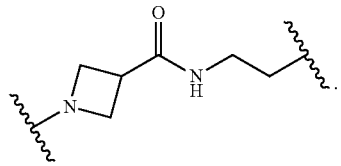 [SMILES: *CCNC(=O)C1CN(*)C1]

In certain embodiments, $L^2$ is of the formula:

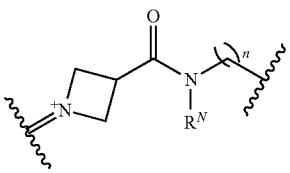

In certain embodiments, $L^2$ is of the formula:

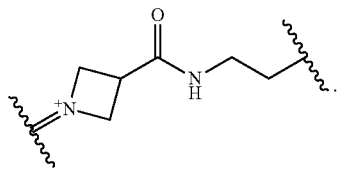 [SMILES: *CCNC(=O)C1C[N+](=*)C1]

In certain embodiments, $L^2$ is of the formula:

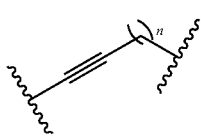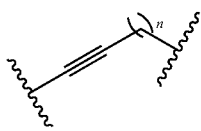

As defined herein, n is independently an integer from 1-20, inclusive. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8. In certain embodiments, n is 9. In certain embodiments, n is 10. In certain embodiments, n is 11. In certain embodiments, n is 12. In certain embodiments, n is 13. In certain embodiments, n is 14. In certain embodiments, n is 15. In certain embodiments, n is 16. In certain embodiments, n is 17. In certain embodiments, n is 18. In certain embodiments, n is 19. In certain embodiments, n is 20.

As described herein. $Q^1$ and $Q^2$ are independently monomeric or oligomeric biomolecules. As described herein, $Q^1$ and $Q^2$ together form an oligomeric or polymeric biomolecule, which is interrupted by $—O-L^1-A-L^2-O—$ and is thereby internally labeled (e.g., forming a labeled biomolecule).

In some embodiments, the labeled biomolecule is an oligomeric or polymeric biomolecule comprising at least 5 monomeric biomolecules (e.g., at least 5 nucleotides, at least 5 amino acids, at least 5 monosaccharides). In some embodiments, an oligomeric or polymeric biomolecule comprises at least 10 monomeric biomolecules. In some embodiments, an oligomeric or polymeric biomolecule comprises at least 10 and fewer than 200 monomeric biomolecules. For example, in some embodiments, an oligomeric or polymeric biomolecule comprises at least 10 and fewer than 150 monomeric biomolecules, at least 10 and fewer than 100 monomeric biomolecules, at least 10 and fewer than 50 monomeric biomolecules, at least 10 and fewer than 40 monomeric biomolecules, at least 10 and fewer than 30 monomeric biomolecules, or at least 10 and fewer than 20 monomeric biomolecules.

In certain embodiments, the labeled biomolecule is an oligonucleotide or nucleic acid.

In certain embodiments, $Q^1$ and $Q^2$ are independently nucleosides, nucleotides, oligonucleotides, nucleic acids, or derivatives or fragments thereof. In certain embodiments, $Q^1$ and $Q^2$ are independently nucleosides or derivatives or fragments thereof. In certain embodiments, $Q^1$ and $Q^2$ are independently nucleotides derivatives or fragments thereof. In certain embodiments, $Q^1$ and $Q^2$ are independently oligonucleotides or derivatives or fragments thereof. In certain embodiments, $Q^1$ and $Q^2$ are independently nucleic acids or derivatives or fragments thereof.

In certain embodiments, $Q^1$ and $Q^2$ are independently deoxyribonucleic acids, ribonucleic acids, peptide nucleic acids, locked nucleic acids, or derivatives or fragments thereof. In certain embodiments, $Q^1$ and $Q^2$ are independently deoxyribonucleic acids or derivatives or fragments thereof. In certain embodiments, $Q^1$ and $Q^2$ are independently ribonucleic acids or derivatives or fragments thereof. In certain embodiments, $Q^1$ and $Q^2$ are independently peptide nucleic acids or derivatives or fragments thereof. In certain embodiments. $Q^1$ and $Q^2$ are locked nucleic acids, or derivatives or fragments thereof.

As described herein, $Q^1$ and $Q^2$ together form an oligomeric or polymeric biomolecule, which is interrupted by —O-$L^1$-A-$L^2$-O— and is thereby internally labeled (e.g., forming a labeled biomolecule). In certain embodiments, the labeled biomolecule is a single-stranded nucleic acid. In this instance, the single-stranded nucleic acid comprises a first oligonucleotide strand ($Q^1$ and/or $Q^2$). In certain embodiments, the labeled biomolecule comprises a second oligonucleotide strand hybridized to the first oligonucleotide strand. For example, in certain embodiments, the second oligonucleotide strand is hybridized to $Q^1$ and/or $Q^2$. A visual representation of this internally-labeled system is represented below (wherein - - - - represents hybridization interactions (e.g., one or more Watson-Crick base interactions)):

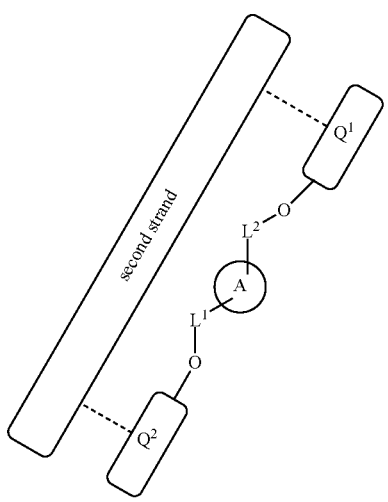

A visual representation of this system can also be found in FIG. 1D.

Additional examples of internally-labeled oligonucleotides are shown in FIGS. 1E-1G.

As illustrated by these and other examples described herein, various oligonucleotide strand hybridization strategies are provided to promote rigidity and/or shield an internal label from bulk solvent. Accordingly, oligonucleotide strand hybridization can be used as a general design strategy in preparing labeled oligonucleotides of the application. In some embodiments, oligonucleotide strand hybridization involves self-strand hybridization (e.g., self-hybridizing within a single strand). In some embodiments, oligonucleotide strand hybridization involves hybridization of different oligonucleotide strands.

FIG. 1D is a labeled oligonucleotide comprising an internally-labeled oligonucleotide strand hybridized to an unlabeled oligonucleotide strand. In some embodiments, an unlabeled oligonucleotide strand is used to increase rigidity in specific regions of a labeled oligonucleotide strand (e.g., in a region comprising an internal label). In some embodiments, an unlabeled oligonucleotide strand is hybridized to an internally-labeled oligonucleotide strand that comprises two or more internal labels provided herein.

FIG. 1E is a labeled oligonucleotide comprising one internally-labeled oligonucleotide strand hybridized to another internally-labeled oligonucleotide strand. In some embodiments, an internal label of one oligonucleotide strand comprises the same fluorophore as an internal label of the other oligonucleotide strand. In some embodiments, an internal label of one oligonucleotide strand comprises a different fluorophore from an internal label of the other oligonucleotide strand. In some embodiments, one of the internally-labeled oligonucleotide strands comprises two or more internal labels of the present application. In some embodiments, both of the internally-labeled oligonucleotide strands comprise two or more internal labels of the present application.

In some embodiments, oligonucleotide strand hybridization promotes formation of one or more structural motifs, such as stem-loops, junctions, pseudoknots, and double helices. Structural motifs, in accordance with the present application, are useful for enhancing rigidity of a labeled oligonucleotide and/or limiting the extent to which an internal label is exposed to bulk solvent. FIGS. 1F-1G depict examples of labeled oligonucleotides having higher order structural motifs formed through strand hybridization.

FIG. 1F is a labeled oligonucleotide comprising an unlabeled oligonucleotide strand hybridized to an oligonucleotide strand that comprises two internal labels. As generically shown in this example, formation of a double helix can promote separation of two internal labels of the same oligonucleotide strand. In some embodiments, hybridized oligonucleotide strands form a double helix having approximately 10 to 12 base pairs per turn.

Accordingly, in some embodiments, where two internal labels of the same oligonucleotide strand occupy approximately the same amount of space as one nucleotide within the strand, the internal labels are minimally separated by 5 to 6 nucleotides along the strand such that the labels are on approximately opposite sides of a double helix. In some embodiments, internal labels are separated by between 4 to 8 (e.g., 4, 5, 6, 7, or 8) nucleotides along the oligonucleotide strand. Without wishing to be bound by theory, such design strategies may be utilized to limit the extent of label-label interaction (e.g., quenching effects) due to the intervening helical structure absorbing any radiative and/or non-radiative decay.

Internal labels of the disclosure, in some embodiments, are integrated into the oligonucleotide backbone to minimize the extent of label-label interaction. Accordingly, in some embodiments, internal labels are separated by between 1 to 3 (e.g., 1, 2, or 3) or 9 to 13 (e.g., 9, 10, 11, 12, or 13) nucleotides along the same oligonucleotide strand. As illustrated by this example, labeled oligonucleotides may be designed by consideration of a predicted or known helical structure such that the relative location of one internal label to another through space can be manipulated to the desired application. Additional examples of structural motifs useful in the design of labeled oligonucleotides are known in the art and described herein.

FIG. 1G is an internally-labeled oligonucleotide strand that is self-hybridized to form a stem-loop motif. A stem-loop, or hairpin loop, is an unpaired loop of nucleotides on an oligonucleotide strand that is formed when the oligonucleotide strand folds and forms base pairs with another section of the same strand. In some embodiments, the unpaired loop of a stem-loop comprises three to ten nucleotides. Accordingly, a stem-loop can be formed by two regions of an oligonucleotide strand having reverse complementary sequences that hybridize to form a stem, where the two regions are separated by the three to ten nucleotides that form the unpaired loop. In some embodiments, the stem can be designed to have one or more G/C nucleotides, which can provide added stability with the additional hydrogen bonding interactions that form compared to A-T/U nucleotides. In some embodiments, the stem comprises G/C nucleotides immediately adjacent to an unpaired loop sequence. In some embodiments, the stem comprises G/C nucleotides within the first 2, 3, 4, or 5 nucleotides adjacent to an unpaired loop sequence.

As described herein, in some embodiments, an internal label conjugates one portion of an oligonucleotide strand to another portion of the oligonucleotide strand. As generally depicted in the example structures of FIGS. 1D-1G, in some embodiments, both portions of an oligonucleotide strand conjugated by an internal label are hybridized to the same oligonucleotide strand. Accordingly, an internal label can be adjacent to one or more (e.g., 1, 2, 3, 4, 5, or more) unpaired bases of a hybridized oligonucleotide strand.

In some embodiments, an internal label can interact with guanine nucleobases via radiative and/or non-radiative decay to effect diminished luminescence lifetime. In some embodiments, the one or more unpaired bases adjacent to an internal label are designed to exclude or minimize guanine. In some embodiments, regions surrounding an internally conjugated label are designed to exclude or minimize G/C content. In some embodiments, an internally-conjugated label is at least 2 nucleotides separated from a G or C nucleotide on the oligonucleotide strand (e.g., 2, 3, 4, 5, 6, 7, 8, 9, or more than 10 nucleotides separated from a G or C nucleotide). Thus, in some embodiments, each internal label is flanked on either side by at least 2 consecutive nucleotides selected from A or T/U.

The labels provided herein have applications in systems other than oligonucleotides and nucleic acids. In certain embodiments, the labeled biomolecule is a polypeptide or protein. For instance, in certain embodiments, $Q^1$ and $Q^2$ are independently amino acids, oligopeptides, polypeptides, proteins, or fragments thereof. In certain embodiments, $Q^1$ and $Q^2$ are independently amino acids. In certain embodiments, $Q^1$ and $Q^2$ are independently oligopeptides or fragments thereof. In certain embodiments, $Q^1$ and $Q^2$ are independently polypeptides or proteins, or fragments thereof. In certain embodiments, $Q^1$ and $Q^2$ are joined together to form a cyclic peptide or cyclic protein.

Non-limiting examples of oligopeptides and polypeptides peptides suitable for use in labeled biomolecules of the application include, without limitation, oligopeptides, cyclic peptides, and small proteins (e.g., avian pancreatic peptide-based miniature proteins, such as described in Hodges, A. M. and Schepartz, A. (2007) J. Am. Chem. Soc. 129:11024-11025). Methods of engineering structural constraints into polypeptides are well known in the art and are envisioned to be particularly useful, e.g., to impart rigidity and enhance one or more luminescent properties discussed herein. For example, proline content of a peptide amino acid sequence can be modified to control peptide shape and impart rigidity (see, e.g., Kritzer, J. A., et al. (2006) Chem Bio Chem 7:29-31). Additional non-limiting examples of useful peptide engineering techniques include peptide cyclization (see, e.g., Maltsev, O. V., et al. (2016) Angewandte Chemie 55(4): 1535-1539), α-helical peptide constraint via stapling and/or H-bond surrogates (see, e.g., Douse, C. H., et al. (2014) ACS Chem. Biol. 9:2204-2209), peptide constraint via cyclic β-sheet and β-hairpin mimics (see, e.g., Gibbs, A. C., et al. (1998) Nat. Struc. Biol. 5:284-288).

In certain embodiments, the labeled biomolecule is an oligosaccharide or a polysaccharide. For instance, in certain embodiments, $Q^1$ and $Q^2$ are independently monosaccharides, oligosaccharides, polysaccharides, or fragments thereof. In certain embodiments, $Q^1$ and $Q^2$ are independently monosaccharides. In certain embodiments, $Q^1$ and $Q^2$ are independently oligosaccharides or fragments thereof. In certain embodiments, $Q^1$ and $Q^2$ are independently polysaccharides or fragments thereof. Examples of oligosaccharides and polysaccharides suitable for use in labeled biomolecules of the application are known in the art (e.g., as described in Solid Support Oligosaccharide Synthesis and Combinatorial Carbohydrate Libraries, Wiley 2001).

In accordance with the application, labeled biomolecules provided herein comprise a biomolecule that functions as a rigid scaffold upon which an internal label of the application is incorporated. In some embodiments, the biomolecule comprises one or more features which confer additional functions useful in various methods of detection, quantitative analysis, and imaging. For example, FIGS. 2A-2C illustrate non-limiting examples of internally-labeled biomolecules comprising a biomolecule that interacts with a desired target molecule.

In some embodiments, a labeled biomolecule comprising an oligonucleotide can function as a hybridization probe. A hybridization probe is a labeled fragment of DNA or RNA (e.g., an oligonucleotide) that can be added to a sample of known or unknown content to detect the presence of a desired target nucleic acid that is complementary to the hybridization probe. For example, FIG. 2A depicts an internally-labeled hybridization probe 200 hybridized with a target nucleic acid 210. As generally illustrated by this example, internally-labeled hybridization probe 200 forms base pairing interactions with target nucleic acid 210 which results in a detectable increase in luminescence from the internal label. In some embodiments, however, hybridization of internally-labeled hybridization probe 200 with target nucleic acid 210 results in a detectable decrease in luminescence.

In some embodiments, an internally-labeled hybridization probe of the application comprises a sequence that is substantially complementary to a target nucleic acid sequence such that the probe and target form base pairing interactions under hybridization conditions. As described herein, an internal label conjugates one portion of a biomolecule to another portion of a biomolecule. Accordingly, one or both portions of the biomolecule (e.g., the oligonucleotide) conjugated by an internal label can be designed to hybridize with a target nucleic acid sequence. In some embodiments, a target nucleic acid comprises RNA (e.g., mRNA). In some embodiments, a target nucleic acid comprises DNA (e.g., cDNA, genomic DNA or fragments thereof).

Internally-labeled hybridization probes of the application can be utilized in any methodology known in the art which utilizes hybridization probes. Examples of such techniques include, without limitation, fluorescent in situ hybridization (FISH), Northern blotting, Southern blotting, and general techniques involving SNP detection, real-time nucleic acid detection, real-time PCR quantification, allelic discrimination and identification, multiplex PCR assays, and diagnostic clinical assays.

Labeled biomolecules of the application, in some embodiments, comprise a biomolecule that functions as a protein ligand. For example, FIG. 2B depicts a labeled biomolecule 201 bound by a target protein 211. As generally illustrated by this example, target protein 211 associates with (e.g., binds) at least a portion of the biomolecule (shown as dashed lines) of labeled biomolecule 201 which results in a detectable increase in luminescence from the internal label. In some embodiments, however, binding of target protein 211 to labeled biomolecule 201 results in a detectable decrease in luminescence.

In some embodiments, labeled biomolecule 201 and target protein 211 comprise a known binding pair. In some embodiments, labeled biomolecule 201 can be added to a sample of known or unknown content to detect presence of target protein 211. In some embodiments, target protein 211 is a receptor and labeled biomolecule 201 comprises a receptor ligand. In some embodiments, target protein 211 is an antibody specific for at least a portion of labeled biomolecule 201. In some embodiments, target protein 211 is an antibody and labeled biomolecule 201 comprises an antigen. In some embodiments, target protein 211 is a nucleic acid-binding protein (e.g., a DNA-binding protein) and labeled biomolecule 201 comprises a nucleic acid. Such labeled biomolecules are contemplated to be useful in methodologies that employ labeled protein ligands to detect presence of a target protein or to evaluate a protein-ligand binding interaction (e.g., fluorescence polarization and other techniques known in the art or described herein).

In some embodiments, a labeled biomolecule comprising a polypeptide can function as an antibody. FIG. 2C depicts an internally-labeled antibody 202 bound to a target protein 212. As generally illustrated by this example, internally-labeled antibody 202 comprises a Fab region configured to specifically bind target protein 212 which results in a detectable increase in luminescence from the internal label. In some embodiments, however, binding of internally-labeled antibody 202 with target protein 212 results in a detectable decrease in luminescence.

Internally-labeled antibodies of the application can be utilized in methods known in the art which utilizes luminescently labeled antibodies. Examples of such techniques include, without limitation, fluorescent in situ hybridization (FISH). Western blotting, general methodologies involving immunolabeling, such as immunocytochemistry and immunohistochemistry techniques, and other techniques known in the art or described herein.

As described above, an internal label of the application can be conjugated to a biomolecule that interacts with a desired target molecule. In some embodiments, an internal label is conjugated to a protein that associates with (e.g., binds to) a target ligand. In some embodiments, the protein is an antibody or an antigen-binding portion of an antibody. In some embodiments, the protein is an enzyme, such as a peptidase (e.g., an exopeptidase or an endopeptidase), a ribozyme, an aptazyme, a ligase, a transferase, or a tRNA synthetase. In some embodiments, an internal label is conjugated to a nucleic acid that associates with (e.g., binds to) a target ligand. In some embodiments, the nucleic acid is a nucleic acid aptamer (e.g., a DNA aptamer, an RNA aptamer, or a derivative or analog thereof).

In some embodiments, a labeled biomolecule comprises a biomolecule that is modified with one or more functional moieties. For example, FIGS. 3A-3B illustrate non-limiting examples of labeled biomolecules comprising moieties that interact with a target molecule and/or an internal label.

In accordance with the application, biomolecular scaffolds provide rigid labeling scaffolds which can be of particular benefit with techniques in which a strongly defined position of an internal label is desired. For example, Förster resonance energy transfer (FRET) and fluorescence correlation spectroscopy (FCS) have become important tools for the in vitro and in vivo investigation of conformational dynamics in biomolecules. These methods rely on the distance-dependent quenching of the fluorescence signal of a donor fluorophore either by a fluorescent acceptor fluorophore (FRET) or a non-fluorescent quencher, as used in FCS with photoinduced electron transfer (PET).

In some embodiments, a labeled biomolecule comprises one or more quenching moieties (e.g., fluorescent and/or non-fluorescent quenching moieties) that interact with an internal label of the labeled biomolecule. In some embodiments, such moieties can be useful in real-time PCR where an internal label's position is well defined in relation to a quencher that is cleaved by exonuclease activity. An example of this process is illustrated in FIG. 3A.

As shown in panel I, an internally-labeled hybridization probe comprising a quenching moiety 300 is hybridized with a target nucleic acid. In some embodiments, quenching moiety 300 is a non-fluorescent quencher that absorbs emission from an internal label. In some embodiments, quenching moiety 300 is a fluorescent quencher that absorbs emission of one wavelength from an internal label and emits at another wavelength.

As shown in panel II, quenching moiety 300 has been cleaved from the internally-labeled hybridization probe (e.g., by an exonuclease). This separation of quenching moiety 300 from the internal label eliminates the distance-dependent quenching effects to permit detection of a luminescence from the internal label. It should be appreciated that in some embodiments, an internally-labeled hybridization probe comprises an internal label that functions as a quencher of another label of the hybridization probe.

Quenching moiety-modified hybridization probes are known in the art and are contemplated to be useful with internal labels of the application. Examples of such hybridization probes include, without limitation, molecular beacons, TaqMan probes, Exciton-controlled hybridization-sensitive fluorescent oligonucleotide (ECHO) probes, and cycling probe technology (CPT) probes.

Accordingly, in some embodiments, multiple internal labels (e.g., two, three, four, five, or more internal labels) can be incorporated into a biomolecule according to the desired luminescent properties of a labeled biomolecule provided herein. For example, in some embodiments, a labeled biomolecule having two or more internal labels exhibits increased luminescence intensity and/or brightness relative to the biomolecule having one internal label. In some embodiments, the two or more internal labels are configured to provide independent reporter signals. In some embodiments, the two or more internal labels are configured to provide dependent reporter signals (e.g., a donor label and an acceptor label of a FRET pair).

In some aspects, the application provides internal labels configured for use in conventional solid-phase synthesis techniques, e.g., phosphoramidite analogs useful in oligonucleotide synthesis. Accordingly, in some embodiments, labels provided herein can be readily incorporated into a biomolecule to generate a labeled biomolecule having a number of internal labels that may be limited only by the desired size of the biomolecule. For example, in some embodiments, a labeled biomolecule comprises two or more (e.g., 2, 3, 4, 5, 6, 7, 8, 9, 10, or more) internal labels. In some embodiments, a labeled biomolecule comprises between 2 and 5, between 2 and 10, between 5 and 10, between 5 and 15, between 10 and 15, between 15 and 20, or more internal labels.

In some embodiments, a labeled biomolecule provided herein further comprises one or more luminescent labels other than the polycyclic fluorophore of Formula (I). For example, in some embodiments, a labeled biomolecule comprises at least one internal label according to Formula (I), and one or more internal labels comprising a linear or non-polycyclic fluorophore. In some embodiments, a labeled biomolecule comprises at least one internal label according to Formula (I), and one or more external labels.

In some embodiments, an external label refers to a label (e.g., a fluorophore) conjugated to a single site of a labeled biomolecule provided herein. In some embodiments, an external label is conjugated to a labeled biomolecule at a terminal end. For example, in some embodiments, an external label is conjugated to a 5' or 3' end of a labeled oligonucleotide. In some embodiments, an external label is conjugated to an N- or C-terminus of a labeled polypeptide. In some embodiments, an external label is conjugated to a labeled biomolecule at a terminal monomer of the biomolecule (e.g., conjugated to a base of a terminal nucleotide in an oligonucleotide strand, conjugated to a side chain of a terminal amino acid in a polypeptide strand).

In some embodiments, an external label is conjugated to a labeled biomolecule at a non-terminal site of the biomolecule. In some embodiments, an external label is conjugated to a labeled biomolecule at a site that is between monomers of the biomolecule. In some embodiments, an external label is conjugated to an abasic site of a labeled oligonucleotide. In some embodiments, an external label is conjugated to a labeled biomolecule at a non-terminal monomer of the biomolecule (e.g., conjugated to a base of a non-terminal nucleotide in an oligonucleotide strand, conjugated to a side chain of a non-terminal amino acid in a polypeptide strand).

Labeled biomolecules of the application, in some embodiments, comprise a biomolecule modified with one or more moieties that function as protein ligands. For example, FIG. 3B illustrates a process whereby a labeled biomolecule comprising a ligand moiety is detectably bound by a target protein. As shown in panel I, a target protein is exposed to a labeled biomolecule comprising a ligand moiety 301 configured to bind the target protein. In the absence of binding between the target protein and ligand moiety 301, the internal label of the labeled biomolecule does not emit a detectable signal.

As shown in panel II, the target protein associates with (e.g., binds) ligand moiety 301 which results in a detectable increase in luminescence from the internal label. In some embodiments, however, binding of the target protein to ligand moiety 301 results in a detectable decrease in luminescence. In some embodiments, the change in detectable luminescence upon binding occurs as a result of confinement of the internal label biomolecule to an observation region (e.g., immobilization to a surface for a period of time sufficient to permit detection). In some embodiments, the change in luminescence upon binding occurs as a result of FRET interactions (e.g., with the target protein or a surface-conjugated acceptor/donor).

In some embodiments, labeled biomolecules comprising one or more ligand moieties can be used, e.g., for purposes of immobilizing a labeled biomolecule to a surface or a material, for detection of target protein in a known or unknown sample, for detection (e.g., quantitation) of a binding interaction between the target protein and a ligand moiety that is known or not known to bind the target protein.

In certain embodiments, the labeled biomolecule is associated with a reactant configured for use as a substrate in a reaction. For example, in certain embodiments, $Q^1$ and $Q^2$ of Formula (I) are independently optionally associated with a reactant configured for use as a substrate in a reaction. In the case of an oligonucleotide or nucleic acid system, for example, the first and second oligonucleotide strands are independently optionally associated with a reactant configured for use as a substrate in a reaction. In some embodiments, the reactant is configured for use as a substrate in a polymerization reaction. In some embodiments, the reactant is cleaved from the labeled biomolecule by a polymerase when subjected to polymerization reaction conditions. For example, in some embodiments, the reactant is a nucleotide (e.g., for use in a method of sequencing a nucleic acid).

Labeled Nucleotides

Also provided herein are labeled nucleotides comprising one or more nucleotides associated with a labeled biomolecule described herein. In some embodiments, the one or more nucleotides comprise one type of nucleotide selected from guanine, cytosine, adenine, and thymine or uracil. In some embodiments, the one or more nucleotides are cleaved from the labeled biomolecule by a polymerase when subjected to polymerization reaction conditions.

Without wishing to be bound by any particular theory, labeled nucleotides provided herein offer a number of distinct advantages over those currently used in sequencing reactions, such as increased readlength and increased accuracy, in addition to the advantages described elsewhere herein. FIGS. 4A-4C highlight several features of labeled nucleotides of the disclosure.

Each of FIGS. 4A-4C depicts a nucleotide 400 bound by a polymerase 410. Nucleotide 400 of FIG. 4A is externally-conjugated to a luminescent label, whereas nucleotides of FIGS. 4B and 4C are associated with different labeled biomolecules described herein. As illustrated in FIG. 4A, the externally-conjugated label is relatively proximal to the polymerase and has a relatively high degree of access to bulk solvent molecules. In some embodiments, such characteristics are adverse to a polymerization reaction. For example, in some embodiments, a shorter distance between a label and a polymerase can result in label-induced damage to the polymerase via radiative and/or non-radiative decay (shown as path (i)). In some embodiments, a higher degree of a label's access to bulk solvent molecules can result in a higher incidence of reactive oxygen species (ROS) formation. Once formed, ROS can damage the polymerase to adversely affect enzymatic activity (shown as path (ii)).

FIG. 4B depicts a nucleotide associated with a labeled biomolecule, such as a labeled oligonucleotide strand. As shown relative to the externally-conjugated label, the biomolecule increases separation between the label and the polymerase. Additionally, the portion of the biomolecule between the nucleotide and the internal label provides a protective barrier between the label and polymerase. Accordingly, the occurrence of label-induced damage to the polymerase can be decreased, due to the label-polymerase separation and/or due to the biomolecule absorbing any decay emitted from the label (shown as path (iii)).

Also as shown relative to FIG. 4A, integration of the internal dye into the biomolecule shown in FIG. 4B decreases the extent to which the label is exposed to bulk solvent molecules. Accordingly, ROS-induced damaged can be decreased due to lowered incidence of ROS formation as a result of decreased access of label to bulk solvent, and/or due to the biomolecule absorbing any ROS-induced damaged, and/or due to free radical decay over the label-polymerase separation distance (shown as path (iv)).

FIG. 4C depicts a nucleotide associate with a labeled oligonucleotide. As shown, the labeled oligonucleotide is hybridized with an unlabeled oligonucleotide strand. In accordance with the application, such constructs impart a high degree of rigidity that enhance each of the above advantages described for the labeled nucleotide of FIG. 4B.

For example, the hybridized strand provides increased rigidity, meaning less overall flexibility which further promotes label-polymerase separation. The hybridized strand also provides another barrier between the label and the polymerase that can absorb any label-induced decay (shown as path (v)). Additionally, ROS-induced damage is further decreased due to the hybridized strand further restricting access of the label to bulk solvent, and/or due to the hybridized strand absorbing any ROS-induced damage, and/or due to free radical decay over the increased label-polymerase separation distance.

Accordingly, in each of the above examples, the advantages provided by the labeled biomolecules of the application provide increased readlength in sequencing reactions by limiting the extent of photo-induced damage to the polymerase. Additionally, labeled nucleotides of the application provide increased accuracy, e.g., as a result of the enhancement of one or more emission characteristics.

It should be understood that, in the context of a labeled biomolecule, a "nucleotide" or "nucleoside polyphosphate" attached thereto refers to the one or more nucleotides (e.g., nucleoside polyphosphates) that are configured to be incorporated into a growing nucleic acid strand (e.g., during a sequencing reaction). In some embodiments, the one or more nucleotides comprise one or more nucleoside monophosphates or nucleoside polyphosphates. Examples of nucleoside polyphosphates include, in some embodiments, nucleoside di- or triphosphates, or nucleosides with more than three 5' phosphates, such as nucleoside hexaphosphates. In some embodiments of any of the compositions or methods described in this application, a phosphate portion (e.g., a polyphosphate portion) of a nucleotide includes one or more phosphates (e.g., 1, 2, 3, 4, 5, 6, 7, 8, 9, 10, or more phosphate groups) or variants thereof. For example, in some embodiments, a phosphate portion (e.g., a polyphosphate portion) of a nucleotide can include a phosphate ester, a thioester, a phosphoramidate, an alkyl phosphonate linkage, other suitable linkage, or more than one such modifications, or a combination of two or more thereof.

A labeled nucleotide can be a terminal phosphate labeled nucleotide, such that a labeled biomolecule of the application is attached to a terminal phosphate of the nucleotide. For example, in some embodiments, one or more nucleotides may be attached through a terminal phosphate to a biomolecule (e.g., $Q^1$ and/or $Q^1$ of Formula (I)) that forms part of a labeled biomolecule as described in this application. Accordingly, in some embodiments, a "labeled nucleotide" of the application refers to a nucleotide attached to a labeled biomolecule of Formula (I). In some embodiments, the one or more nucleotides may be attached through a terminal phosphate to an oligonucleotide (e.g., an unlabeled oligonucleotide strand) that forms part of a labeled biomolecule as described in this application.

A labeled biomolecule can be attached to a terminal phosphate of a nucleotide through a linker. The linker can include, for example, at least one or a plurality of hydroxyl groups, sulfhydryl groups, amino groups or haloalkyl groups, which may be suitable for forming, for example, a phosphate ester, a thioester, a phosphoramidate or an alkyl phosphonate linkage at the terminal phosphate of a natural or modified nucleotide. A linker can be cleavable so as to separate a label from the terminal phosphate, such as with the aid of a polymerization enzyme. Examples of nucleotides and linkers are provided in U.S. Pat. No. 7,041,812, which is entirely incorporated herein by reference. In some embodiments, the linker comprises optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, optionally substituted heteroarylene, and combinations thereof. Additional examples of linkers useful for attaching a label to a nucleotide can be found in co-pending U.S. patent application Ser. No. 15/600,979, the relevant portions of which are incorporated herein by reference in entirety.

A nucleotide (e.g., a nucleoside polyphosphate) can comprise any of an adenine (A), cytosine (C), guanine (G), thymine (T), and uracil (U), or variants thereof. A nucleotide (e.g., a nucleoside polyphosphate) can comprise a methylated nucleobase. For example, a methylated nucleotide can be a nucleotide that comprises one or more methyl groups attached to the nucleobase (e.g., attached directly to a ring of the nucleobase, attached to a substituent of a ring of the nucleobase). Exemplary methylated nucleobases include 1-methylthymine, I-methyluracil, 3-methyluracil, 3-methylcytosine, 5-methylcytosine, 1-methyladenine, 2-methyladenine, 7-methyladenine, N6-methyladenine, N6,N6-dimethyladenine, 1-methylguanine, 7-methylguanine, N2-methylguanine, and N2,N2-dimethylguanine.

The term "nucleic acid," as used herein, generally refers to a molecule comprising one or more nucleic acid subunits. A nucleic acid may include one or more subunits selected from adenine (A), cytosine (C), guanine (G), thymine (T), and uracil (U), or variants thereof. In some examples, a nucleic acid is deoxyribonucleic acid (DNA) or ribonucleic acid (RNA), or derivatives thereof. In some embodiments, the nucleic acid is a modified nucleic acid, including, without limitation, a locked nucleic acid (LNA), a peptide nucleic acid (PNA), a triazole-linked nucleic acid, a 2'-F-modified nucleic acid, and derivatives and analogs thereof. A nucleic acid may be single-stranded or double stranded. In some embodiments, a nucleic acid generally refers to any polymer of nucleotides.

Emission Characteristics

As described herein, internal conjugation of a label into a biomolecule can alter the photophysical properties of the label (e.g., via restricted rotation or immobilization of the label within the biomolecule). Therefore, in certain embodiments, one or more emission characteristics of the labeled biomolecule are altered (e.g., increased) relative to an unconjugated molecule comprising the label. The "unconjugated molecule" comprising the label, as described herein, does not comprise one or both of $Q^1$ and $Q^2$. The one or more emission characteristics that are altered by internal conjugation can include, but are not limited to, luminescence lifetime, luminescence intensity, brightness, emission maximum, luminescence quantum yield, and photostability.

In certain embodiments, luminescence lifetime of a labeled biomolecule is increased relative to the unconjugated molecule. In certain embodiments, the luminescence lifetime of the labeled biomolecule is increased by at least 10% relative to the unconjugated molecule. In certain embodiments, the luminescence lifetime of the labeled biomolecule is increased by between approximately 10% and 50% (e.g., between about 10% and 25%, between about 10%6 and 15%, between about 25% and 50%, between about 40% and 50%) relative to the unconjugated molecule. An example of increased luminescence lifetime is shown in FIGS. 5A-5B.

Figure 5B:
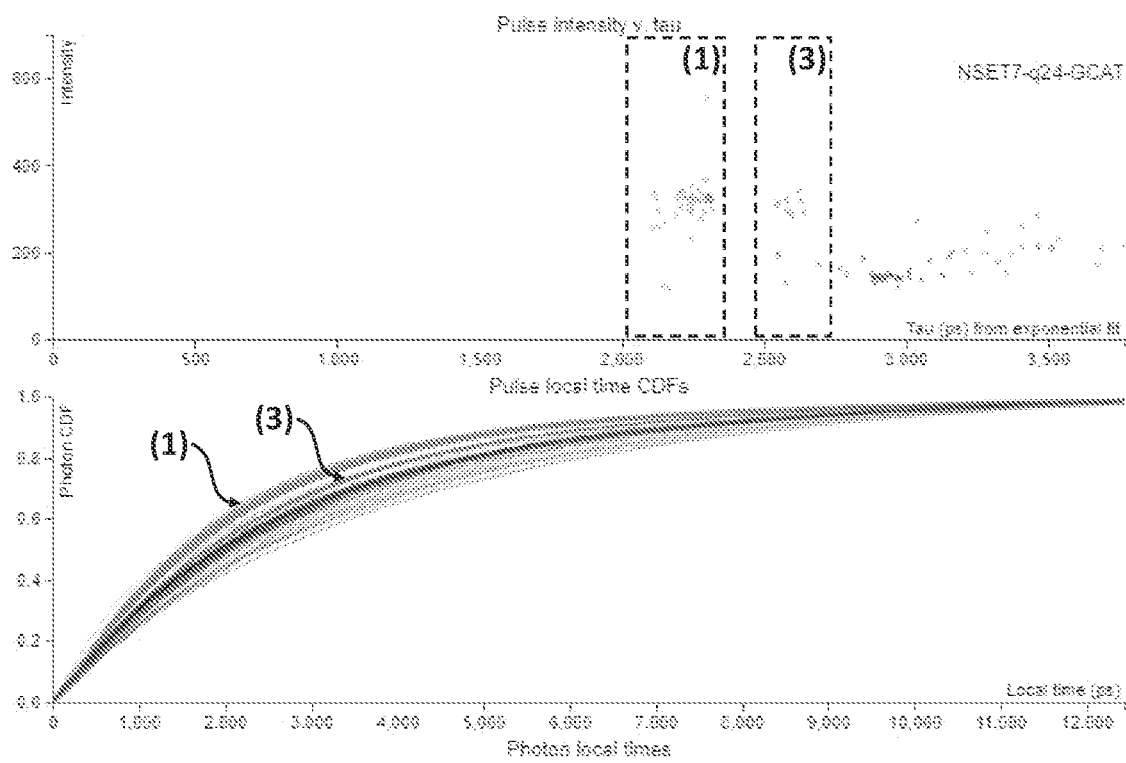

A set of labeled biomolecules comprising nucleotides were prepared in accordance with the constructs generically depicted in FIG. 5A. Labeled nucleotides (1) and (2) represent conjugates wherein a Cy3B dye was externally conjugated to a DNA linker at the terminus or a branch point, respectively, of the oligonucleotide. By contrast, labeled nucleotide (3) exchanges a base within the oligonucleotide strand for the Cy3B dye itself to become internally incorporated into the DNA backbone. These labeled nucleotides were used in sequencing experiments, and lifetime measurements for each conjugate were obtained. The externally conjugated Cy3B constructs (1) and (2) produced lifetimes of approximately 2.2 nanoseconds, whereas the measured lifetime for the internally conjugated Cy3B construct (3) was 2.6 nanoseconds—an increase in lifetime of approximately 15-20% for the internally conjugated dye.

In certain embodiments, luminescence intensity of a labeled biomolecule is increased relative to the unconjugated molecule. In certain embodiments, luminescence intensity of the labeled biomolecule is increased by between approximately 5% and 25% (e.g., between about 5% and 20%, between about 5% and 15%, between about 5% and 10%, between about 10% and 25%, between about 15% and 25%, between about 20% and 25%) relative to the unconjugated molecule. In some embodiments, luminescence intensity of the labeled biomolecule is increased by approximately 5%, approximately 10%, approximately 15%, approximately 20%, approximately 25%, or more relative to the unconjugated molecule.

In certain embodiments, brightness of a labeled biomolecule is increased relative to the unconjugated molecule. In certain embodiments, brightness of the labeled biomolecule is increased by between approximately 5% and 10% relative to the unconjugated molecule. In certain embodiments, brightness of the labeled biomolecule is increased by between approximately 5% and 25% (e.g., between about 5% and 20%, between about 5% and 15%, between about 5% and 10%, between about 10% and 25%, between about 15% and 25%, between about 20% and 25%) relative to the unconjugated molecule. In some embodiments, brightness of the labeled biomolecule is increased by approximately 5%, approximately 10%, approximately 15%, approximately 20%, approximately 25%, or more relative to the unconjugated molecule.

Figure 6:
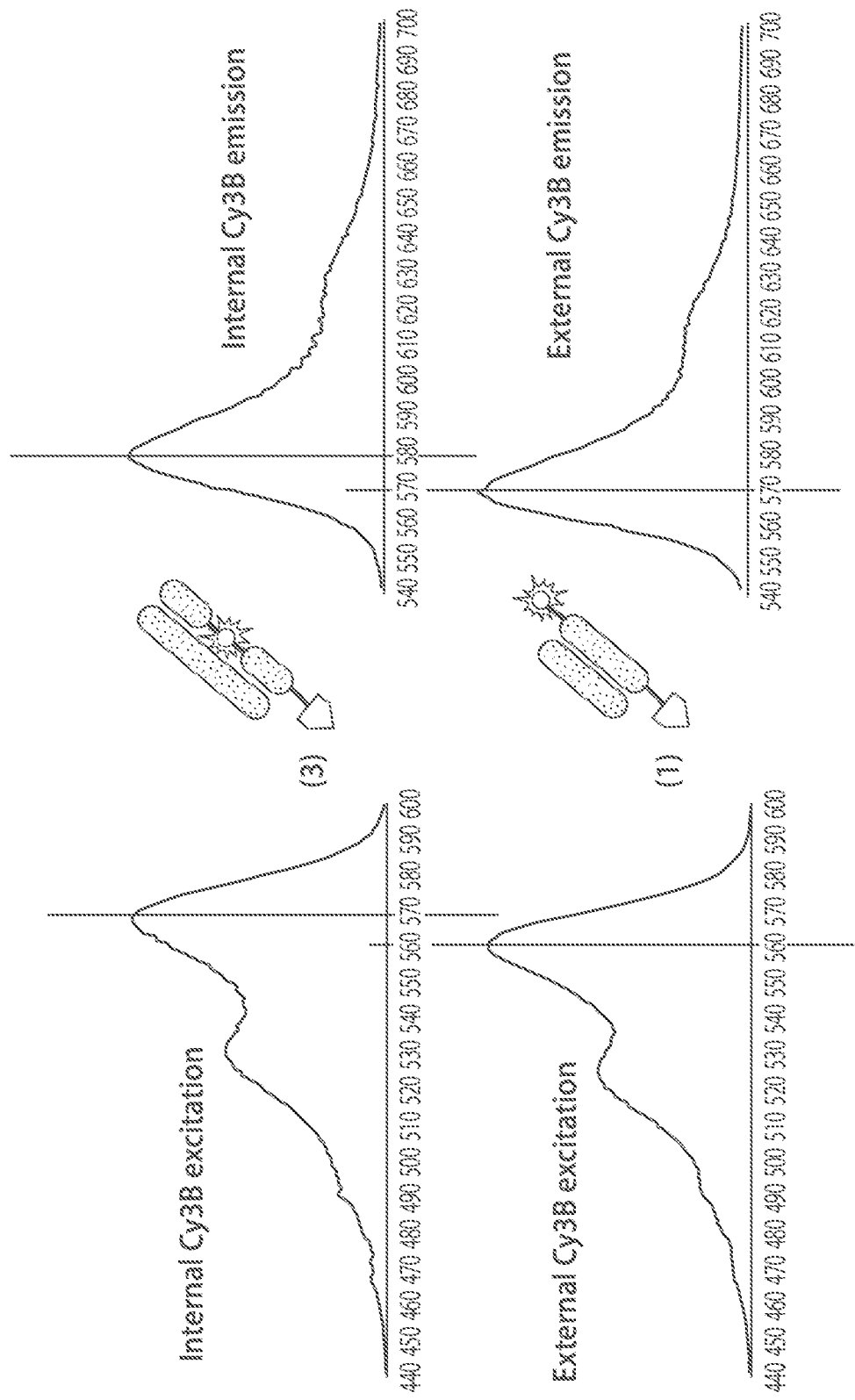
FIG. 6 shows an alignment of excitation and emission spectra for an externally-labeled and an internally-labeled nucleotide.

In certain embodiments, emission maximum of a labeled biomolecule is increased by at least 1% relative to the unconjugated molecule. In certain embodiments, emission maximum of the labeled biomolecule is increased by between approximately 1% and 10% (e.g., between about 1% and 5%, between about 5% and 10%) relative to the unconjugated molecule. An example of increased emission maximum is shown in FIG. 6. In some embodiments, emission maximum of the labeled biomolecule is increased by approximately 1%, approximately 2%, approximately 5%, approximately 10%, or more relative to the unconjugated molecule.

Bulk fluorescence data obtained for an internally-conjugated Cy3B and an externally-conjugated Cy3B are depicted in FIG. 6. As shown, the excitation spectrum of the internal dye is red-shifted by 8 nm relative to the external dye, which places the vibronic shoulder (the hump on the left of the trace) closer to 532 nm. Also as shown, the emission spectrum of the internal dye is red-shifted, which was found to advantageously increase detectable signals as more light was permitted past the filter.

In certain embodiments, luminescence quantum yield of a labeled biomolecule is increased relative to the unconjugated molecule. In certain embodiments, luminescence quantum yield of the labeled biomolecule is increased by between approximately 5% and 25% (e.g., between about 5% and 20%, between about 5% and 15%, between about 5% and 10%, between about 10% and 25%, between about 15% and 25%, between about 20% and 25%) relative to the unconjugated molecule. In some embodiments, luminescence quantum yield of the labeled biomolecule is increased by approximately 5%, approximately 10%, approximately 15%, approximately 20%, approximately 25%, or more relative to the unconjugated molecule.

In certain embodiments, photostability of a labeled biomolecule is increased relative to the unconjugated molecule. As used herein, in some embodiments, photostability refers to the ability of a luminescent molecule to continue to fluoresce over time. In some embodiments, photostability can be evaluated by measuring the rate of photobleaching. For example, in some embodiments, the rate of photobleaching can be measured for a labeled biomolecule (e.g., a biomolecule having an internally-conjugated label) and compared to the rate of photobleaching measured for the unconjugated molecule. A measured decrease in the rate of photobleaching would be indicative of increased photostability. Methods of measuring photobleaching rates are known in the art, e.g., as described in Wüstner, D., et al. (2014) Molecules, 9:11096-11130: Brakenhoff, G. J., et al. (1994) *Journal of Microscopy,* 175(2):154-161; and Song, L., et al. (1995) *Biophys J.* 68(6):2588-2600. In some embodiments, a labeled biomolecule has decreased photobleaching relative to the unconjugated molecule, as measured by fluorescence recovery after photobleaching (FRAP), e.g., as described in Meyvis, T., et al. (1999) *Pharmaceutical Research,* 16(8): 1153-1162. In some embodiments, a labeled biomolecule has decreased photobleaching relative to the unconjugated molecule, as measured by fluorescence loss in photobleaching (FLIP), e.g., as described in Wüstner, D., et al. (2012) *BMC Bioinformatics,* 13:296.

In some embodiments, the disclosure provides new compositions for identifying single molecules based on one or more luminescent properties of those molecules. In some embodiments, a molecule (e.g., a luminescently labeled nucleotide) is identified based on its brightness, luminescence lifetime, absorption spectra, emission spectra, luminescence quantum yield, luminescence intensity, or a combination of two or more thereof. Identifying may mean assigning the exact molecular identity of a molecule, or may mean distinguishing or differentiating the particular molecule from a set of possible molecules. In some embodiments, a plurality of single molecules can be distinguished from each other based on different brightnesses, luminescence lifetimes, absorption spectra, emission spectra, luminescence quantum yields, luminescence intensities, or combinations of two or more thereof. In some embodiments, a single molecule is identified (e.g., distinguished from other molecules) by exposing the molecule to a series of separate light pulses and evaluating the timing or other properties of each photon that is emitted from the molecule. In some embodiments, information for a plurality of photons emitted sequentially from a single molecule is aggregated and evaluated to identify the molecule. In some embodiments, a luminescence lifetime of a molecule is determined from a plurality of photons that are emitted sequentially from the molecule, and the luminescence lifetime can be used to identify the molecule. In some embodiments, a luminescence intensity of a molecule is determined from a plurality of photons that are emitted sequentially from the molecule, and the luminescence intensity can be used to identify the molecule. In some embodiments, a luminescence lifetime and luminescence intensity of a molecule is determined from a plurality of photons that are emitted sequentially from the molecule, and the luminescence lifetime and luminescence intensity can be used to identify the molecule.

Accordingly, in some aspects of the application, a reaction sample is exposed to a plurality of separate light pulses and a series of emitted photons are detected and analyzed. In some embodiments, the series of emitted photons provides information about a single molecule that is present and that does not change in the reaction sample over the time of the experiment. However, in some embodiments, the series of emitted photons provides information about a series of different molecules that are present at different times in the reaction sample (e.g., as a reaction or process progresses).

Determination of a luminescence lifetime of a molecule can be performed using any suitable method (e.g., by measuring the lifetime using a suitable technique or by determining time-dependent characteristics of emission). In some embodiments, determining the luminescence lifetime of a molecule comprises determining the lifetime relative to one or more molecules (e.g., different luminescently labeled nucleotides in a sequencing reaction). In some embodiments, determining the luminescence lifetime of a molecule comprises determining the lifetime relative to a reference. In some embodiments, determining the luminescence lifetime of a molecule comprises measuring the lifetime (e.g., fluorescence lifetime). In some embodiments, determining the luminescence lifetime of a molecule comprises determining one or more temporal characteristics that are indicative of lifetime. In some embodiments, the luminescence lifetime of a molecule can be determined based on a distribution of a plurality of emission events (e.g., 1, 2, 3, 4, 5, 6, 7, 8, 9, 10, 11, 12, 13, 14, 15, 16, 17, 18, 19, 20, 30, 40, 50, 60, 70, 80, 90, 100, or more emission events) occurring across one or more time-gated windows relative to an excitation pulse. For example, a luminescence lifetime of a single molecule can be distinguished from a plurality of molecules having different luminescence lifetimes based on the distribution of photon arrival times measured with respect to an excitation pulse.

It should be appreciated that a luminescence lifetime of a single molecule is indicative of the timing of photons emitted after the single molecule reaches an excited state and the single molecule can be distinguished by information indicative of the timing of the photons. Some embodiments may include distinguishing a molecule from a plurality of molecules based on the molecule's luminescence lifetime by measuring times associated with photons emitted by the molecule. The distribution of times may provide an indication of the luminescence lifetime which may be determined from the distribution. In some embodiments, the single molecule is distinguishable from the plurality of molecules based on the distribution of times, such as by comparing the distribution of times to a reference distribution corresponding to a known molecule. In some embodiments, a value for the luminescence lifetime is determined from the distribution of times.

As used herein for single molecules, luminescence intensity refers to the number of emitted photons per unit time that are emitted by a molecule which is being excited by delivery of a pulsed excitation energy. In some embodiments, the luminescence intensity refers to the detected number of emitted photons per unit time that are emitted by a molecule which is being excited by delivery of a pulsed excitation energy, and are detected by a particular sensor or set of sensors.

In some aspects, the disclosure provides methods and compositions related to labeled biomolecules having enhanced emission brightness. As used herein, in some embodiments, "brightness" (and variations thereof, e.g., "bright," "brightly," etc.) refers to a parameter that reports on the average emission intensity per labeled reactant molecule. Thus, in some embodiments, "emission intensity" may be used to generally refer to brightness of a composition comprising brightly labeled reactants. In some embodiments, brightness of a labeled reactant is equal to the product of its quantum yield and extinction coefficient. In some embodiments, the labeled biomolecules of the disclosure are engineered to maximize quantum yield to promote increased brightness.

Luminescence quantum yield refers to the fraction of excitation events at a given wavelength or within a given spectral range that lead to an emission event, and is typically less than 1. In some embodiments, the luminescence quantum yield of a molecule described herein is between 0 and about 0.001, between about 0.001 and about 0.01, between about 0.01 and about 0.1, between about 0.1 and about 0.5, between about 0.5 and 0.9, or between about 0.9 and 1. In some embodiments, a molecule is identified by determining or estimating the luminescence quantum yield.

In some embodiments, internal labels described herein allow for the addition of successive luminescent labels to a labeled biomolecule for increasing brightness and/or luminescence intensity. In some embodiments, internally-labeled biomolecules comprising two or more luminescent labels exhibit brightness and/or luminescent intensity according to the formula $L_n(x)$, where $L_n$ is equal to the total number of luminescent labels on a labeled reactant and x is equal to the measured brightness or fluorescent intensity of the corresponding singly-labeled reactant. Accordingly, in some embodiments, a two-dye labeled reaction component possesses brightness and/or luminescent intensity that is doubled compared to the one-dye labeled analog. In some embodiments, a three- or four-dye labeled reaction component possesses brightness and/or luminescent intensity that is tripled or quadrupled, respectively, compared to the one-dye labeled analog. In some embodiments, the brightly labeled reactants described herein exhibit brightness and/or luminescent intensity that is at least 70%, at least 80%, at least 90%, at least 95%, at least 98%, or at least 99%$^0$ of the value predicted by $L_n(x)$.

Nucleic Acid Sequencing Reaction Compositions

Also provided herein are nucleic acid sequencing reaction compositions comprising two or more different types of labeled nucleotides in a reaction mixture, wherein at least one type of labeled nucleotide is a labeled nucleotide comprising a labeled biomolecule described herein.

In some embodiments, a nucleic acid sequencing reaction composition comprises two or more (e.g., two, three, four, five, or more) different types of labeled nucleotides. In some embodiments, a nucleic acid sequencing reaction composition comprises four different types of labeled nucleotides. In some embodiments, the four different types of labeled nucleotides comprising a first labeled nucleotide comprising guanine, a second labeled nucleotide comprising cytosine, a third labeled nucleotide comprising adenine, and a fourth labeled nucleotide comprising thymine or uracil.

In some embodiments, each type of labeled nucleotide in a nucleic acid sequencing reaction composition is present at a concentration of between about 100 and 1000 nM (e.g., between about 100 and 800 nM, between about 150 and 700 nM, between about 200 and 600 nM, or between about 250 and 500 nM).

In some embodiments, a nucleic acid sequencing reaction composition comprises a sequencing template comprising a polymerase in a complex with a target nucleic acid. In some embodiments, the complex further comprises a primer oligonucleotide having a sequence complementary to a portion of the target nucleic acid. In some embodiments, the complex is present at a concentration of between about 10 pM and 10 nM (e.g., between about 25 pM and 5 nM, between about 50 pM and 2 nM, between about 50 pM and 1 nM, between about 50 pM and 500 pM, between about 50 pM and 100 pM, between about 250 pM and 5 nM, between about 250 pM and 2 nM, between about 250 pM and 1 nM, or between about 250 pM and 500 pM.

In some embodiments, a nucleic acid sequencing reaction composition comprises one or more buffering agents (e.g., MES, MOPS, MOPSO, HEPES, Tris, TAPS, and other such suitable buffering agents known in the art). In some embodiments, the one or more buffering agents comprises MOPS. In some embodiments, a buffering agent is present at a concentration of between about 25 and 100 mM (e.g., between about 25 and 75 mM, between about 50 and 75 mM, or approximately 65 mM).

In some embodiments, a nucleic acid sequencing reaction composition comprises a divalent cation (e.g., magnesium ion, calcium ion). In some embodiments, the divalent cation comprises a magnesium or calcium salt (e.g., a salt comprising magnesium or calcium and acetate, chloride, phosphate, sulfate). In some embodiments, the salt is magnesium acetate. In some embodiments, a divalent cation is present at a concentration of between about 5 and 50 mM (e.g., between about 10 and 40 mM, between about 15 and 35 mM, between about 20 and 30 mM, or approximately 25 mM).

In some embodiments, a nucleic acid sequencing reaction composition comprises one or more monovalent salts (e.g., a sodium or potassium salt, such as sodium chloride, sodium acetate, potassium chloride, or potassium acetate). In some embodiments, the monovalent salt is present at a concentration of between about 10 and 200 mM (e.g., between about 25 and 150 mM, between about 25 and 40 mM, between about 50 and 150 mM, between about 100 and 150 mM). In some embodiments, a nucleic acid sequencing reaction composition comprises approximately 40 mM monovalent salt, such as 40 mM sodium chloride. In some embodiments, a nucleic acid sequencing reaction composition comprises approximately 120 mM monovalent salt, such as 120 mM potassium acetate.

In some embodiments, a nucleic acid sequencing reaction composition comprises one or more photostabilizers (e.g., one or more photoprotective additives, such as antioxidants, oxygen scavengers, triplet state quenchers, and similar energy-absorbing additives known in the art). In some embodiments, a photostabilizer comprises protocatechuic acid (PCA). In some embodiments, a photostabilizer comprises 4-nitrobenzyl alcohol (NBA). In some embodiments, a photostabilizer comprises trolox, or a derivative thereof. In some embodiments, a photostabilizer is present in a concentration of between about 0.1 mM and about 20 mM. In some embodiments, the concentration of trolox is about 5 mM. In some embodiments, the concentration of PCA is about 3 mM. In some embodiments, the concentration of PCA is about 8 mM. In some embodiments, the concentration of NBA is about 3 mM. A mixture with a photostabilizer (e.g., PCA) may also comprise an enzyme to regenerate the photostabilizer (e.g., protocatechuic acid dioxygenase (PCD)). In some embodiments, the concentration of PCD is about 0.3 mM. In some embodiments, the concentration of PCD is about 0.5 mg/mL.

In some embodiments, a nucleic acid sequencing reaction composition comprises one or more reducing agents. For example, in some embodiments, a nucleic acid sequencing reaction composition comprises between about 10 and 100 mM DTT (e.g., approximately 40 mM DTT).

Sequencing

Some aspects of the application are useful for sequencing biological polymers, such as nucleic acids and proteins. In some aspects, compositions and techniques described in the application can be used to identify a series of nucleotide or amino acid monomers that are incorporated into a nucleic acid or protein (e.g., by detecting a time-course of incorporation of a series of labeled nucleotide or amino acid monomers). In some embodiments, compositions and techniques described in the application can be used to identify a series of nucleotides that are incorporated into a template-dependent nucleic acid sequencing reaction product synthesized by a polymerase enzyme.

Accordingly, also provided herein are methods of determining the sequence of a template nucleic acid using the nucleic acid sequencing reaction compositions of the application. In some embodiments, methods of sequencing comprise steps of: (i) exposing a complex in a target volume, the complex comprising the template nucleic acid, a primer, and a polymerizing enzyme, to a nucleic acid sequencing reaction composition according to the disclosure (e.g., at least one labeled nucleotide comprising a labeled biomolecule described herein); (ii) directing a series of pulses of one or more excitation energies towards a vicinity of the target volume; (iii) detecting a plurality of emitted photons from luminescently labeled nucleotides during sequential incorporation into a nucleic acid comprising the primer; and (iv) identifying the sequence of incorporated nucleotides by determining timing and optionally luminescence intensity of the emitted photons.

In some embodiments, as used herein, an excitation energy is a pulse of light from a light source. In some embodiments, an excitation energy is in the visible spectrum. In some embodiments, an excitation energy is in the ultraviolet spectrum. In some embodiments, an excitation energy is in the infrared spectrum. In some embodiments, an excitation energy is at or near the absorption maximum of a luminescently labeled molecule from which a plurality of emitted photons are to be detected. In certain embodiments, the excitation energy is between about 500 nm and about 700 nm (e.g., between about 500 nm and about 600 nm, between about 600 nm and about 700 nm, between about 500 nm and about 550 nm, between about 550 nm and about 600 nm, between about 600 nm and about 650 nm, or between about 650 nm and about 700 nm). In certain embodiments, an excitation energy may be monochromatic or confined to a spectral range. In some embodiments, a spectral range has a range of between about 0.1 nm and about 1 nm, between about 1 nm and about 2 nm, or between about 2 nm and about 5 nm. In some embodiments a spectral range has a range of between about 5 nm and about 10 nm, between about 10 nm and about 50 nm, or between about 50 nm and about 100 nm.

Upon base pairing between a nucleobase of a target nucleic acid and the complementary nucleoside polyphosphate (e.g., dNTP), the polymerase incorporates the dNTP into the newly synthesized nucleic acid strand by forming a phosphodiester bond between the 3' hydroxyl end of the newly synthesized strand and the alpha phosphate of the dNTP. In examples in which a luminescent molecule (e.g., a labeled biomolecule as described herein) conjugated to the dNTP comprises a fluorophore, its presence is signaled by excitation and a pulse of emission is detected during and/or after the step of incorporation. For luminescent molecules (e.g., labeled biomolecules) that are conjugated to the terminal (gamma) phosphate of the dNTP, incorporation of the dNTP into the newly synthesized strand results in release of the beta and gamma phosphates and the luminescent molecule, which is free to diffuse in the sample well, resulting in a decrease in emission detected from the fluorophore.

In certain embodiments, the template-dependent nucleic acid sequencing product is carried out by naturally occurring nucleic acid polymerases. In some embodiments, the polymerase is a mutant or modified variant of a naturally occurring polymerase. In some embodiments, the template-dependent nucleic acid sequence product will comprise one or more nucleotide segments complementary to the template nucleic acid strand. In one aspect, the application provides a method of determining the sequence of a template (or target) nucleic acid strand by determining the sequence of its complementary nucleic acid strand.

The term "polymerase," as used herein, generally refers to any enzyme (or polymerizing enzyme) capable of catalyzing a polymerization reaction. Examples of polymerases include, without limitation, a nucleic acid polymerase, a transcriptase or a ligase. A polymerase can be a polymerization enzyme. Embodiments directed towards single molecule nucleic acid extension (e.g., for nucleic acid sequencing) may use any polymerase that is capable of synthesizing a nucleic acid complementary to a target nucleic acid molecule. In some embodiments, a polymerase may be a DNA polymerase, an RNA polymerase, a reverse transcriptase, and/or a mutant or altered form of one or more thereof.

Examples of polymerases include, but are not limited to, a DNA polymerase, an RNA polymerase, a thermostable polymerase, a wild-type polymerase, a modified polymerase, E. coli DNA polymerase I, T7 DNA polymerase, bacteriophage T4 DNA polymerase φ29 (psi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase. Tru polymerase. Tac polymerase, Tne polymerase. Tma polymerase, Tca polymerase, Tih polymerase, Tfi polymerase, Platinum Taq polymerases, Tbr polymerase, Tfl polymerase, Tth polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some embodiments, the polymerase is a single subunit polymerase. Non-limiting examples of DNA polymerases and their properties are described in detail in, among other places, DNA Replication 2nd edition, Kornberg and Baker, W. H. Freeman, New York, N.Y. (1991).

In another aspect, the application provides methods of sequencing target nucleic acids by sequencing a plurality of nucleic acid fragments, wherein the target nucleic acid comprises the fragments. In certain embodiments, the method comprises combining a plurality of fragment sequences to provide a sequence or partial sequence for the parent target nucleic acid. In some embodiments, the step of combining is performed by computer hardware and software. The methods described herein may allow for a set of related target nucleic acids, such as an entire chromosome or genome to be sequenced.

During sequencing, a polymerizing enzyme may couple (e.g., attach) to a priming location of a target nucleic acid molecule. The priming location can be a primer that is complementary to a portion of the target nucleic acid molecule. As an alternative the priming location is a gap or nick that is provided within a double stranded segment of the target nucleic acid molecule. A gap or nick can be from 0 to at least 1, 2, 3, 4, 5, 6, 7, 8, 9, 10, 20, 30, or 40 nucleotides in length. A nick can provide a break in one strand of a double stranded sequence, which can provide a priming location for a polymerizing enzyme, such as, for example, a strand displacing polymerase enzyme.

In some cases, a sequencing primer can be annealed to a target nucleic acid molecule that may or may not be immobilized to a solid support. A solid support can comprise, for example, a sample well (e.g., a nanoaperture, a reaction chamber) on a chip used for nucleic acid sequencing. In some embodiments, a sequencing primer may be immobilized to a solid support and hybridization of the target nucleic acid molecule also immobilizes the target nucleic acid molecule to the solid support. In some embodiments, a polymerase is immobilized to a solid support and soluble primer and target nucleic acid are contacted to the polymerase. However, in some embodiments a complex comprising a polymerase, a target nucleic acid and a primer is formed in solution and the complex is immobilized to a solid support (e.g., via immobilization of the polymerase, primer, and/or target nucleic acid). In some embodiments, none of the components in a sample well (e.g., a nanoaperture, a reaction chamber) are immobilized to a solid support. For example, in some embodiments, a complex comprising a polymerase, a target nucleic acid, and a primer is formed in solution and the complex is not immobilized to a solid support.

Under appropriate conditions, a polymerase enzyme that is contacted to an annealed primer/target nucleic acid can add or incorporate one or more nucleotides onto the primer, and nucleotides can be added to the primer in a 5' to 3', template-dependent fashion. Such incorporation of nucleotides onto a primer (e.g., via the action of a polymerase) can generally be referred to as a primer extension reaction. Each nucleotide can be associated with a detectable label that can be detected and identified (e.g., based on its luminescent lifetime and/or other characteristics) during the nucleic acid extension reaction and used to determine each nucleotide incorporated into the extended primer and, thus, a sequence of the newly synthesized nucleic acid molecule. Via sequence complementarity of the newly synthesized nucleic acid molecule, the sequence of the target nucleic acid molecule can also be determined. In some cases, annealing of a sequencing primer to a target nucleic acid molecule and incorporation of nucleotides to the sequencing primer can occur at similar reaction conditions (e.g., the same or similar reaction temperature) or at differing reaction conditions (e.g., different reaction temperatures). In some embodiments, sequencing by synthesis methods can include the presence of a population of target nucleic acid molecules (e.g., copies of a target nucleic acid) and/or a step of amplification of the target nucleic acid to achieve a population of target nucleic acids. However, in some embodiments sequencing by synthesis is used to determine the sequence of a single molecule in each reaction that is being evaluated (and nucleic acid amplification is not required to prepare the target template for sequencing). In some embodiments, a plurality of single molecule sequencing reactions are performed in parallel (e.g., on a single chip) according to aspects of the present application. For example, in some embodiments, a plurality of single molecule sequencing reactions are each performed in separate reaction chambers (e.g., nanoapertures, sample wells) on a single chip.

Embodiments are capable of sequencing single nucleic acid molecules with high accuracy and long read lengths, such as an accuracy of at least about 50%, 60%, 70%, 75%, 80%, 85%, 90%, 95%, 96%, 97%, 98%, 99%, 99.9%, 99.99%, 99.999%, or 99.9999%, and/or read lengths greater than or equal to about 10 base pairs (bp), 50 bp, 100 bp, 200 bp, 300 bp, 400 bp, 500 bp, 1000 bp, 10,000 bp, 20,000 bp, 30,000 bp, 40,000 bp, 50,000 bp, or 100,000 bp. In some embodiments, the target nucleic acid molecule used in single molecule sequencing is a single stranded target nucleic acid (e.g., deoxyribonucleic acid (DNA), DNA derivatives, ribonucleic acid (RNA). RNA derivatives) template that is added or immobilized to a sample well (e.g., nanoaperture) containing at least one additional component of a sequencing reaction (e.g., a polymerase such as, a DNA polymerase, a sequencing primer) immobilized or attached to a solid support such as the bottom or side walls of the sample well. The target nucleic acid molecule or the polymerase can be attached to a sample wall, such as at the bottom or side walls of the sample well directly or through a linker. The sample well (e.g., nanoaperture) also can contain any other reagents needed for nucleic acid synthesis via a primer extension reaction, such as, for example suitable buffers, co-factors, enzymes (e.g., a polymerase) and deoxyribonucleoside polyphosphates, such as, e.g., deoxyribonucleoside triphosphates, including deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include luminescent labels, such as luminescent labels of a labeled biomolecule provided herein.

In some embodiments, each class of dNTPs (e.g., adenine-containing dNTPs (e.g., dATP), cytosine-containing dNTPs (e.g., dCTP), guanine-containing dNTPs (e.g., dGTP), uracil-containing dNTPs (e.g., dUTPs) and thymine-containing dNTPs (e.g., dTTP)) is conjugated to a luminescent molecule that comprises distinct luminescent properties such that detection of light emitted from the luminescent molecule indicates the identity of the dNTP that was incorporated into the newly synthesized nucleic acid. Emitted light from the luminescent molecule (e.g., emitted light from a labeled biomolecule comprising at least one luminescent label) can be detected and attributed to its appropriate luminescent molecule (and, thus, associated dNTP) via any suitable device and/or method. The luminescent molecule may be conjugated to the dNTP at any position such that the presence of the luminescent molecule (e.g., a labeled biomolecule of the application) does not inhibit the incorporation of the dNTP into the newly synthesized nucleic acid strand or the activity of the polymerase. In some embodiments, the luminescent molecule is conjugated to the terminal phosphate (e.g., the gamma phosphate) of the dNTP.

In some embodiments, the single-stranded target nucleic acid template can be contacted with a sequencing primer, dNTPs, polymerase and other reagents necessary for nucleic acid synthesis. In some embodiments, all appropriate dNTPs can be contacted with the single-stranded target nucleic acid template simultaneously (e.g., all dNTPs are simultaneously present) such that incorporation of dNTPs can occur continuously. In other embodiments, the dNTPs can be contacted with the single-stranded target nucleic acid template sequentially, where the single-stranded target nucleic acid template is contacted with each appropriate dNTP separately, with washing steps in between contact of the single-stranded target nucleic acid template with differing dNTPs. Such a cycle of contacting the single-stranded target nucleic acid template with each dNTP separately followed by washing can be repeated for each successive base position of the single-stranded target nucleic acid template to be identified.

In some embodiments, the sequencing primer anneals to the single-stranded target nucleic acid template and the polymerase consecutively incorporates the dNTPs (or other nucleoside polyphosphate) to the primer based on the single-stranded target nucleic acid template. The unique luminescent molecule, such as a labeled biomolecule described herein, associated with each incorporated dNTP can be excited with the appropriate excitation light during or after incorporation of the dNTP to the primer and its emission can be subsequently detected, using, any suitable device(s) and/or method(s). Detection of a particular emission of light (e.g., having a particular emission lifetime, intensity, spectrum and/or combination thereof) can be attributed to a particular dNTP incorporated. The sequence obtained from the collection of detected luminescent molecules can then be used to determine the sequence of the single-stranded target nucleic acid template via sequence complementarity.

In some embodiments, the present disclosure provides methods and compositions that may be advantageously utilized in the technologies described in co-pending U.S. patent application Ser. Nos. 14/543,865, 14/543,867, 14/543,888, 14/821,656, 14/821,686, 14/821,688, 15/161, 067, 15/161,088, 15/161,125, 15/255,245, 15/255,303, 15/255.624, 15/261,697, 15/261,724, 15/600,979, 15/846, 967, 15/847,001, 62/289,019, 62/296,546, 62/310,398, 62/339,790, 62/343,997, 62/344,123, 62/426,144, and 62/505,525 the contents of each of which are incorporated herein by reference.

Kits

Also provided herein are kits for sequencing a template nucleic acid, the kit comprising two or more different types of labeled nucleotides, wherein at least one type of labeled nucleotide is a labeled nucleotide comprising a labeled biomolecule as described herein. In some embodiments, a kit comprises two or more (e.g., two, three, four, five, or more) different types of labeled nucleotides. In some embodiments, a kit comprises four different types of labeled nucleotides. In some embodiments, a kit comprises a polymerizing enzyme. In some embodiments, a kit comprises a primer complementary to the template nucleic acid.

In some embodiments, a kit comprises a plurality of types of labeled nucleotides comprising a labeled biomolecule as described herein. In some embodiments, at least one type (e.g., two, three, four, five, or more types) of labeled nucleotide comprises a labeled biomolecule having two or more internally-conjugated labels according to the application. In some embodiments, the plurality of nucleotides is selected from the labeled nucleotides depicted in FIGS. 1A-1G, 4A-4C, 5A, and 5C. In some embodiments, the kit further comprises a polymerizing enzyme (e.g., a DNA polymerase, as described elsewhere herein). In some embodiments, the kit further comprises a primer complementary to the template nucleic acid being sequenced.

Biconjugatable Labels

In another aspect, the present invention provides compounds. The compounds provided herein can be used as labels—that is, used in conjugation reactions to form the labeled biomolecules described herein. For example, provided herein are compounds of Formula (II):

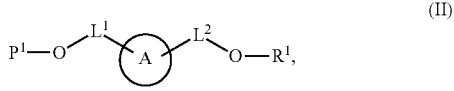
(II)

and salts thereof, wherein:

A is a polycyclic fluorophore;

$L^1$ and $L^2$ are independently linkers selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, optionally substituted heteroarylene, and combinations thereof;

$P^1$ is an oxygen protecting group; and $R^1$ is a reactive moiety.

The compounds of Formula (II), and salts thereof, as described herein, are bifunctional (e.g., "asymmetrical"). $R^1$ is a reactive moiety that can be used as a reactive handle in a conjugation reaction. $P^1$ is an oxygen protecting group that can be cleaved or removed after the conjugation reaction involving $R^1$, thereby revealing a free —OH group, which can then be used as a reactive moiety in a subsequent conjugation reaction. In certain embodiments, $R^1$ is a reactive moiety reactive in nucleoside coupling reactions (e.g., a phosphoramidite). Various oxygen protecting groups can be used at the position corresponding to $P^1$, and examples are provided herein.

$L^1$ and $L^2$ are defined herein, and exemplary embodiments are provided. Furthermore, exemplary embodiments of A are provided herein. All definitions and embodiments provided herein, including but not limited to those provided in the section INTERNALLY-LABELED BIOMOLECULES, are applicable to the compounds provided herein.

As defined herein, $P^1$ is an oxygen protecting group. Several examples of oxygen protecting groups are provided herein. In certain embodiments, $P^1$ is an optionally substituted triphenyl protecting group (e.g., trityl). In certain embodiments, $P^1$ is trityl, of the formula:

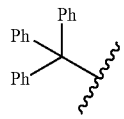

In certain embodiments. $P^1$ is 4-monomethoxytrityl (MMT), of the formula:

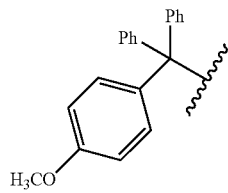

In certain embodiments, $P^1$ is 4,4-dimethoxytrityl (DMT), of the formula:

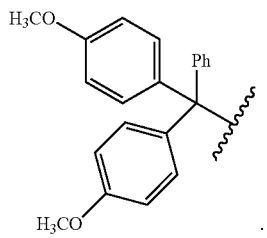 [SMILES: *C(c1ccccc1)(c1ccc(OC)cc1)c1ccc(OC)cc1]

In certain embodiments, $R^1$ is a reactive moiety. For example, $R^1$ is a reactive handle useful in polynucleotide synthesis, polypeptide synthesis, polysaccharide synthesis, etc. A reactive moiety can be any group capable of reacting with the second reactive moiety (e.g., an —OH or —NH$_2$ group) to form a covalent bond. A person of skill in the art would know what reactive moities can be used to form the bonds in polynucleotide synthesis, polypeptide synthesis, polysaccharide synthesis, etc. In certain embodiments, $R^1$ is a moiety useful in polynucleotide synthesis (e.g., a phosphoramidite). In certain embodiments, $R^1$ is a phosphoramidite. In certain embodiments, $R^1$ is a phosphoramidite of the formula:

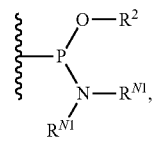

wherein $R^{N1}$ and $R^2$ are as defined herein. In certain embodiments, $R^1$ is a phosphoramidite of the formula:

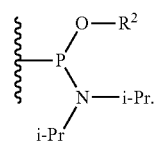

In certain embodiments, $R^1$ is a phosphoramidite of the formula:

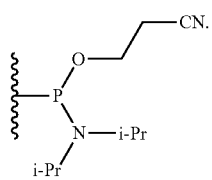

As defined herein, R² is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group. In certain embodiments, R² is optionally substituted alkyl. In certain embodiments, R² is optionally substituted $C_{1-6}$ alkyl. In certain embodiments R² is optionally substituted $C_{1-3}$ alkyl. In certain embodiments, R² is of the formula:

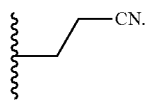

As defined herein, each instance of $R^{N1}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; optionally wherein two $R^{N1}$ bonded to the same nitrogen are joined together with the intervening atoms to form optionally substituted heterocyclyl or optionally substituted heteroaryl. In certain embodiments, $R^{N1}$ is optionally substituted alkyl. In certain embodiments, $R^{N1}$ is optionally substituted $C_{1-6}$ alkyl. In certain embodiments, $R^{N1}$ is unsubstituted $C_{1-6}$ alkyl. In certain embodiments, $R^{N1}$ is optionally substituted $C_{1-3}$ alkyl. In certain embodiments, $R^{N1}$ is unsubstituted $C_{1-3}$ alkyl. In certain embodiments, $R^{N1}$ is selected from the group consisting of methyl, ethyl, n-propyl, iso-propyl, n-butyl, iso-butyl, sec-butyl, and tert-butyl. In certain embodiments, $R^{N1}$ is iso-propyl. In certain embodiments, both instances of $R^{N1}$ are iso-propyl.

In certain embodiments, R¹ is a moiety reactive in nucleoside coupling reactions, such as a phosphoramidite. In certain embodiments, the compound of Formula (II) is of the formula:

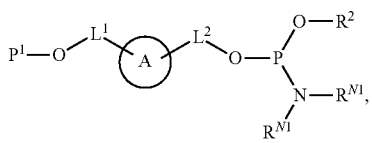

or a salt thereof, wherein:
R² is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group;
each instance of $R^{N1}$ is independently hydrogen, optionally substituted alkyl, optionally substituted alkenyl, optionally substituted alknyl, optionally substituted carbocyclyl, optionally substituted heterocyclyl, optionally substituted aryl, optionally substituted heteroaryl, optionally substituted acyl, or a nitrogen protecting group; optionally wherein two $R^{N1}$ bonded to the same nitrogen are joined together with the intervening atoms to form optionally substituted heterocyclyl or optionally substituted heteroaryl.

In certain embodiments, the compound of Formula (II) is of the formula:

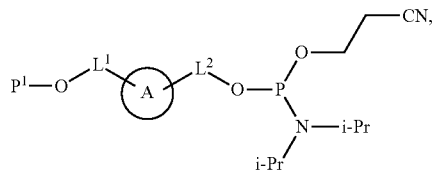

or a salt thereof.

In certain embodiments, the compound of Formula (II) is of the formula:

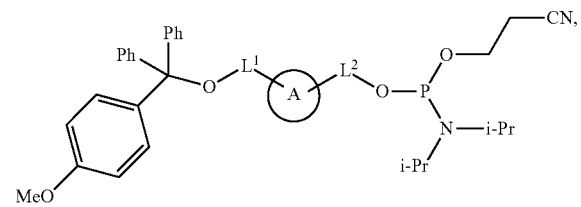

or a salt thereof.

In certain embodiments, the compound of Formula (II) is of the formula:

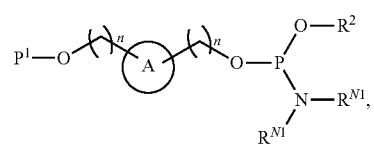

or a salt thereof, wherein:
each instance of n is an integer from 1-20, inclusive.

In certain embodiments, the compound of Formula (II) is of the formula:

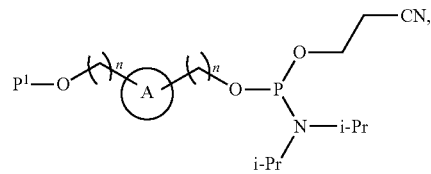

or a salt thereof, wherein:
each instance of n is an integer from 1-20, inclusive.

In certain embodiments, the compound of Formula (II) is of the formula:

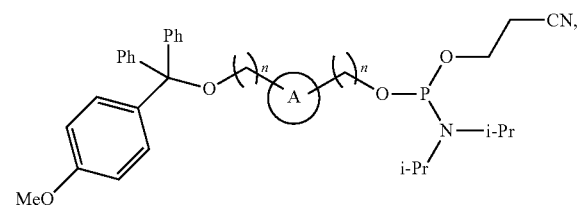

or a salt thereof.

In certain embodiments, the compound of Formula (II) is of the formula:

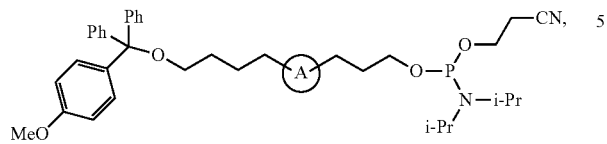

or a salt thereof.

As described herein, Ring A can be a polycyclic cyanine, such as Cy3B. In certain embodiments, the compound of Formula (II) is of the formula:

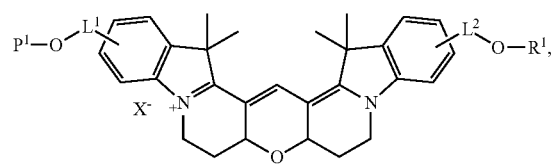

or a salt thereof, wherein X⁻ is a counterion or is absent.

In certain embodiments, the compound of Formula (II) is of the formula:

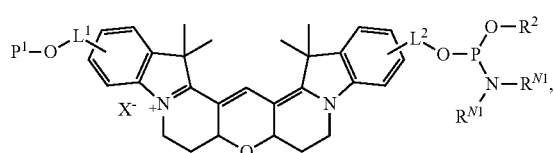

or a salt thereof.

In certain embodiments, the compound of Formula (II) is of the formula:

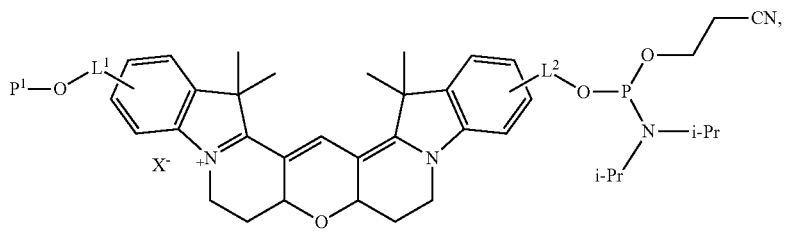

or a salt thereof.

In certain embodiments, the compound of Formula (II) is of the formula:

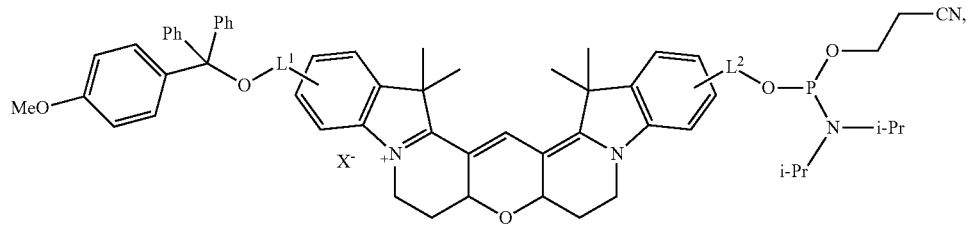

or a salt thereof.

In certain embodiments, the compound of Formula (II) is of the formula:

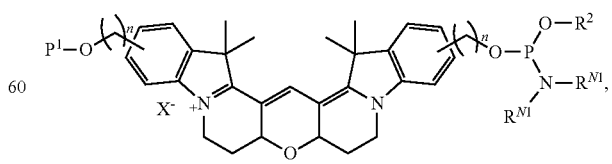

or a salt thereof.

In certain embodiments, the compound of Formula (II) is of the formula:

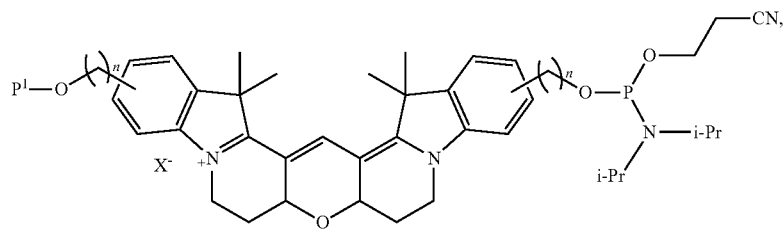
or a salt thereof.
In certain embodiments, the compound of Formula (II) is of the formula:
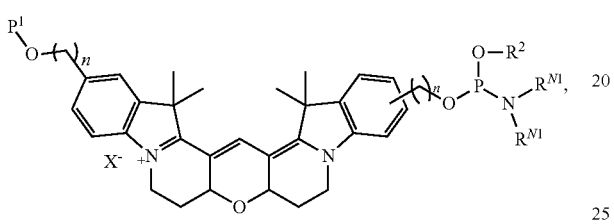
or a salt thereof.
In certain embodiments, the compound of Formula (II) is of the formula:
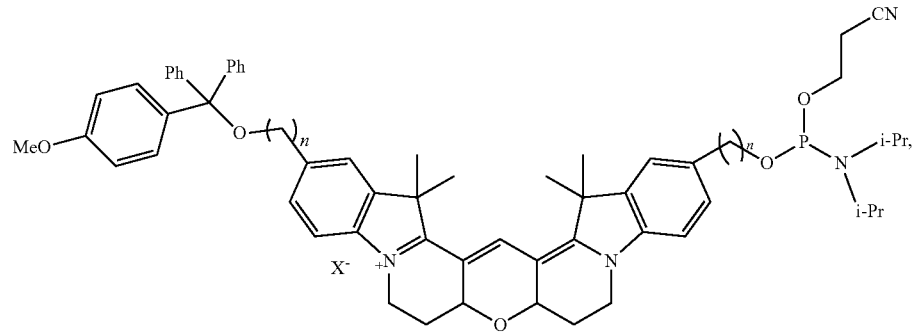
or a salt thereof.
In certain embodiments, the compound of Formula (II) is of the formula:
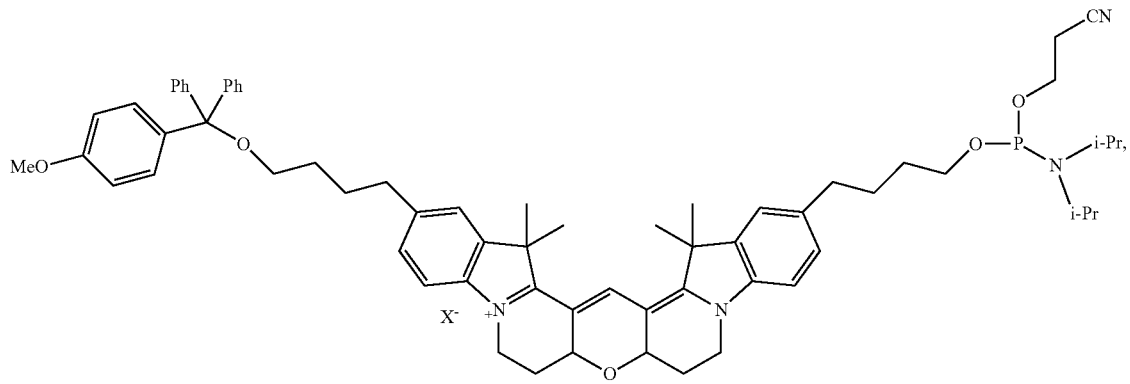
or a salt thereof.
In certain embodiments, the compound of Formula (II) is of the formula:

In certain embodiments, A can be a fluorone fluorophore, such as fluorescein or rhodamine, for example. In certain embodiments, the compound of Formula (II) is of the formula:

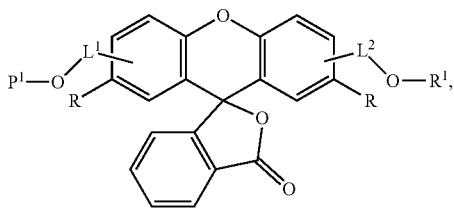

or a salt thereof, wherein:

each R is independently hydrogen, halogen, —N₃, —CN, —NO₂, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^O$, —SR$^S$, or N(R$^N$)₂.

In certain embodiments, the compound of Formula (II) is of the formula:

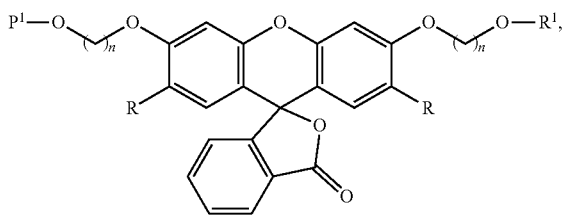

or a salt thereof, wherein:

n is independently an integer from 1-20, inclusive.

In certain embodiments, the compound of Formula (II) is of the formula:

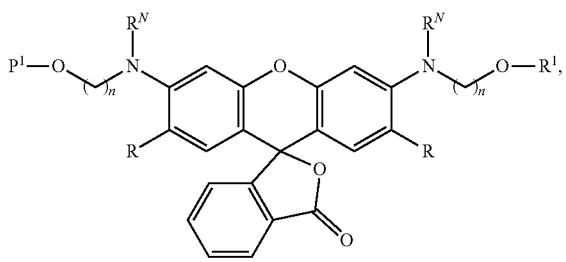

or a salt thereof, wherein:

n is independently an integer from 1-20, inclusive; and each instance of R$^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group.

In certain embodiments, the compound of Formula (II) is of the formula:

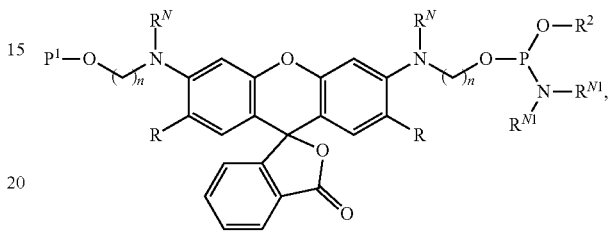

or a salt thereof.

In certain embodiments, the compound of Formula (II) is of the formula:

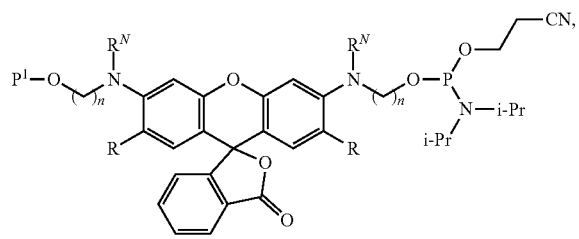

or a salt thereof.

In certain embodiments, the compound of Formula (II) is of the formula:

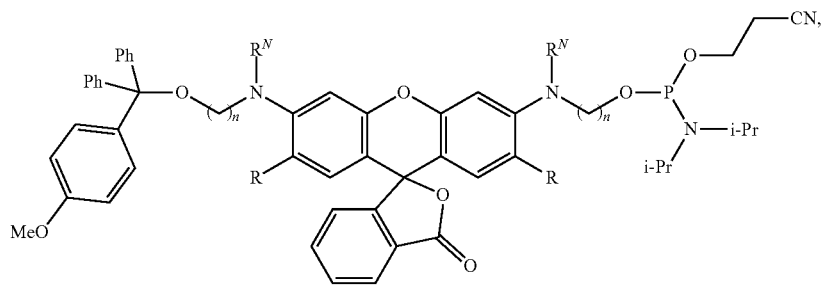

or a salt thereof.

In certain embodiments, the compound of Formula (II) is of the formula:

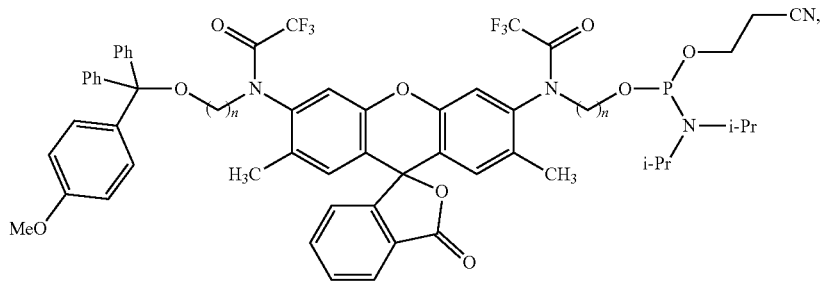

or a salt thereof.

In certain embodiments, the compound of Formula (II) is of the formula:

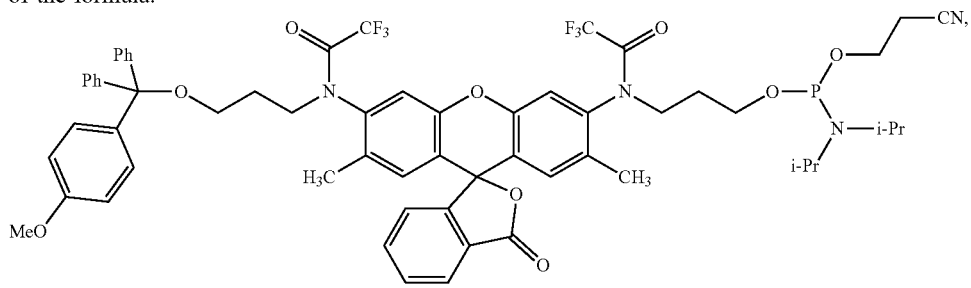

or a salt thereof.

As described herein, in certain embodiments, A is a BODIPY fluorophore. Therefore, in certain embodiments, the compound of Formula (II) is of the following formula:

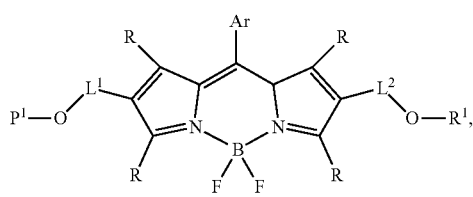

or a salt thereof, wherein:

each R is independently hydrogen, halogen, —$N_3$, —CN, —$NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^O$, —$SR^S$, or $N(R^N)_2$; and Ar is optionally substituted aryl or optionally substituted heteroaryl.

In certain embodiments, the compound of Formula (II) is of the formula:

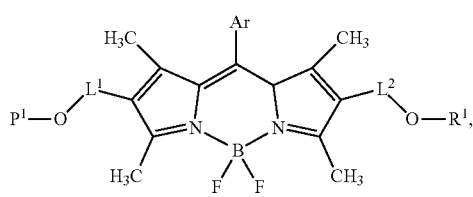

or a salt thereof.

In certain embodiments, the compound of Formula (II) is of the formula:

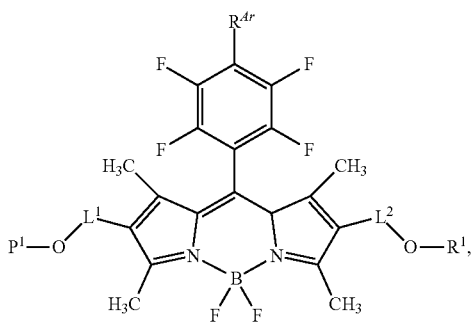

or a salt thereof, wherein:

$R^{Ar}$ is hydrogen, halogen, —$N_3$, —CN, —$NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^O$, —$SR^S$, or $N(R^N)_2$.

As generally defined herein, $R^O$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group. In certain embodiments, $R^O$ is hydrogen. In certain embodiments, $R^O$ is optionally substituted alkyl. In certain embodiments, $R^O$ is optionally substituted $C_{1-6}$ alkyl. In certain embodiments, $R^O$ is unsubstituted $C_{1-6}$ alkyl. In certain embodiments, $R^O$ is selected from methyl, ethyl, n-propyl, iso-propyl, n-butyl, iso-butyl, sec-butyl, and tert-butyl. In certain embodiments, $R^O$ is optionally substituted alkenyl. In certain embodiments, $R^O$ is optionally substituted alkynyl. In certain embodiments, $R^O$ is optionally substituted carbocyclyl. In certain embodiments, $R^O$ is optionally substituted heterocyclyl. In certain embodiments, $R^O$ is optionally substituted aryl. In certain embodiments, $R^O$ is optionally substituted heteroaryl. In certain embodiments, $R^O$ is optionally substituted acyl. In certain embodiments, $R^O$ is an oxygen protecting group. In certain embodiments, $R^O$ is —C(=O)Ph.

As generally defined herein, each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^N$ are joined together with the intervening atoms to form optionally substituted heterocyclyl or optionally substituted heteroaryl. In certain embodiments, $R^N$ is hydrogen. In certain embodiments, $R^N$ is optionally substituted alkyl. In certain embodiments, $R^N$ is optionally substituted $C_{1-6}$ alkyl. In certain embodiments, $R^N$ is unsubstituted $C_{1-6}$ alkyl. In certain embodiments, $R^N$ is selected from methyl, ethyl, n-propyl, iso-propyl, n-butyl, iso-butyl, sec-butyl, and tert-butyl. In certain embodiments, $R^N$ is optionally substituted alkenyl. In certain embodiments, $R^N$ is optionally substituted alkynyl. In certain embodiments, $R^N$ is optionally substituted carbocyclyl. In certain embodiments, $R^N$ is optionally substituted heterocyclyl. In certain embodiments, $R^N$ is optionally substituted aryl. In certain embodiments, $R^N$ is optionally substituted heteroaryl. In certain embodiments, $R^N$ is optionally substituted acyl. In certain embodiments, $R^N$ is a nitrogen protecting group. In certain embodiments, two $R^N$ are joined together with the intervening atoms to form optionally substituted heterocyclyl or optionally substituted heteroaryl As generally defined herein, $R^S$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a sulfur protecting group. In certain embodiments, $R^S$ is hydrogen. In certain embodiments, $R^S$ is optionally substituted alkyl. In certain embodiments, $R^S$ is optionally substituted $C_{1-6}$ alkyl. In certain embodiments, $R^S$ is unsubstituted $C_{1-6}$ alkyl. In certain embodiments, $R^S$ is selected from methyl, ethyl, n-propyl, iso-propyl, n-butyl, iso-butyl, sec-butyl, and tert-butyl. In certain embodiments, $R^S$ is optionally substituted alkenyl. In certain embodiments, $R^S$ is optionally substituted alkynyl. In certain embodiments, $R^S$ is optionally substituted carbocyclyl. In certain embodiments, $R^S$ is optionally substituted heterocyclyl. In certain embodiments, $R^S$ is optionally substituted aryl. In certain embodiments, $R^S$ is optionally substituted heteroaryl. In certain embodiments, $R^S$ is optionally substituted acyl. In certain embodiments, $R^S$ is a sulfur protecting group. In certain embodiments, $R^S$ is PEG (polyethylene glycol). In certain embodiments, $R^S$ is —$(CH_2CH_2O)_mOCH_3$. In certain embodiments, —$SR^S$ is —$S(CH_2CH_2O)_mOCH_3$.

In certain embodiments, the compound of Formula (II) is of the formula:

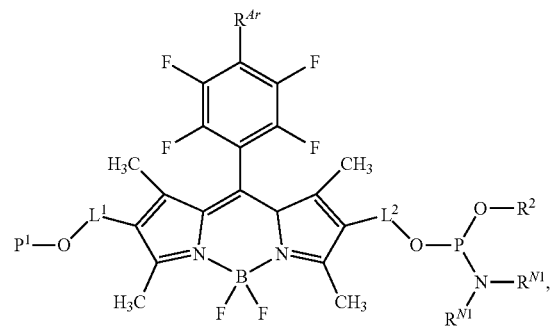

or a salt thereof.

In certain embodiments, the compound of Formula (II) is of the formula:

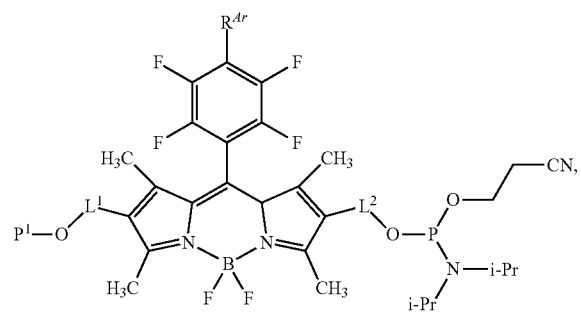

or a salt thereof.

In certain embodiments, the compound of Formula (II) is of the formula:

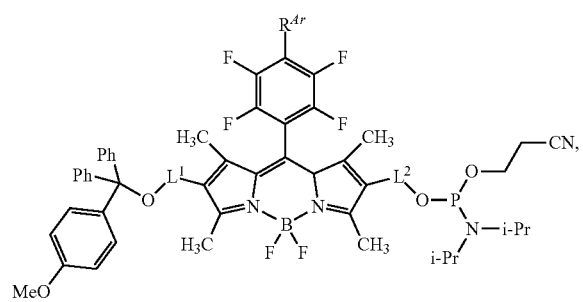

or a salt thereof.

In certain embodiments, the compound of Formula (II) is of the formula:

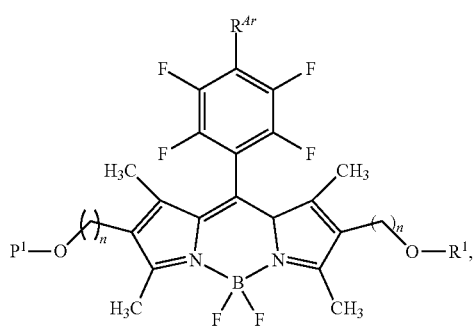

or a salt thereof, wherein n is independently an integer from 1-20, inclusive.

In certain embodiments, the compound of Formula (II) is of the formula:

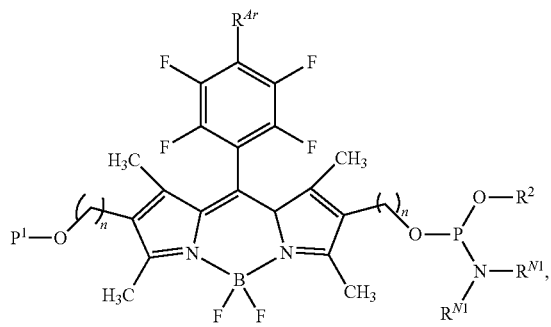

or a salt thereof.

In certain embodiments, the compound of Formula (II) is of the formula:

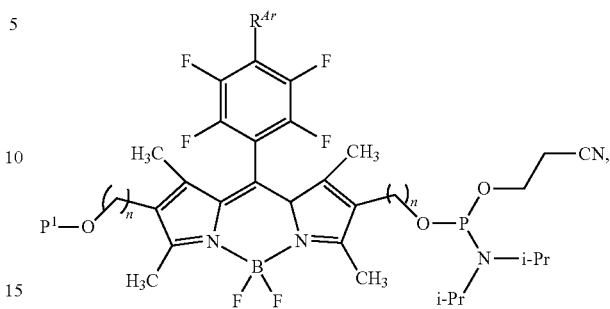

or a salt thereof.

In certain embodiments, the compound of Formula (II) is of the formula:

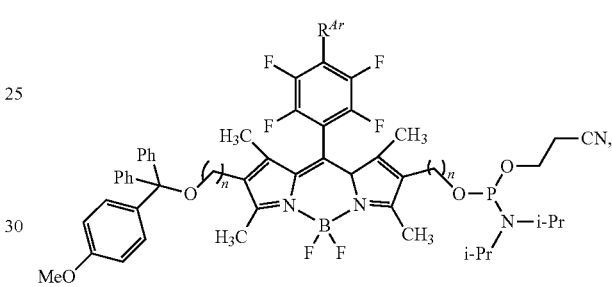

or a salt thereof.

In certain embodiments, the compound of Formula (II) is of the formula:

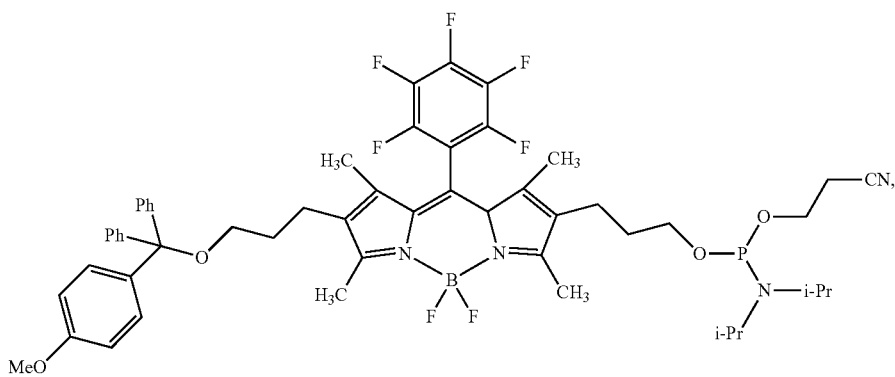

or a salt thereof.

In certain embodiments, the compound of Formula (II) is of the formula:

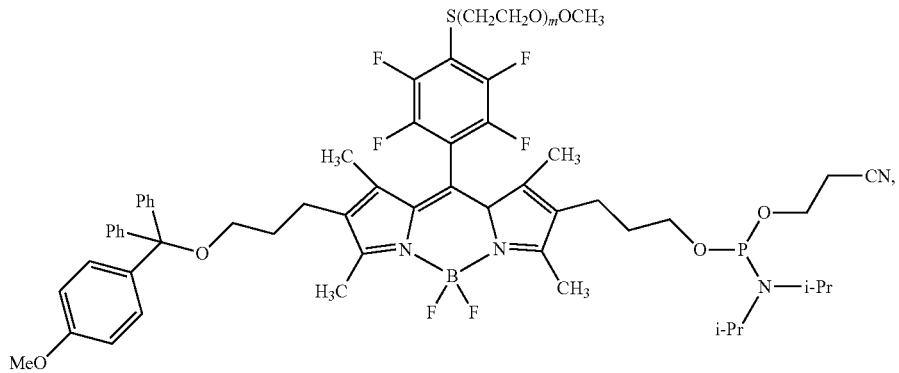

or a salt thereof.

Methods for Preparing Internally-Labeled Biomolecules

Also provided herein are methods for preparing the internally-labeled biomolecules (e.g., biomolecules of Formula (I)) described herein. In general, the methods comprise two subsequent conjugation steps involving the bifunctional compounds (e.g., compounds of Formula (II)) provided herein.

Thus, provided herein are methods for preparing labeled biomolecules, the methods comprising:

(i) contacting a monomeric or oligomeric biomolecule of formula $Q^1$-OH, or a salt thereof, with a compound of Formula (II), or a salt thereof, under conditions sufficient to promote conjugation to yield a conjugate of the formula:

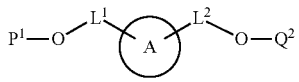

or a salt thereof;

(ii) deprotecting the conjugate formed in step (i) under conditions sufficient to cleave the $P^1$ protecting group and yield a conjugate of the formula:

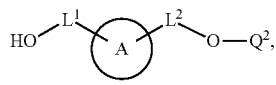

or a salt thereof:

(iii) contacting the conjugate formed in step (ii) with a monomeric or oligomeric biomolecule of formula $Q^1$-O—$R^1$, or a salt thereof, under conditions sufficient to promote conjugation to yield a labeled biomolecule of Formula (I):

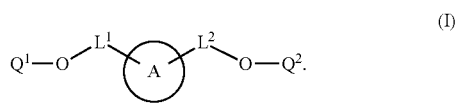

For example, in certain embodiments when an internally-labeled oligonucleotide is prepared, the compound of Formula (II) can be coupled to coupled with $Q^2$-OH using standard phosphoramidite chemistry. Furthermore, in certain embodiments when an internally-labeled oligonucleotide is prepared, unprotected conjugate bearing a hydroxyl moiety formed in step (ii) is coupled to alkyl-(2-cyanoethyl)-N,N-diisopropyl)-phosphoramidites, such as are used in standard oligonucleotide synthesis. The reaction can be carried out in the presence of an activator such as 1H-tetrazole, ethylthiotetrazole, benzylthiotetrazole, dicyanoimidazole, or other suitable weak acid. Step (iii) can, in certain embodiments, then be carried out using standard phosphoramidite chemistry.

Methods for Preparing Biconjugatable Labels

In yet another aspect, the present invention provides synthetic methods for preparing the biconjugatable labels described herein (e.g., compounds of Formula (II)).

General Reaction Parameters

The following embodiments apply to all synthetic methods described herein.

The reactions provided and described herein may involve one or more reagents. In certain embodiments, a reagent may be present in a catalytic amount. In certain embodiments, a catalytic amount is from 0-1 mol %, 0-5 mol %, 0-10 mol %, 1-5 mol %, 1-10 mol %, 5-10 mol %, 10-20 mol %, 20-30 mol %, 30-40 mol %, 40-50 mol %, 50-60 mol %, 60-70 mol %, 70-80 mol %, 80-90 mol %, or 90-99 mol %. In certain embodiments, a reagent may be present in a stoichiometric amount (e.g., about 1 equivalent). In certain embodiments, a reagent may be present in excess amount (e.g., greater than 1 equivalent). In certain embodiments, the excess amount is about 1.1, 1.2, 1.3, 1.4, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 15, or 20 equivalents. In certain embodiments, the excess amount is from about 1.1-2, 2-3, 3-4, 4-5, 1.1-5, 5-10, 10-15, 15-20, or 10-20 equivalents. In certain embodiments, the excess amount is greater than 20 equivalents.

A reaction described herein may be carried out at any temperature. In certain embodiments, a reaction is carried out at or around room temperature (rt) (21° C. or 70° F.). In certain embodiments, a reaction is carried out at below room temperature (e.g., from −100° C. to 21° C.). In certain embodiments, a reaction is carried out at or around −78° C. In certain embodiments, a reaction is carried out at or around −10° C. In certain embodiments, a reaction is carried out at around 0° C. In certain embodiments, a reaction is carried out at above room temperature. In certain embodiment, a reaction is carried out at 30, 40, 50, 60, 70, 80, 110, 120, 130, 140, or 150° C. In certain embodiments, a reaction is carried out at above 150° C.

A reaction described herein may be carried out in a solvent, or a mixture of solvents (e.g., cosolvents). Solvents can be polar or non-polar, protic or aprotic. Any solvent may be used in the reactions described herein, and the reactions are not limited to particular solvents or combinations of solvents. Common organic solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahydrofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, p-xylene.

A reaction described herein may be carried out over any amount of time. In certain embodiments, a reaction is allowed to run for seconds, minutes, hours, or days.

Methods described herein can be used to prepare compounds in any chemical yield. In certain embodiments, a compound is produced in from 1-10%, 10-20% 20-30%, 30-40%, 40-50%, 50-60%, 60-70%, 70-80%, 80-90%, or 90-100% yield. In certain embodiments, the yield is the percent yield after one synthetic step. In certain embodiments, the yield is the percent yield after more than one synthetic step (e.g., 2, 3, 4, or 5 synthetic steps).

Methods described herein may further comprise one or more purification steps. For example, in certain embodiments, a compound produced by a method described herein may be purified by chromatography, extraction, filtration, precipitation, crystallization, or any other method known in the art. In certain embodiments, a compound or mixture is carried forward to the next synthetic step without purification (e.g., crude).

Methods for Preparing Cy3B-Based Labels

Provided herein is a method of preparing a compound of Formula (III):

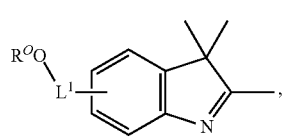
(III)

or a salt thereof, the method comprising coupling a compound of the formula:

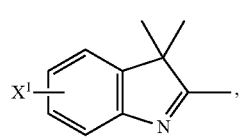

or a salt thereof, with a compound of the formula

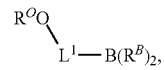

or a salt thereof, in the presence of palladium to yield a compound of Formula (III), or a salt thereof, wherein:

$X^1$ is halogen or a leaving group;

$B(R^B)_2$ is a borane, boronic acid, or boronic ester;

$L^1$ is a linker selected from the group consisting of optionally substituted alkylene, optionally substituted alkenylene, optionally substituted alkynylene, optionally substituted heteroalkylene, optionally substituted heteroalkenylene, optionally substituted heteroalknylene, optionally substituted carbocyclylene, optionally substituted heterocyclylene, optionally substituted arylene, optionally substituted heteroarylene, and combinations thereof, and $R^O$ is an oxygen protecting group.

In certain embodiments, the reaction to yield a compound of Formula (III) is carried out in the presence of a metal other than palladium. For example, the reaction can be palladium-catalyzed, or catalyzed by a different metal. In certain embodiments, the metal is a transition metal.

As defined herein, the group —$B(R^B)_2$ is a borane, a boronic acid, or a boronic ester. In certain embodiments, —$B(R^B)_2$ is a borane. In certain embodiments, —$B(R^B)_2$ is a boronic acid. In certain embodiments, —$B(R^B)_2$ is a boronic ester. In certain embodiments, —$B(R^B)_2$ is a borane of the formula:

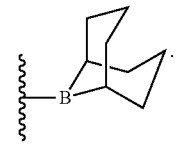 [SMILES: *B1C2CCCC1CCC2]

As defined herein, each instance of $R^B$ is independently optionally substituted alkyl, optionally substituted carbocyclyl, optionally substituted heterocyclyl, optionally substituted aryl, optionally substituted heteroaryl, —OH, or —$OR^O$. Optionally, two $R^B$ are joined together with the intervening atoms to form optionally substituted carbocyclyl or optionally substituted heterocyclyl. In general, —$B(R^B)_2$ is any suitable borane, boronic acid, or boronic ester useful in a metal-promoted or metal-catalyzed cross-coupling reaction.

The linker $L^1$ is as defined herein.

As defined herein, $X^1$ is a halogen or a leaving group. In certain embodiments, $X^1$ is a halogen. In certain embodiments, $X^1$ is a leaving group. In certain embodiments, $X^1$ is —Cl, —Br, or —I. In certain embodiments, $X^1$ is —I In certain embodiments of the coupling reaction, the compound of Formula (III) is of the formula:

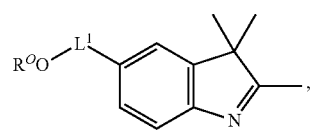

or a salt thereof; and the starting material is therefore of the formula:

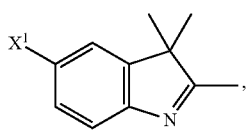

or a salt thereof.

In certain embodiments, the compound of Formula (III) is of the formula:

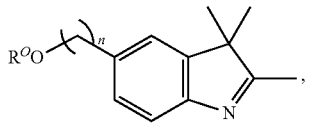

or a salt thereof; wherein n is an integer from 1-20, inclusive; and therefore the starting materials are of the formulae:

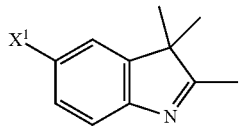 and 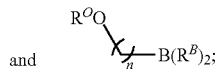

or salts thereof.

As described above, the coupling reaction is carried out in the presence of palladium. In certain embodiments, the palladium is a palladium complex. In certain embodiments, the palladium complex is a palladium(II) complex. In certain embodiments, the palladium complex is $PdCl_2(dppf)$. In certain embodiments, the palladium is present in a catalytic amount. In other embodiments, the palladium is present in a stoichiometric or excess amount.

In certain embodiments, the coupling reaction is carried out in the presence of a base. In certain embodiments, the base is a carbonate base. In certain embodiments, the base is $Cs_2CO_3$.

In certain embodiments, the coupling reaction is carried out in a solvent. In certain embodiments, the solvent is THF, DMF, or a mixture thereof.

The coupling reaction can be carried out at any temperature. In certain embodiments, the reaction is carried out at room temperature. In certain embodiments, the reaction is carried out at above room temperature (i.e., elevated temperature). In certain embodiments, the reaction is carried out at between room temperature and 100° C. In certain embodiments, the reaction is carried out at between 50° and 100° C. In certain embodiments, the reaction is carried out at around 70° C.

In certain embodiments, the method further comprises a step of alkylating a compound of Formula (III) with a compound of the formula:

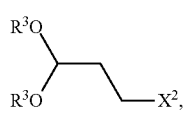

or a salt thereof, to yield a compound of the formula:

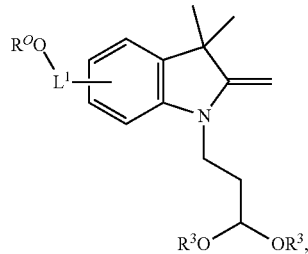

or its tautomer:

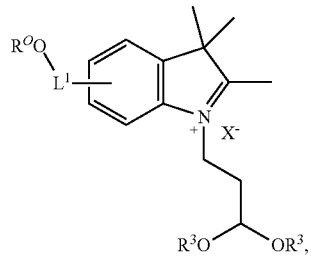

or a salt thereof, wherein:

$X^2$ is halogen or a leaving group; and each $R^3$ is independently optionally substituted alkyl, optionally substituted acyl, or an oxygen protecting group; or optionally two $R^3$ are joined together with the intervening atoms to form optionally substituted heterocyclyl.

In certain embodiments, the product is a compound of the formula:

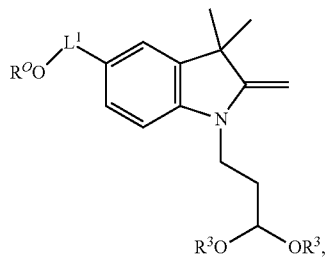

or its tautomer:

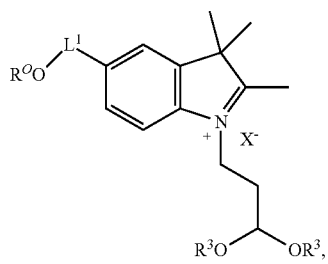

or a salt thereof.

In certain embodiments, the step of alkylating is carried out in the presence of a base. In certain embodiments, the base is a halide salt. In certain embodiments, the base is an iodide salt. In certain embodiments, the base is KI. In certain embodiments, the step of alkylating is carried out in a solvent. In certain embodiments, the solvent is acetonitrile (MeCN). In certain embodiments, the reaction is carried out at room temperature. In certain embodiments, the reaction is carried out at elevated temperature. In certain embodiments, the reaction is carried out at around 100° C.

As defined herein, $X^2$ is halogen or a leaving group. In certain embodiments, $X^2$ is a halogen. In certain embodiments, $X^2$ is —Cl, —Br, or —I. In certain embodiments, $X^2$ is —Br. In certain embodiments, $X^2$ is a leaving group.

As defined herein, each $R^3$ is independently optionally substituted alkyl, optionally substituted acyl, or an oxygen protecting group; or optionally two $R^3$ are joined together with the intervening atoms to form optionally substituted heterocyclyl. In certain embodiments, $R^3$ is optionally substituted alkyl. In certain embodiments, $R^3$ is optionally substituted acyl. In certain embodiments, $R^3$ is an oxygen protecting group. In certain embodiments, two $R^3$ are joined together with the intervening atoms to form optionally substituted heterocyclyl. In certain embodiments, two $R^3$ are joined together with the intervening atoms to form:

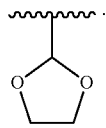

In certain embodiments, two $R^3$ are joined together with the intervening atoms to form:

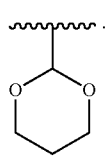

In certain embodiments, the method further comprises reacting the compound of formula:

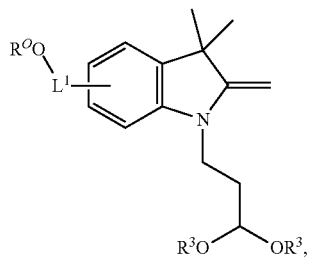

(IV)

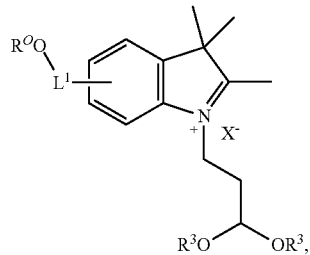

or a salt thereof, in the presence of a formamidine, to yield a compound of formula:

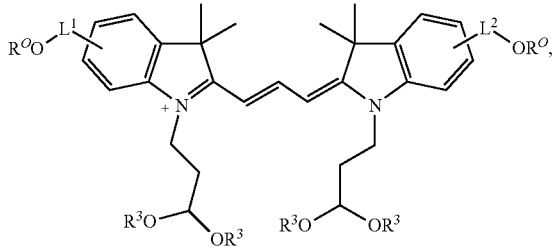

or a salt thereof. In certain embodiments, the reaction entails (i) reacting the compound of Formula (IV), or a salt thereof, in the presence of a formamidine to form an intermediate; and (ii) reacting the intermediate formed in step (i) with another compound of Formula (IV), or a salt thereof, to yield the product shown above.

In certain embodiments, the formamidine in step (i) is diphenylformamidine. In certain embodiments, the reaction in step (i) is carried out in the presence of a base. In certain embodiments, the base is a pyridine base. In certain embodiments, the base is DMAP. In certain embodiments, the reaction is step (i) is carried out in the presence of an anhydride. In certain embodiments, the anhydride is acetic anhydride ($Ac_2O$). In certain embodiments, the reaction in step (i) is carried out at elevated temperature (e.g., around 125° C.). In certain embodiments, the reaction is carried out in a solvent. In certain embodiments, the reaction in step (ii) is carried out in the presence of a base. In certain embodiments, the base is an amine base (e.g., a trialkylamine base). In certain embodiments, the base is $Et_3N$, wherein the reaction is carried out in the presence of a base. In certain embodiments, the reaction is carried out in a solvent. In certain embodiments, the solvent is EtOH. In certain embodiments, the reaction is carried out at elevated temperature (e.g., around 80° C.).

In certain embodiments, the product is of the formula:

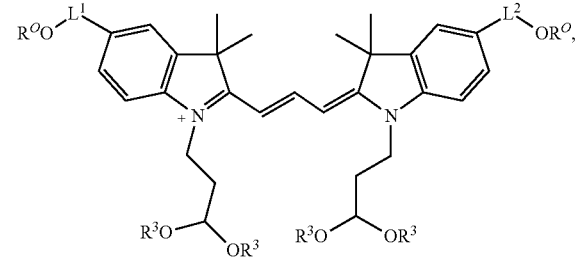

or a salt thereof.

In certain embodiments, the method further comprises cyclizing a compound of formula:

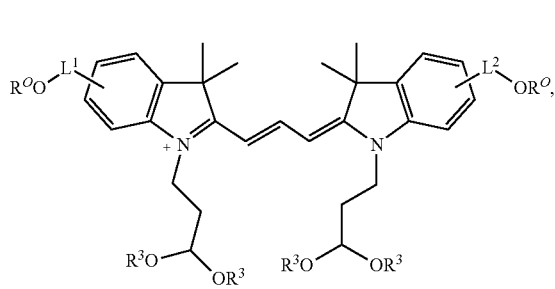

or a salt thereof, in the presence of an acid, to yield a compound of the formula:

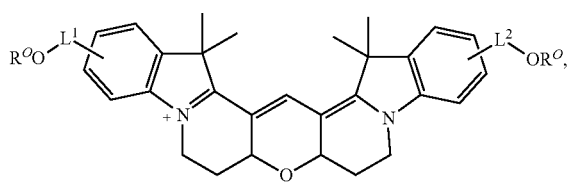

or a salt thereof. In certain embodiments, the acid is a sulfonic acid. In certain embodiments, the acid is sulfuric acid. In certain embodiments, the reaction is carried out in a solvent. In certain embodiments, the solvent is $CH_2Cl_2$. In certain embodiments, the reaction is carried out at elevated temperature (e.g., around 60° C.).

In certain embodiments, the product is of the formula:

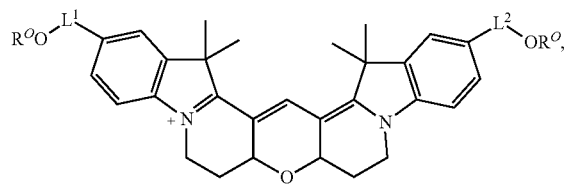

or a salt thereof.

In certain embodiments, the method further comprises a step of deprotecting a compound of the formula:

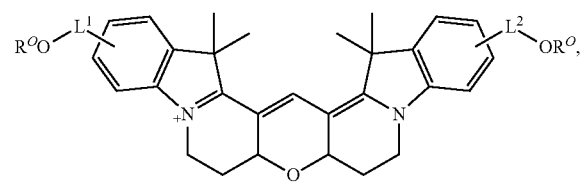

or a salt thereof, to yield a compound of the formula:

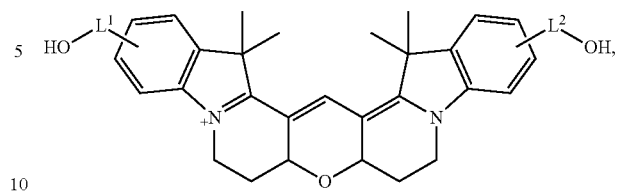

or a salt thereof.

In certain embodiments, the compound if of the formula:

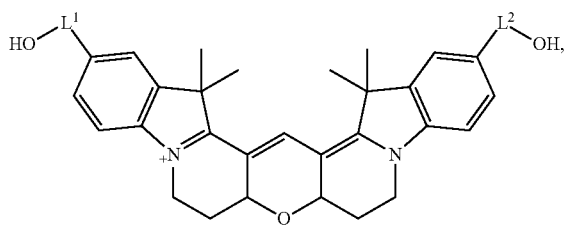

or a salt thereof.

In certain embodiments, the method further comprises the steps of:

(i) protecting a compound of the formula:

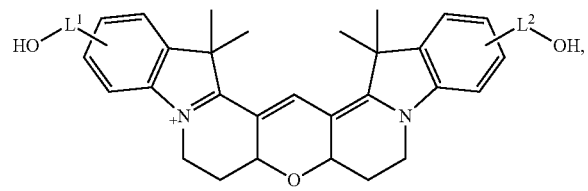

or a salt thereof, to yield a compound of the formula:

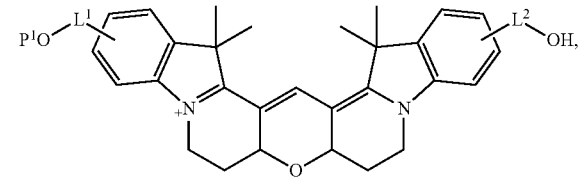

or a salt thereof; and (ii) reacting the compound produced in step (i) under conditions sufficient form a compound of the formula:

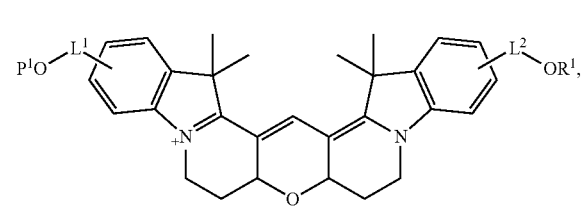

or a salt thereof.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March. *March's Advanced Organic Chemistry*, 5$^{th}$ Edition. John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind, 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{1-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, aziridinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1.4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 ix electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_3$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)OR)$_2$, —OP(=O)(R$^{aa}$)$_2$, —OP(=O)(OR$^{aa}$)$_2$, —P(=O)(N(R$^{bb}$)$_2$)$_2$, —OP(=O)N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{cc}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion:

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl. C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ perhaloalkyl, $C_{1-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion:

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups:

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion:

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen. $C_{1-6}$ alkyl, $C_{1-6}$ perhaloalkyl, $C_{2-6}$ alkenyl. $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)C$_{1-6}$ alkyl, —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(=NH)NH(C$_{1-6}$ alkyl), —OC(=NH)NH$_2$, —NHC(=NH)N(C$_{1-6}$ alkyl)$_2$, —NHC(=NH)NH$_2$, —NHSO$_2$(C$_{1-6}$ alkyl), —SO$_2$N(C$_{1-6}$ alkyl), —SO$_2$NH(C$_{1-6}$ alkyl), —SO$_2$NH$_2$, —SO$_2$(C$_{1-6}$ alkyl), —SO$_2$O(C$_{1-6}$ alkyl), —OSO$_2$(C$_{1-6}$ alkyl), —SO(C$_{1-6}$ alkyl), —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{1-10}$ carbocyclyl, $C_{6-10}$ aryl, 3-10 membered heterocyclyl, 5-10 membered heteroaryl; or two geminal $R^{as}$ substituents can be joined to form =O or =S; wherein $X^-$ is a counterion.

In certain embodiments, carbon atom substituents include: halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(=NH)NH(C$_{1-6}$ alkyl), —OC(=NH)NH$_2$, —NHC(=NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$(C$_{1-6}$ alkyl), —SO$_2$O(C$_{1-6}$ alkyl), —OSO$_2$(C$_{1-6}$ alkyl), —SO(C$_{1-6}$ alkyl), —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$$^+$X$^-$, —OP(OR$^{cc}$)$_2$, —P(OR$^{cc}$)$_3$$^+$X$^-$, —OP(=O)R$^{aa}$)$_2$, —OP(=O)(OR$^{cc}$)$_2$, and —OP(=O)(N(R$^{bb}$)$_2$)$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "acyl" refers to a group having the general formula —C(=O)R$^{X1}$—C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, —C(=S)O(R$^{X1}$), —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino: or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (e.g., —C(=O)R$^{aa}$), carboxylic acids (e.g., —CO$_2$H), aldehydes (—CHO), esters (e.g., —CO$_2$R$^{aa}$, —C(=O)SR$^{aa}$, —C(=S)SR$^{aa}$), amides (e.g., —C(=O)N(R$^{bb}$)$_2$, —C(=O)NR$^{bb}$SO$_2$R$^{aa}$, —C(=S)N(R$^{bb}$)$_2$), and imines (e.g., —C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

The term "silyl" refers to the group —Si(R$^{aa}$)$_3$, wherein R$^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate. [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), P-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2- trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3^+X^-$, $-P(OR^{cc})_2$, $-P(OR^{cc})_3^+X^-$, $-P(=O)(R^{aa})_2$, $-P(=O)(OR^{cc})_2$, and $-P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition. John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3^+X^-$, $-P(OR^{cc})_2$, $-P(OR^{cc})_3^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference. In certain embodiments, a sulfur protecting group is acetamidomethyl, t-butyl, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5\text{-}(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, OC(=NR$^{bb}$)N(R$^{bb}$), —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

The following definitions are more general terms used throughout the present application.

As used herein, the term "salt" refers to any and all salts, and encompasses pharmaceutically acceptable salts. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "catalysis," "catalyze," or "catalytic" refers to the increase in rate of a chemical reaction due to the participation of a substance called a "catalyst." In certain embodiments, the amount and nature of a catalyst remains essentially unchanged during a reaction. In certain embodiments, a catalyst is regenerated, or the nature of a catalyst is essentially restored after a reaction. A catalyst may participate in multiple chemical transformations. The effect of a catalyst may vary due to the presence of other substances known as inhibitors or poisons (which reduce the catalytic activity) or promoters (which increase the activity). Catalyzed reactions have lower activation energy (rate-limiting free energy of activation) than the corresponding uncatalyzed reaction, resulting in a higher reaction rate at the same temperature. Catalysts may affect the reaction environment favorably, bind to the reagents to polarize bonds, form specific intermediates that are not typically produced by a uncatalyzed reaction, or cause dissociation of reagents to reactive forms.

The term "solvent" refers to a substance that dissolves one or more solutes, resulting in a solution. A solvent may serve as a medium for any reaction or transformation described herein. The solvent may dissolve one or more reactants or reagents in a reaction mixture. The solvent may facilitate the mixing of one or more reagents or reactants in a reaction mixture. The solvent may also serve to increase or decrease the rate of a reaction relative to the reaction in a different solvent. Solvents can be polar or non-polar, protic or aprotic. Common organic solvents useful in the methods are described herein.

EXAMPLES

Synthesis of Bifunctional Labels

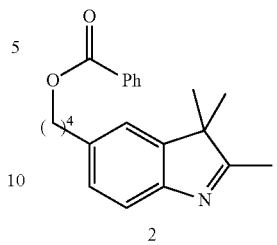

Indolenine benzoate 2

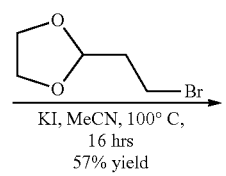

Alkylated indolenine 3

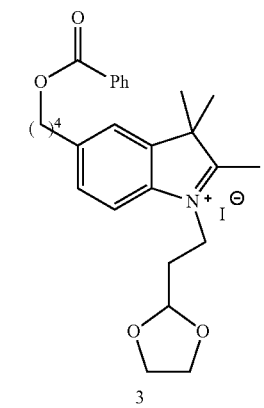

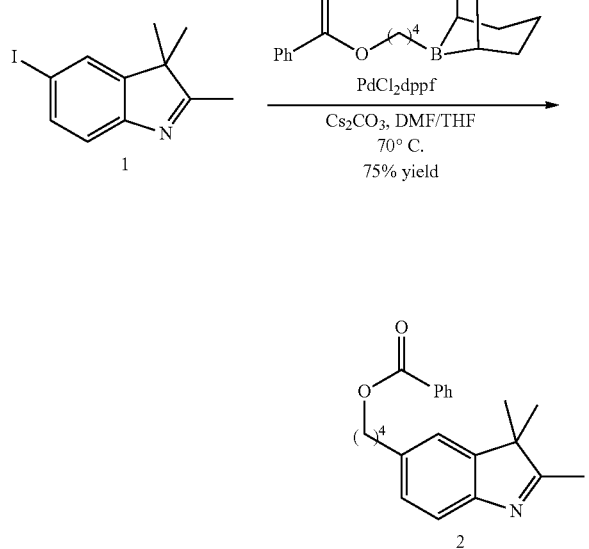

To a flask containing 3-buten-1-ol benzoate (3.0 g, 17.1 mmol) was added a 0.5 M solution of 9-borabicyclo[3.3.1]nonane (34.1 mL, 17.1 mmol) in THF. The clear, colorless solution was stirred at room temperature for 3 hours. In a separate flask fitted with a condenser was charged iodo indolenine (1, 3.4 g, 11.9 mmol), [1,1'-Bis(diphenylphosphino) ferrocene]palladium(II) dichloride (0.7 g, 0.8 mmol), and cesium chloride (6.0 g, 18.5 mmol). DMF (20 mL) was charged to the flask and the dark suspension was sparged with argon for 10 minutes. After addition of the benzoate borane/THF solution the reaction was heated to 70° C. for 12 hours. After this time HPLC indicated complete conversion of the starting indolenine 1. The reaction was cooled to room temperature, diluted with EtOAc (50 mL) and hexanes (50 mL), and filtered through celite. The organic layer was washed water (3×), bring, and dried over magnesium sulfate. After filtration and evaporation the crude residue was purified by normal phase chromatography (0→50% EtOAc/hexanes, $SiO_2$), affording indolenine 2 (3.0 g, 75% yield) as a viscous yellow oil. HRMS (ESI) calculated for $C_{22}H_{26}NO_2$ $(M+H)^+$ 336.1964, observed 336.1962.

A schlenk flask was charged with potassium iodide (2.0 g, 12.0 mmol) and flushed with argon. Indolenine (2, 2.0 g, 6.0 mmol) was added as a solution in acetonitrile (8.0 mL), 2-(2-bromoethyl)-1,3-dioxolane (1.4 mL, 12.0 mmol) was added and the sealed vessel was heated to 100° C. for 14 hours. The reaction was diluted with dichloromethane (20 mL) and the suspension was filtered through a fritted glass funnel. The filtrate was purified directly by normal phase chromatography (0→7% MeOH/DCM, $SiO_2$), affording indolenine 3 (1.9 g, 57% yield) as a beige solid. HRMS (ESI) calculated for $C_{27}H_{34}NO_4$ $(M)^+$ 436.2488, observed 436.2487.

Trimethine cyanine 4

-continued

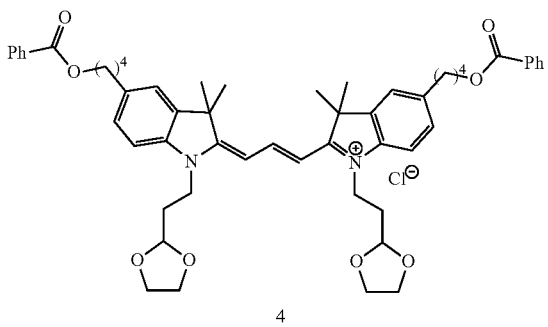

4

To an admixture of indolenine (3, 0.96 g, 1.7 mmol), diphenylformamidine (0.40 g, 2.1 mmol) and DMAP (21 mg, 0.17 mmol) was added acetic anhydride (5 mL). The brown mixture was heated to 120° C. for 1 hour. After cooling to room temperature the volatiles were concentrated in vacuo. To the crude intermediate was added an additional portion of indolenine (3, 1.6 g, 2.8 mmol), followed by ethanol (5 mL) and trimethylamine (1.2 mL, 8.6 mmol). The reaction was heated to reflux under argon for 1 hour. The reaction was diluted with aqueous sodium chloride and extracted with DCM. The organic layer was dried over magnesium sulfate, filtered and concentrated in vacuo. The crude residue was purified by normal phase chromatography (100% EtOAc, then 0→10% MeOH/DCM, SiO$_2$), affording Cy3 4 (0.9 g, 57% yield) as a dark purple solid. HRMS (ESI) calculated for C$_{55}$H$_{65}$N$_2$O$_8$ (M)$^+$ 881.4735, observed 881.4717.

Cy3B Analog 5

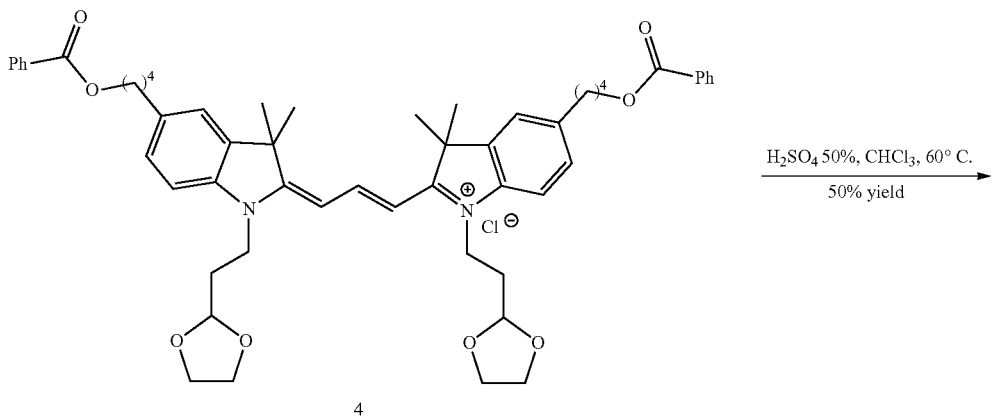

4

H$_2$SO$_4$ 50%, CHCl$_3$, 60° C.

50% yield

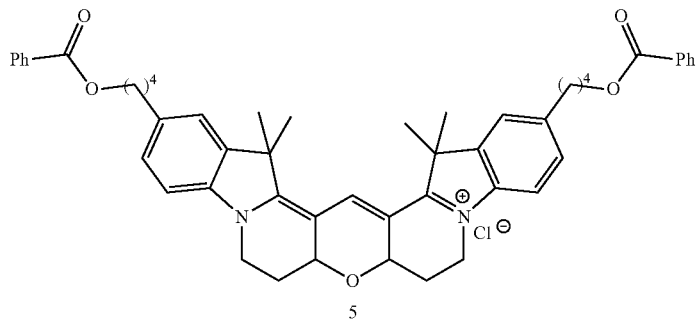

5

To a flask containing Cy3 4 (400 mg, 0.437 mmol) was added chloroform (6 mL) and sulfuric acid (4 mL, 50% v/v water). The biphasic mixture was stirred vigorously at 60° C. for 30 minutes, transitioning from a deep red to purple color. After cooling to room temperature the reaction was diluted with water (20 mL) and extracted with EtOAc (50 mL). The organic layer was washed with saturated aqueous sodium chloride, dried over magnesium sulfate, filtered, and concentrated in vacuo. The crude residue was purified by normal phase chromatography (100% EtOAc, then 0→15% MeOH/DCM, SiO$_2$), affording Cy3B 5 (177 mg, 50%/o yield) as a dark purple solid. HRMS (ESI) calculated for C$_{51}$H$_{55}$N$_2$O$_5$ (M)$^+$ 775.4105, observed 775.4091.

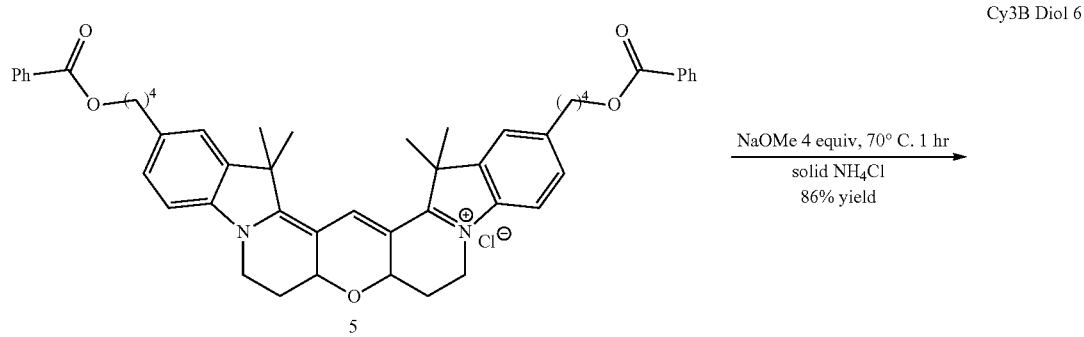

Cy3B Diol 6

NaOMe 4 equiv, 70° C. 1 hr
solid NH₄Cl
86% yield

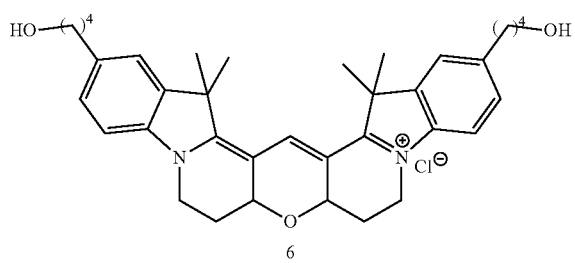

To a solution of Cy3B dibenzoate 5 (150 mg, 0.185 mmol) in methanol (4 mL), was added sodium methoxide (0.37 mL, 0.74 mmol, 2.0 M in MeOH). The reaction was heated to 70° C. for 1 hour. The reaction was quenched by addition of solid ammonium chloride (66 mg) and stirred for 30 minutes at room temperature. The volatiles were concentrated in vacuo and the crude re-dissolved in DCM (10 mL). The suspension was filtered and concentrated in vacuo. The crude residue was purified by normal phase chromatography (100% EtOAc, then 0→25% MeOH/DCM, SiO₂), affording Cy3B 6 (99 mg, 86% yield) as a dark purple solid. HRMS (ESI) calculated for $C_{37}H_{47}N_2O_3$ (M)⁺ 567.3581, observed 567.3568

Cy3B mono-MMT 7

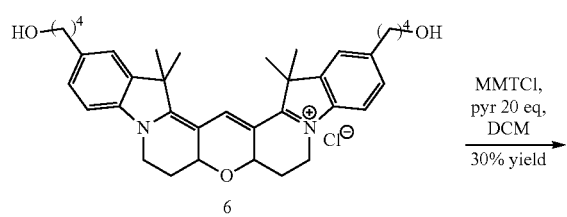

MMTCl,
pyr 20 eq,
DCM
30% yield

-continued

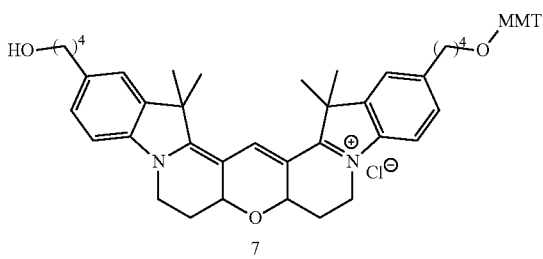

To a solution of Cy3B diol 6 (100 mg, 0.166 mmol) and monomethoxytrityl chloride (62 mg, 0.20 mmol) in dichloromethane was added pyridine (0.26 mL, 3.3 mmol). The dark purple reaction was stirred at room temperature for 30 minutes. The reaction was diluted with DCM and washed with water and saturated aqueous sodium chloride in succession. The organic layer was dried over magnesium sulfate, filtered, and concentrated in vacuo. The crude residue was purified by normal phase chromatography (100% EtOAc, then 0→25% MeOH/DCM with 1% Et₃N, SiO₂), affording Cy3B 7 (43 mg, 30% yield) as a dark purple solid. HRMS (ESI) calculated for $C_{57}H_3N_2O_4$ (M)⁺ 839.4782, observed 839.4751.

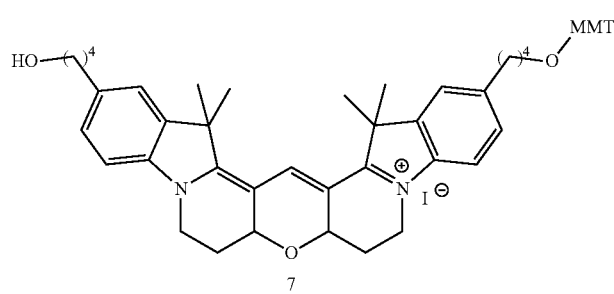
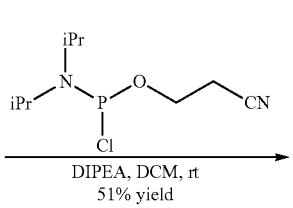
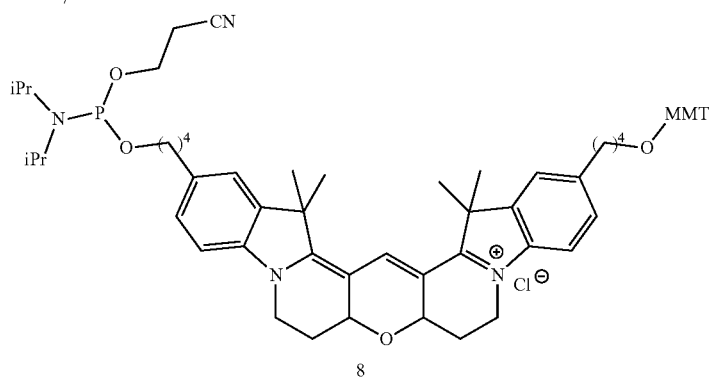

To a solution of Cy3B 7 (35 mg, 0.036 mmol) and N,N-diisopropylethylamine (14 μL, 0.079 mmol) in anhydrous dichloromethane was added 2-cyanoethyl N,N-diisopropylchlorophosphoramidite (9.4 mg, 0.040 mmol) at room temperature. The reaction was diluted with deoxygenated DCM, washed with aqueous potassium chloride, dried over magnesium sulfate, filtered, and concentrated in vacuo. The crude residue was purified by normal phase chromatography (0→2% MeOH/DCM with 1% Et$_3$N, basic alumina). The product was redissolved in DCM (1 mL) and precipitated into hexanes (25 mL). Drying under high vacuum afforded Cy3B 8 (20 mg, 51% yield) as a dark purple solid. HRMS (ESI) calculated for $C_{66}H_{80}N_4O_5P$ (M)$^+$ 1039.5861, observed 1039.5835.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion. i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B," the disclosure also contemplates the alternative embodiments "a composition consisting of A and B" and "a composition consisting essentially of A and B."

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

What is claimed is:

1. A labeled biomolecule of the formula:

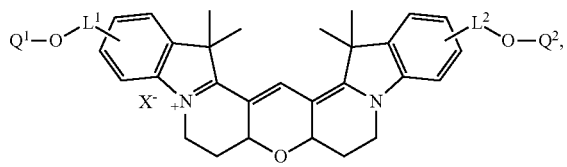

wherein:
Q$^1$ and Q$^2$ are independently monomeric or oligomeric biomolecules;
L$^1$ and L$^2$ are independently optionally substituted alkylene; and
X$^-$ is a counterion or is absent.

2. The labeled biomolecule of claim 1, wherein Q$^1$ and Q$^2$ are independently nucleosides, nucleotides, oligonucleotides, nucleic acids, or derivatives or fragments thereof.

3. The labeled biomolecule of claim 2, wherein Q$^1$ and/or Q$^2$ form a first oligonucleotide strand.

4. The labeled biomolecule of claim 3, further comprising a second oligonucleotide strand hybridized to the first oligonucleotide strand.

5. The labeled biomolecule of claim 1, wherein a nucleoside polyphosphate is attached through a terminal phosphate to Q$^1$ and/or Q$^2$.

6. The labeled biomolecule of claim 1, wherein the labeled biomolecule is of the formula:

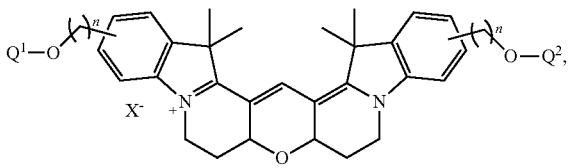

wherein n is independently an integer from 1-20, inclusive.

7. The labeled biomolecule of claim 6, wherein the labeled biomolecule is of the formula:

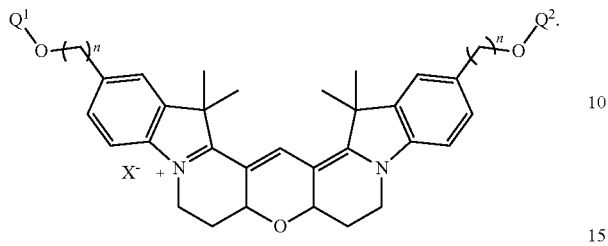

8. The labeled biomolecule of claim 7, wherein the labeled biomolecule is of the formula:

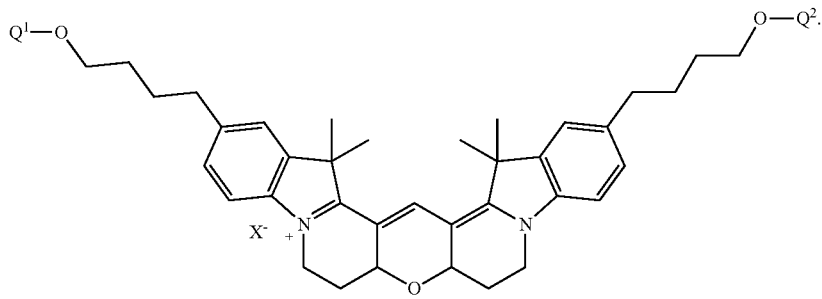

9. The labeled biomolecule of claim 1, wherein $L^1$ and $L^2$ are independently optionally substituted $C_{1-20}$ alkylene.

10. The labeled biomolecule of claim 9, wherein $L^1$ and $L^2$ are independently optionally substituted $C_{1-10}$ alkylene.

11. The labeled biomolecule of claim 3, wherein the first oligonucleotide strand comprises at least 10 and fewer than 200 nucleotides.

12. The labeled biomolecule of claim 11, wherein the first oligonucleotide strand comprises at least 10 and fewer than 100 nucleotides.

13. The labeled biomolecule of claim 12, wherein the first oligonucleotide strand comprises at least 10 and fewer than 50 nucleotides.

14. The labeled biomolecule of claim 1, wherein $Q^1$ and $Q^2$ are independently oligonucleotides, nucleic acids, or derivatives or fragments thereof, and wherein $Q^1$ and $Q^2$ form a first oligonucleotide strand.

15. The labeled biomolecule of claim 14, further comprising a second oligonucleotide strand hybridized to the first oligonucleotide strand.

* * * * *